United States Patent [19]

Fisher et al.

[11] Patent Number: 5,561,142
[45] Date of Patent: Oct. 1, 1996

[54] SUBSTITUTED SULFONAMIDES AS SELECTIVE $\beta_3$ AGONISTS FOR THE TREATMENT OF DIABETES AND OBESITY

[75] Inventors: Michael H. Fisher, Ringoes; Elizabeth M. Naylor, Scotch Plains; Dong Ok, Edison; Ann E. Weber, Scotch Plains; Thomas Shih; Hyun Ok, both of Edison, all of N.J.

[73] Assignee: Merck & Co., Inc., Rahway, N.J.

[21] Appl. No.: 445,630

[22] Filed: May 22, 1995

Related U.S. Application Data

[63] Continuation-in-part of Ser. No. 404,565, Mar. 21, 1995, abandoned, which is a continuation-in-part of Ser. No. 233,166, Apr. 26, 1994, abandoned.

[51] Int. Cl.⁶ .................. C07D 413/12; C07D 213/30; A61K 31/44; A61K 31/47
[52] U.S. Cl. .................. 514/312; 546/153; 546/194; 546/269; 546/271; 546/275; 546/276; 546/277; 546/286; 546/338; 514/318; 514/337; 514/338; 514/340; 514/342
[58] Field of Search .................. 546/153, 194, 546/269, 271, 275, 276, 277, 280, 338; 514/312, 318, 337, 338, 340, 342

[56] References Cited

U.S. PATENT DOCUMENTS

| | | | |
|---|---|---|---|
| 3,452,037 | 6/1969 | Santilli et al. | 514/365 |
| 3,816,516 | 6/1974 | Cox et al. | 514/653 |
| 4,000,193 | 12/1976 | Lunts et al. | 546/344 |
| 4,396,627 | 8/1983 | Ainsworth et al. | 424/309 |
| 4,478,849 | 10/1984 | Ainsworth et al. | 424/285 |
| 4,999,377 | 3/1991 | Ainsworth et al. | 424/285 |
| 5,017,619 | 5/1991 | Alig et al. | 514/653 |
| 5,153,210 | 10/1992 | Ainsworth et al. | 546/344 |
| 5,321,036 | 6/1994 | Sher | 514/366 |

FOREIGN PATENT DOCUMENTS

| | | |
|---|---|---|
| 0091749 | 10/1983 | European Pat. Off. |
| 0007206 | 1/1989 | European Pat. Off. |
| 0427480 | 5/1991 | European Pat. Off. |
| 0455006 | 11/1991 | European Pat. Off. |
| 0516350 | 12/1992 | European Pat. Off. |
| 0516349 | 12/1992 | European Pat. Off. |
| 0068669 | 1/1993 | European Pat. Off. |
| 0565317 | 10/1993 | European Pat. Off. |
| 0611003 | 8/1994 | European Pat. Off. |
| 1108577 | 4/1968 | United Kingdom. |
| 1565080 | 4/1990 | United Kingdom. |
| WO93/10074 | 5/1993 | WIPO. |
| WO93/22277 | 11/1993 | WIPO. |
| WO94/02493 | 2/1994 | WIPO. |
| WO94/29290 | 12/1994 | WIPO. |

OTHER PUBLICATIONS

A. A. Larsen, et al, Journal of Medicinal Chemistry, vol. 10, (3) pp. 462–472, 1967.

*Primary Examiner*—Zinna Northington Davis
*Attorney, Agent, or Firm*—Mollie M. Yang; David L. Rose

[57] ABSTRACT

Substituted sulfonamides are selective $\beta_3$ adrenergic receptor agonists with very little $\beta_1$ and $\beta_2$ adrenergic receptor activity and as such the compounds are capable of increasing lipolysis and energy expenditure in cells. The compounds thus have potent activity in the treatment of Type II diabetes and obesity. The compounds can also be used to lower triglyceride levels and cholesterol levels or raise high density lipoprotein levels or to decrease gut motility. In addition, the compounds can be used to reduced neurogenic inflammation or as antidepressant agents. The compounds are prepared by coupling an aminoalkylphenyl-sulfonamide with an appropriately substituted epoxide. Compositions and methods for the use of the compounds in the treatment of diabetes and obesity and for lowering triglyceride levels and cholesterol levels or raising high density lipoprotein levels or for increasing gut motility are also disclosed.

18 Claims, No Drawings

SUBSTITUTED SULFONAMIDES AS SELECTIVE β₃ AGONISTS FOR THE TREATMENT OF DIABETES AND OBESITY

CROSS-REFERENCE

This is a continuation-in-part of co-pending application U.S. patent application Ser. No. 08/404,565 filed Mar. 21, 1995, now abandoned, which is a continuation-in-part of U.S. patent application Ser. No. 08/233,166 filed Apr. 26, 1994, now abandoned these applications are hereby incorporated by reference in their entirety.

BACKGROUND OF THE INVENTION

β-Adrenoceptors have been subclassified as $\beta_1$ and $\beta_2$ since 1967. Increased heart rate is the primary consequence of $\beta_1$-receptor stimulation, while bronchodilation and smooth muscle relaxation typically result from $\beta_2$ stimulation. Adipocyte lipolysis was initially thought to be solely a $\beta_1$-mediated process. However, more recent results indicate that the receptor-mediating lipolysis is atypical in nature. These atypical receptors, later called $\beta_3$-adrenoceptors, are found on the cell surface of both white and brown adipocytes where their stimulation promotes both lipolysis (breakdown of fat) and energy expenditure.

Early developments in this area produced compounds with greater agonist activity for the stimulation of lipolysis ($\beta_3$ activity) than for stimulation of atrial rate ($\beta_1$) and tracheal relaxation ($\beta_2$). These early developments disclosed in Ainsworth et al., U.S. Pat. Nos. 4,478,849 and 4,396,627, were derivatives of phenylethanolamines.

Such selectivity for $\beta_3$-adrenoceptors could make compounds of this type potentially useful as antiobesity agents. In addition, these compounds have been reported to show antihyperglycemic effects in animal models of non-insulin-dependent diabetes mellitus.

A major drawback in treatment of chronic diseases with $\beta_3$ agonists is the potential for stimulation of other β-receptors and subsequent side effects. The most likely of these include muscle tremor ($\beta_2$) and increased heart rate ($\beta_1$). Although these phenylethanolamine derivatives do possess some $\beta_3$ selectivity, side effects of this type have been observed in human volunteers. It is reasonable to expect that these side effects resulted from partial $\beta_1$ and/or $\beta_2$ agonism.

More recent developments in this area are disclosed in Ainsworth et al., U.S. Pat. No. 5,153,210, Caulkett et al., U.S. Pat. No. 4,999,377, Alig et al., U.S. Pat. No. 5,017,619, Lecount et al., European Patent 427480 and Bloom et al., European Patent 455006.

Even though these more recent developments purport to describe compounds with greater $\beta_3$ selectivity over the $\beta_1$ and $\beta_2$ activities, this selectivity was determined using rodents, in particular, rats as the test animal. Because even the most highly selective compounds, as determined by these assays, still show signs of side effects due to residual $\beta_1$ and $\beta_2$ agonist activity when the compounds are tested in humans, it has become apparent that the rodent is not a good model for predicting human $\beta_3$ selectivity.

Recently, assays have been developed which more accurately predict the effects that can be expected in humans. These assays utilize cloned human $\beta_3$ receptors which have been expressed in Chinese hamster ovary cells. See Emorine et al, *Science*, 1989, 245:1118–1121; and Liggett, *Mol. Pharmacol.*, 1992, 42:634–637. The agonist and antagonist effects of the various compounds on the cultivated cells provide an indication of the antiobesity and antidiabetic effects of the compounds in humans.

SUMMARY OF THE INVENTION

The instant invention is concerned with substituted sulfonamides which are useful as antiobesity and antidiabetic compounds. Thus, it is an object of this invention to describe such compounds. It is a further object to describe the specific preferred stereoisomers of the substituted sulfonamides. A still further object is to describe processes for the preparation of such compounds. Another object is to describe methods and compositions which use the compounds as the active ingredient thereof.

Further objects will become apparent from reading the following description.

DESCRIPTION OF THE INVENTION

The present invention provides compounds having the formula I:

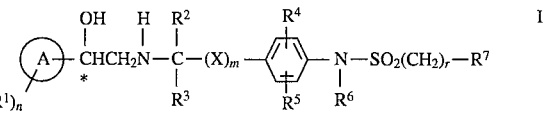

where n is m is 0 to 5;

0 or 1;

r is 0 to 3;

A is (1) a 5 or 6-membered heterocyclic ring with from 1 to 4 heteroatoms selected from oxygen, sulfur and nitrogen, 2) a benzene ring fused to a 5 or 6-membered heterocyclic ring with from 1 to 4 heteroatoms selected from oxygen, sulfur and nitrogen, 3) a 5 or 6-membered heterocyclic ring with from 1 to 4 heteroatoms selected from oxygen, sulfur and nitrogen fused to a 5 or 6-membered heterocyclic ring with from 1 to 4 heteroatoms selected from oxygen, sulfur and nitrogen, (4) phenyl, or (5) a benzene ring fused to a $C_3$–$C_8$ cycloalkyl ring;

$R^1$ is (1) hydroxy, (2) oxo, (3) halogen, (4) cyano, (5) $NR^8R^8$, (6) SRS, (7) trifluoromethyl, (8) $C_1$–$C_{10}$ alkyl, (9) ORS, (10) $SO_2R^9$, (11) $OCOR^9$, (12) $NR^8COR^9$, (13) $COR^9$, (14) $NR^8SO_2R^9$, (15) $NR^8CO_2R^8$, or (16) $C_1$–$C_{10}$ alkyl substituted by hydroxy, halogen, cyano, $NR^8R^8$, $SR^8$, trifluoromethyl, $OR^8$, $C_3$–$C_8$ cycloalkyl, phenyl, $NR^8COR^9$, $COR^9$, $SO_2R^9$, $OCOR^9$, $NR^8SO_2R^9$ or $NR^8CO_2R^8$;

$R^2$ and $R^3$ are independently (1) hydrogen, (2) $C_1$–$C_{10}$ alkyl or (3) $C_1$–$C_{10}$ alkyl with 1 to 4 substituents selected from hydroxy, $C_1$–$C_{10}$ alkoxy, and halogen;

X is (1) —$CH_2$—, (2) —$CH_2$—$CH_2$—, (3) —CH=CH— or (4) —$CH_2O$—;

$R^4$ and $R^5$ are independently (1) hydrogen, (2) $C_1$–$C_{10}$ alkyl, (3) halogen, (4) $NHR^8$, (5) $OR^8$, (6) $SO_2R^9$ or (7) $NHSO_2R^9$;

R6 is (1) hydrogen or (2) $C_1$–$C_{10}$ alkyl;

$R^7$ is Z-$(R^{1a})_n$;

$R^{1a}$ is (1) $R^1$, with the proviso that when A is phenyl, $R^{1a}$ is not $C_1$–$C_{10}$ alkyl, (2) $C_3$–$C_8$ cycloalkyl, 3) phenyl optionally substituted with up to 4 groups independently selected from $R^8$, $NR^8R^8$, $OR^8$, $SR^8$ and halogen, or (4) 5 or 6-membered heterocycle with from 1 to 4 heteroatoms selected from oxygen, sulfur and nitrogen, optionally substituted with up to four groups independently selected from oxo, $R^8$, $NR^8R^8$, $OR^8$, $SR^8$, and halogen;

Z is (1) phenyl, (2) naphthyl, (3) a 5 or 6-membered heterocyclic ring with from 1 to 4 heteroatoms selected from oxygen, sulfur and nitrogen, (4) a benzene ring fused to a $C_3$-$C_8$ cycloalkyl ring, (5) a benzene ring fused to a 5 or 6-membered heterocyclic ring with from 1 to 4 heteroatoms selected from oxygen, sulfur and nitrogen, (6) a 5 or 6-membered heterocyclic ring with from 1 to 4 heteroatoms selected from oxygen, sulfur and nitrogen fused to a 5 or 6-membered heterocyclic ring with from 1 to 4 heteroatoms selected from oxygen, sulfur and nitrogen, or (7) a 5 or 6-membered heterocyclic ring with from 1 to 4 heteroatoms selected from oxygen, sulfur and nitrogen fused to a $C_3$-$C_8$ cycloalkyl ring;

$R^8$ is (1) hydrogen, (2) $C_1$-$C_{10}$ alkyl, (3) $C_3$-$C_8$ cycloalkyl, (4) Z optionally having 1 to 4 substituents selected from halogen, nitro, oxo, $NR^{10}R^{10}$, $C_1$-$C_{10}$ alkyl, $C_1$-$C_{10}$ alkoxy, $C_1$-$C_{10}$ alkylthio, and $C_1$-$C_{10}$ alkyl having 1 to 4 substituents selected from hydroxy, halogen, $CO_2H$, $CO_2$-$C_1$-$C_{10}$ alkyl, $SO_2$-$C_1$-$C_{10}$ alkyl, $C_3$-$C_8$ cycloalkyl, $C_1$-$C_{10}$ alkoxy, and Z optionally substituted by from 1 to 3 of halogen, $C_1$-$C_{10}$ alkyl or $C_1$-$C_{10}$ alkoxy, or (5) $C_1$-$C_{10}$ alkyl having 1 to 4 substituents selected from hydroxy, halogen, $CO_2H$, $CO_2$—$C_1$-$C_{10}$ alkyl, $SO_2$—$C_1$—$C_{10}$ alkyl, $C_3$-$C_8$ cycloalkyl, $C_1$-$C_{10}$ alkoxy, $C_1$-$C_{10}$ alkyl, and Z optionally substituted by from 1 to 4 of halogen, $C_1$-$C_{10}$ alkyl or $C_1$-$C_{10}$ alkoxy;

$R^9$ is (1) $R^8$ or (2) $NR^8R^8$;

$R^{10}$ is (1) $C_1$-$C_{10}$ alkyl, or (2) two $R^{10}$ groups together with the N to which they are attached formed a 5 or 6-membered ring optionally substituted with $C_1$-$C_{10}$ alkyl; or a pharmaceutically acceptable salt thereof.

In one embodiment of the instant invention A is a 5 or 6-membered heterocyclic ring with from 1 to 4 heteroatoms selected from oxygen, sulfur and nitrogen, a benzene ring fused to a 5 or 6-membered heterocyclic ring with from 1 to 4 heteroatoms selected from oxygen, sulfur and nitrogen, or a 5 or 6-membered heterocyclic ring with from 1 to 4 heteroatoms selected from oxygen, sulfur and nitrogen fused to a 5 or 6-membered heterocyclic ring with from 1 to 4 heteroatoms selected from oxygen, sulfur and nitrogen.

In another embodiment of the instant invention A is phenyl or benzene fused to a $C_3$-$C_8$ cycloalkyl ring.

Preferred compounds of the instant invention are realized when in the above structural formula I:

$R^2$ and $R^3$ are hydrogen or methyl;

X is —$CH_2$—;

n is 0 to 3;

m is 1;

r is 0 to 2; and $R^4$, $R^5$ and $R^6$ are hydrogen.

Other preferred compounds of the instant invention are realized when in the above structural formula I:

A is phenyl or a 6-membered heterocyclic ring with 1 or 2 heteroatoms selected from nitrogen and sulfur;

$R^1$ is hydroxy, halogen, cyano, trifluoromethyl, $NR^8R^8$, $NR^8SO_2R^9$, $NR^8COR^9$, $NRSCO_2R^8$, $C_1$-$C_6$ alkyl optionally substituted by hydroxy; and r is 0 or 2.

More preferred compounds are represented by the formula Ia:

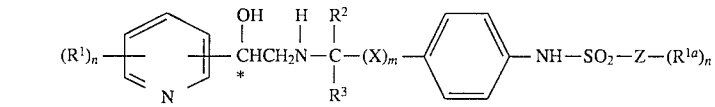

wherein n is 0 to 3;

m is 1

$R^1$ is (1) halogen or (2) $NR^8R^8$;

$R^2$, $R^3$ are independently hydrogen or methyl;

$R^{1a}$ is (1) halogen, (2) $C_1$-$C_{10}$ alkyl, (3) $NR^8R^8$, (4) $NR^8COR^9$, (5) $NR^8CO_2R^8$, (6) $COR^9$, (7) $OCOR^9$, or (8) a 5 or 6-membered heterocycle with from 1 to 4 heteroatoms selected from oxygen, sulfur and nitrogen, optionally substituted with up to four groups independently selected from oxo, halogen, $R^8$, $NR^8R^8$, $OR^8$, and $SR^8$;

Z is (1) phenyl, (2) naphthyl, (3) a 5 or 6-membered heterocyclic ring with from 1 to 4 heteroatoms selected from oxygen, sulfur and nitrogen, (4) benzene ring fused to a 5 or 6-membered heterocyclic ring with from 1 to 3 heteroatoms selected from oxygen, sulfur and nitrogen, or (5) a 5 or 6-membered heterocyclic ring with from 1 to 4 heteroatoms selected from oxygen, sulfur and nitrogen fused to a $C_3$-$C_8$ cycloalkyl ting;

X is —$CH_2$—; and $R^8$ and $R^9$ are as defined in claim 1.

Even more preferred compounds are those represented by formula Id:

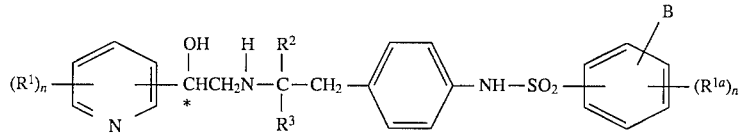

n is 0 or 1;

$R^1$ is $NR^8R^8$;

$R^2$ and $R^3$ are independently (1) hydrogen, or (2) methyl;

B is (1) hydrogen, (2) benzene fused to the benzene ring to form naphthyl, or (3) a 5 or 6-membered heterocycle with 1 to 4 heteroatoms selected from oxygen, sulfur and nitrogen atom fused to the benzene ring;

$R^{1a}$ is (1) halogen, (2) $C_1$-$C_{10}$ alkyl, (3) $NR^8R^8$, (4) $NR^8COR^9$, (5) $NR^8CO_2R^8$, (6) $COR^9$, or (7) a 5 or 6-membered heterocycle with from 1 to 4 heteroatoms selected from oxygen, sulfur and nitrogen, optionally substituted with up to four groups independently selected from oxo, $R^8$, $SR^8$, $OR^8$, and $NR^8R^8$; when B and the benzene ring form a fused ring system, $R^{1a}$ is attached to either ring;

$R^8$ is (1) hydrogen, (2) $C_1$–$C_{10}$ alkyl, (3) Z optionally having 1 to 4 substituents selected from nitro, oxo, and $NR^{10}R^{10}$, or (5) $C_1$–$C_{10}$ alkyl having 1 to 4 substituents selected from hydroxy, halogen, $C_1$–$C_{10}$ alkyl, $C_3$–$C_8$ cycloalkyl, and Z optionally substituted by from 1 to 4 of halogen, $C_1$–$C_{10}$ alkyl or $C_1$–$C_{10}$ alkoxy;

$R^9$ is (1) $R^8$ or (2) $NR^8R^8$;

$R^{10}$ is (1) $C_1$–$C_{10}$ alkyl, or
(2) two $R^{10}$ groups together with the N to which they are attached formed a 5 or 6-membered ring optionally substituted with $C_1$–$C_{10}$ alkyl; and Z is (1) phenyl, (2) a 5 or 6-membered heterocyclic ring with from 1 to 4 heteroatoms selected from oxygen, sulfur and nitrogen, (3) a benzene ring fused to a 5 or 6-membered heterocyclic ring with from 1 to 4 heteroatoms selected from oxygen, sulfur and nitrogen, or (4) a 5 or 6-membered heterocyclic ring with from 1 to 4 heteroatoms selected from oxygen, sulfur and nitrogen fused to a $C_3$–$C_8$ cycloalkyl ring. Most preferred compounds are those having the formula Ie

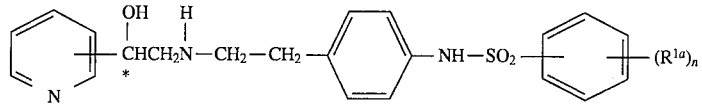

n is 0 or 1;

$R^{1a}$ is (1) halogen, (2) $NR^8COR^9$, or (3) a 5-membered heterocycle substituted with 0 or 1 oxo selected from imidazolidinone, imidazolone, oxadiazole, oxazole, triazole and tetrazolone, optionally substituted with up to three groups independently selected from $R^8$;

$R^8$ is (1) hydrogen, (2) $C_1$–$C_{10}$ alkyl, or (3) $C_1$–$C_{10}$ alkyl having 1 to 4 substituents selected from hydroxy, halogen, $C_1$–$C_{10}$ alkyl, $C_3$–$C_8$ cycloalkyl, and Z optionally substituted by from 1 to 4 of halogen, $C_1$–$C_{10}$ alkyl or $C_1$–$C_{10}$ alkoxy;

$R^9$ is $NR^8R^8$;

Z is phenyl.

Other more preferred compounds are represented by formula Ib:

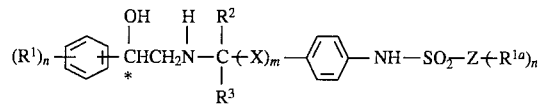

wherein n is 0 to 3;

m is $R^{1a}$ is (1) hydroxy, (2) cyano, (3) $NR^8R^8$ or (4) halogen;

$R^{1a}$ is (1) halogen, (2) $NR^8R^8$, (3) $NR^8COR^9$, (4) $NR^8CO_2R^8$, (5) $OCOR^9$, or (6) a 5 or 6-membered heterocycle with from 1 to 4 heteroatoms selected from oxygen, sulfur and nitrogen, optionally substituted with up to three groups independently selected from oxo, halogen, $R^8$, $NR^8R^8$, $OR^8$ and $SR^8$;

Z is (1) phenyl, (2) naphthyl or (3) benzene ring fused to a 5 or 6-membered heterocyclic ring with from 1 to 4 heteroatoms selected from oxygen, sulfur and nitrogen;

X is —$CH_2$—; and $R^2$ and $R^3$ are independently hydrogen or methyl.

Representative antiobesity and antidiabetic compounds of the present invention include the following:

N-[4-[2-[[2-hydroxy-2-(6-aminopyridin-3-yl)ethyl]amino]ethyl]phenyl]- 4-(hexylaminocarbonylamino)benzenesulfonamide N-[4-[2-[[2-hydroxy-2-(6-aminopyridin-3-yl)ethyl]amino]ethyl]phenyl]- 4-iodobenzenesulfonamide N-[4-[2-[[2-hydroxy-2-(6-aminopyridin-3-yl)ethyl]amino]ethyl]phenyl]-benzenesulfonamide N-[4-[2-[[2-hydroxy-2-(6-aminopyridin-3-yl)ethyl]amino]ethyl]phenyl]- 2-naphthalenesulfonamide N-[4-[2-[[2-hydroxy-2-(6-aminopyridin-3-yl)ethyl]amino]ethyl]phenyl]- 3-quinolinesulfonamide N-[4-[2-[[2-hydroxy-2-(6-aminopyridin-3-yl)ethyl]amino]ethyl]phenyl]- 5-benzisoxazolesulfonamide N-[4-[2-[[2-hydroxy-2-(6-aminopyridin-3-yl)ethyl]amino]ethyl]phenyl]- 4-[(hexylmethylaminocarbonyl)amino]benzenesulfonamide N-[4-[2-[[2-hydroxy-2-(6-aminopyridin-3-yl)ethyl]amino]ethyl]phenyl]- 4-[(dimethylaminocarbonyl)amino]benzenesulfonamide N-[4-[2-[[2-hydroxy-2-(6-aminopyridin-3-yl)ethyl]amino]ethyl]phenyl]- 4-(3-hexyl-2-imidazolidon- 1-yl)benzenesulfonamide N-[4-[ 3-[[2-hydroxy-2-(6-aminopyridin-3-yl)ethyl]amino]propyl]-phenyl]- 4-(hexylaminocarbonylamino)benzenesulfonamide N-[4-[3-[[2-hydroxy-2-(6-aminopyridin-3-yl)ethyl]amino]propyl]-phenyl]- 4-iodobenzenesulfonamide N-[4-[3-[[2-hydroxy-2-(6-aminopyridin-3-yl)ethyl]amino]propyl]-phenyl]benzenesulfonamide N-[4-[ 3-[[2-hydroxy-2-(6-aminopyridin-3-yl)ethyl]amino]propyl]-phenyl]- 2-naphthalenesulfonamide N-[4-[3-[[2-hydroxy-2-(6-aminopyridin-3-yl)ethyl]amino]propyl]-phenyl]- 3-quinolinesulfonamide N-[4-[2-[[2-hydroxy-2-(3-pyridinyl)ethyl]amino]ethyl]phenyl]- 4-(hexylaminocarbonylamino)benzenesulfonamide N-[4-[2-[[2-hydroxy-2-(3-pyridinyl)ethyl]amino]ethyl]phenyl]- 4-isopropylbenzenesulfonamide N-[4-[2-[[2-hydroxy-2-(3-pyridinyl)ethyl]amino]ethyl]phenyl]- 2-naphthalenesulfonamide N-[4-[2-[[2-hydroxy-2-(3-pyridinyl)ethyl]amino]ethyl]phenyl]- 3-quinolinesulfonamide N-[4-[ 2-[[ 2-hydroxy-2-(3-pyridinyl)ethyl]amino ]ethyl]phenyl]- 4-[(hexylmethylaminocarbonyl)amino]benzenesulfonamide N-[4-[2-[[2-hydroxy-2-(3-pyridinyl)ethyl]amino]ethyl]phenyl]-4-( 3-hexyl-2-imidazolidinon-1-yl)benzenesulfonamide N-[4-[2-[[2-hydroxy-2-(3-pyridinyl)ethyl]amino]ethyl]phenyl]- 4-iodobenzenesulfonamide N-[4-[2-[[2-hydroxy-2-(3-pyridinyl)ethyl]amino]ethyl]phenyl]-4-[5-( 3-cyclopentylpropyl)-[1,2,4]-oxadiazol-3-yl]benzensulfonamide N-[4-[2-[[2-hydroxy-2-(3-pyridinyl)ethyl]amino]ethyl]phenyl]-4-[( 1-oxoheptyl)amino]benzenesulfonamide N-[4-[2-[[2-hydroxy-2-(3-pyridinyl)ethyl]amino]ethyl]phenyl]-4-[(1-oxo- 4-phenylbutyl)amino]benzenesulfonamide N-[4-[2-[[2-hydroxy-2-(3-pyridinyl)ethyl]amino]ethyl]phenyl]- 4-[(propoxycarbonyl)amino]benzenesulfonamide N-[4-[2-[[2-hydroxy-2-(3-pyridinyl)ethyl]amino]ethyl]phenyl]-4-[[[(fur- 2-ylmethyl)amino]carbonyl]amino]benzenesulfonamide N-[4-[2-[[2-hydroxy-2-(3-pyridinyl)ethyl]amino]ethyl]phenyl]-4-[[[( 2-phenylethyl)amino]carbonyl]amino]benzenesulfonamide N-[4-[2-[[2-hydroxy-2-(3-pyridinyl)ethyl]amino]ethyl]phenyl]-4-[[[( 2-indol-3-ylethyl)amino]carbonyl]amino]benzenesulfonamide N-[4-[2-[[2-hydroxy-2-(3-pyridinyl)ethyl]amino]ethyl]phenyl]- 4-[[(octylamino)carbonyl]amino]benzenesulfonamide N-[4-[2-[[2-hydroxy-2-(3-pyridinyl)ethyl]amino]ethyl]phenyl]- 1-[(hexylamino)carbonyl]-5-indolinesulfonamide N-[4-[2-[[2-hydroxy-2-(3-pyridinyl)ethyl]amino]ethyl]phenyl]- 1-[(octylamino)carbonyl]-5-indolinesulfonamide N-[4-[2-[[2-hydroxy-2-(3-pyridinyl)ethyl]amino]ethyl]phenyl]- 1-[(N-methyl-N-octylamino)carbonyl]-5-indolinesulfonamide N-[4-[2-[[2-hydroxy-2-(3-pyridinyl)ethyl]amino]ethyl]phenyl]-1-( 1-oxononyl)-5-indolinesulfonamide N-[4-[2-[[2-hydroxy-2-(3-pyridinyl)ethyl]amino]ethyl]phenyl]- 1-( 4-methylthiazo-1-2-yl)-5-indolinesulfonamide N-[4-[2-[[2-hydroxy-2-(3-pyridinyl)ethyl]amino]ethyl]phenyl]- 1-( 4-octylthiazol-2-yl)-5-indolinesulfonamide N-[4-[2-[[2-hydroxy-2-(3-pyridinyl)ethyl]amino]ethyl]phenyl]-1-( 4-ethyl-5-methylthiazol-2-yl)-5-indolinesulfonamide N-[4-[2-[[2-hydroxy-2-(3-pyridinyl )ethyl]amino]ethyl]phenyl]-4-( 3-octyl-2imidazolidinon-1-yl)benzenesulfonamide N-[4-[2-[[2-hydroxy-2-(3-pyridinyl)ethyl]amino]ethyl]phenyl]-4-[3-( 4,4,4-trifluorobutyl)-2-imidazolidinon-1-yl]benzenesulfonamide N-[4-[2-[[2-hydroxy-2-(3-pyridinyl)ethyl]amino]ethyl]phenyl]-4-[3-( 3-phenylpropyl)-2-imidazolidinon- 1-yl]benzenesulfonamide N-[4-[2-[[2-hydroxy-2-(3-pyridinyl)ethyl]amino]ethyl]phenyl]-4-[3-(4,4,5,5,5-pentafluoropentyl)-2-imidazolidinon-1-yl]benzenesulfonamide N-[4-[2-[[2-hydroxy-2-(3-pyridinyl)ethyl]amino]ethyl]phenyl]-4-[3-( 2-cyclohexylethyl)-2-imidazolidinon- 1-yl]benzenesulfonamide N-[4-[2-[[2-hydroxy-2-(3-pyridinyl)ethyl]amino]ethyl]phenyl]-4-[3-[3-(4-chlorophenyl)propyl]-2-imidazolidinon-1-yl]benzenesulfonamide N-[4-[2-[[2-hydroxy-2-(3-pyridinyl)ethyl]amino]ethyl]phenyl]-4-( 3-pentyl-2-imidazolidinon-1-yl)benzenesulfonamide N-[4-[2-[[ 2-hydroxy-2-(3-pyridinyl )ethyl]amino]ethyl]phenyl]-4-[ 3-( 3-cyclopentylpropyl)-2-imidazolidinon-1-yl]benzenesulfonamide N-[4-[2-[[2-hydroxy-2-(3-pyridinyl)ethyl]amino]ethyl]phenyl]- 4-[cyclopentylethyl)-2-imidazolidinon- 1-yl]benzenesulfonamide N-[4-[2-[[2-hydroxy-2-(3-pyridinyl)ethyl]amino]ethyl]phenyl]-4-[3-( 3-cyclohexylpropyl)-2-imidazolidinon- 1-yl]benzenesulfonamide N-[4-[2-[[2-hydroxy-2-(3-pyridinyl)ethyl]amino]ethyl]phenyl]-4-[3-( 2,2-dimethylhexyl)-2-imidazolidinon- 1-yl]benzenesulfonamide N-[4-[2-[[2-hydroxy-2-(3-pyridinyl)ethyl]amino]ethyl]phenyl]-4-( 3-hexyl-2-imidazolon-1-yl)benzenesulfonamide N-[4-[2-[[2-hydroxy-2-(3-pyridinyl)ethyl]amino]ethyl]phenyl]-4-[3-( 4,4,4-trifluorobutyl)-2-imidazolon- 1-yl]benzenesulfonamide N-[4-[2-[[2-hydroxy-2-(3-pyridinyl)ethyl]amino]ethyl]phenyl]-4-(3-octyl- 2-imidazolon-1-yl)benzenesulfonamide N-[4-[ 2-[[ 2-hydroxy-2-(3-pyridinyl)amino]ethyl]phenyl]-4-[3-( 3-cyclopentylpropyl)-2-imidazolon- 1-yl]benzenesulfonamide N-[4-[2-[[2-hydroxy-2-(3-pyridinyl)ethyl]amino]ethyl]phenyl]-4-(2-octyl- 3-oxo-[1,2,4]-triazol-4-yl)benzenesulfonamide N-[4-[2-[[2-hydroxy-2-(3-pyridinyl)ethyl]amino]ethyl]phenyl]-4-( 4-hexyl-5-tetrazolon-1-yl)benzenesulfonamide N-[4-[2-[[2-hydroxy-2-(3-pyridinyl)ethyl]amino]ethyl]phenyl]-4-(4-octyl- 5-tetrazolon-1-yl)benzenesulfonamide N-[4-[2-[[2-hydroxy-2-(3-pyridinyl)ethyl]amino]ethyl]phenyl]-4-[4-( 3-cyclopentylpropyl)-5-tetrazolon- 1-yl]benzenesulfonamide N-[4-[2-[[2-hydroxy-2-(3-pyridinyl)ethyl]amino]ethyl]phenyl]-4-( 2-pentyloxazol-5-yl)benzenesulfonamide N-[4-[2-[[2-hydroxy-2-(3-pyridinyl)ethyl]amino]ethyl]phenyl]-4-( 2-octyloxazol-5-yl)benzenesulfonamide N-[4-[2-[[2-hydroxy-2-(3-pyridinyl)ethyl]amino]ethyl]phenyl]-4-[2-( 2-cyclopentylethyl)oxazol-5-yl]benzenesulfonamide N-[4-[2-[[2-hydroxy-2-(3-pyridinyl)ethyl]amino]ethyl]phenyl]-4-[( 4-ethyl-5-methylthiazol-2-yl)amino]benzenesulfonamide N-[4-[2-[[2-hydroxy-2-(3-pyridinyl)ethyl]amino]ethyl]phenyl]-4-[( 4,5,6,7-tetrahydrobenzothiazol-2-yl)amino]benzenesulfonamide N-[4-[2-[[2-hydroxy-2-(3-pyridinyl)ethyl]amino]ethyl]phenyl]-4-( 2-hexylimidazol-4-yl)benzenesulfonamide N-[4-[2-[[2-hydroxy-2-(3-pyridinyl)ethyl]amino]ethyl]phenyl]-4-( 1-methyl-2-octylimidazol-5-yl)benzenesulfonamide N-[4-[2-[[2-hydroxy-2-(3-pyridinyl)ethyl]amino]ethyl]phenyl]-4-[ 1-methyl-2-(cyclopentylethyl)imidazol-5-yl]benzenesulfonamide N-[4-[2-[[2-hydroxy-2-(3-pyridinyl)ethyl]amino]ethyl]phenyl]-4-[ 1-methyl-2-[2-(4-fluorophenyl)ethyl]imidazol-5-yl]benzenesulfonamide N-[4-[2-[[2-hydroxy-2-(3-pyridinyl)ethyl]amino]ethyl]phenyl]-4-( 5-pentyl-[1,2,4]-oxadiazol-3-yl)benzenesulfonamide N-[4-[2-[[2-hydroxy-2-(3-pyridinyl)ethyl]amino]ethyl]phenyl]-4-[5-( 2-cyclopentylethyl)-[1,2,4]-oxadiazol-3-yl]benzenesulfonamide N-[4-[2-[[2-hydroxy-2-(3-pyridinyl)ethyl]amino]ethyl]phenyl]-4-( 5-heptyl-[1,2,4]-oxadiazol-3-yl)benzenesulfonamide N-[4-[2-[[2-hydroxy-2-(3-pyridinyl)ethyl]amino]ethyl]phenyl]-4-( 5-octyl-[1,2,4]-oxadiazol-3-yl)benzenesulfonamide N-[4-[2-[[2-hydroxy-2-(3-pyridinyl)ethyl]amino]ethyl]phenyl]-4-( 5-hexylthio-[1,2,4]-triazol-3-yl)benzenesulfonamide N-[4-[2-[[2-hydroxy-2-(3-pyridinyl)ethyl]amino]ethyl]phenyl]-4-[[4-(4-propylpiperidin-1-yl)-1,1-dioxo-[1,2,5]-thiadiazol- 3-yl]amino]benzenesulfonamide N-[4-[2-[[2-hydroxy-2-(3-pyridinyl)ethyl]amino]ethyl]phenyl]-4-[[4-(hexylmethylamino)-1,1-dioxo-[1,2,5]-thiadiazol- 3-yl]amino]benzenesulfonamide N-[4-[2-[[2-hydroxy-2-(3-pyridinyl)ethyl]amino]ethyl]phenyl]-4-[[4-(heptylmethylamino)-1,1-dioxo-[1,2,5]-thiadiazol- 3-yl]amino]benzenesulfonamide N-[4-[2-[[2-hydroxy-2-(3-pyridinyl)ethyl]amino]ethyl]phenyl]-4-( 1-octyl-2,4-imidazolidinedion-3-yl)benzenesulfonamide N-[4-[2-[[2-hydroxy-2-(3-pyridinyl)ethyl]amino]ethyl]phenyl]-4-[3-(3-nitrophenyl)-5-pyrazolon- 1-yl]benzenesulfonamide N-[4-[2-[[2-hydroxy-2-(3-pyridinyl)ethyl]amino]ethyl]phenyl]-4-[4-( 1-hydroxy-1-hexylheptyl)-5-methyl-[1,2,3]-triazol-2-yl]benzenesulfonamide N-[4-[2-[[2-hydroxy-2-(3-pyridinyl)ethyl]amino]ethyl]phenyl]-4-[4-( 1-hydroxyheptyl)-5-methyl-[1,2,3 ]-triazol-2-yl]benzenesulfonamide N-[4-[2-[[2-hydroxy-2-(3-pyridinyl)ethyl]amino]-2-methylpropyl]-phenyl]- 4-(3-hexyl-2-imidazolidinon- 1-yl)benzenesulfonamide N-[4-[2-[[2-hydroxy-2-(3-pyridinyl)ethyl]amino]-2-methylpropyl]-phenyl]- 4-iodobenzenesulfonamide N-[4-[2-[[2-hydroxy-2-(3-pyridinyl)ethyl]amino]-2-methylpropyl]-phenyl]- 4-[[(hexylamino)carbonyl]amino]benzenesulfonamide N-[4-[2-[(2-hydroxy-2-phenylethyl)amino]ethyl]phenyl]-4-iodobenzene-sulfonamide N-[4-[2-[(2-hydroxy-2-phenylethyl)amino]ethyl]phenyl]-2-naphthalene-sulfonamide N-[4-[2-[(2-hydroxy-2-phenylethyl)amino]ethyl]phenyl]-3-quinoline-sulfonamide N-[4-[2-[[2-hydroxy-2-(3-chlorophenyl)ethyl]amino]ethyl]phenyl]- 3-isopropylbenzenesulfonamide N-[4-[2-[[2-hydroxy-2-(3-chlorophenyl)ethyl]amino]ethyl]phenyl]- 2-naphthalenesulfonamide N-[4-[2-[[2-hydroxy-2-(3-chlorophenyl)ethyl]amino]ethyl]phenyl]- 3-quinolinesulfonamide N-[4-[2-[[2-hydroxy-2-(4-amino-3,5-dichlorophenyl)ethyl]amino]ethyl]-phenyl]- 4-(hexylaminocarbonylamino)benzenesulfonamide N-[4-[2-[[2-hydroxy-2-(4-amino-3,5-dichlorophenyl)ethyl]amino]ethyl]-phenyl]- 1-[(octylamino)carbonyl]-5-indolinesulfonamide N-[4-[2-[[2-hydroxy-2-(4-amino-3,5-dichlorophenyl)ethyl]amino]ethyl]-phenyl]- 4-(3-hexyl-2-imidazolidinon-1-yl-)benzenesulfonamide N-[4-[2-[[2-hydroxy-2-(4-amino-3,5-dichlorophenyl)ethyl]amino]ethyl]-phenyl]- 4-(3-octyl-2-imidazolidinon- 1-yl-)benzenesulfonamide N-[4-[2-[[2-hydroxy-2-(4-hydroxyphenyl)ethyl]amino]ethyl]phenyl]-benzenesulfonamide N-[4-[2-[[2-hydroxy-2-(4-hydroxyphenyl)ethyl]amino]ethyl]phenyl]- 4-iodobenzenesulfonamide N-[4-[2-[[2-hydroxy-2-(3-cyanophenyl)ethyl]amino]ethyl]phenyl]- 4-(hexylaminocarbonylamino)benzenesulfonamide N-[4-[2-[[2-hydroxy-2-(3-cyanophenyl)ethyl]amino]ethyl]phenyl]- 3-quinolinesulfonamide N-[4-[2-[[2-hydroxy-2-(3-pyfidinyl)ethyl]amino]ethyl]phenyl]-4-( 5-hexyl-[1,2,4]-oxadiazol-3-yl)benzenesulfonamide N-[4-[2-[[2-hydroxy-2-(3-pyridinyl)ethyl]amino]ethyl]phenyl]-4-( 4-heptyl-5-methyl-[1,2,3]-tfiazol-2-yl)benzenesulfonamide N-[4-[2-[[2-hydroxy-2-(3-pyfidinyl)ethyl]amino]ethyl]phenyl]-4-( 3-hexyl-2,4-imidazolidinedion- 1-yl)benzenesulfonamide N-[4-[2-[[2-hydroxy-2-(3-pyfidinyl)ethyl]amino]ethyl]phenyl]-4-( 2,4-imidazolidinedion-1-yl)benzenesulfonamide N-[4-[2-[[2-hydroxy-2-(3-pyridinyl)ethyl]amino]ethyl]phenyl]-4-[3-( 3-cyclopentylpropyl)-2,4-imidazolidinedion-1-yl]benzenesulfonamide N-[4-[2-[[2-hydroxy-2-(3-pyfidinyl)ethyl]amino]ethyl]phenyl][1,2,4]-oxadiazol-5-yl)benzenesulfonamide N-[4-[2-[[2-hydroxy-2-(3-pyridinyl)ethyl]amino]ethyl]phenyl]-4-( 3-hexyl-[1,2,4]-oxadiazol-5-yl)benzenesulfonamide N-[4-[2-[[2-hydroxy-2-(3-pyfidinyl)ethyl]amino]ethyl]phenyl]-4-( 3-heptyl-[1,2,4]-oxadiazol-5-yl)benzenesulfonamide N-[4-[2-[[2-hydroxy-2-(3-pyridinyl)ethyl]amino]ethyl]phenyl]-4-( 3-octyl-[1,2,4]-oxadiazol-5-yl)benzenesulfonamide N-[4-[2-[[2-hydroxy-2-(3-pyfidinyl)ethyl]amino]ethyl]phenyl]-4-[3-( 2-cyclopentylethyl)-[1,2,4]-oxadiazol-5-yl]benzenesulfonamide N-[4-[ 2-[[2-hydroxy-2-(3-pyfidinyl)ethyl]amino]ethyl]phenyl]-4-[3-( 3-cyclopentylpropyl)-[1,2,4]-oxadiazol-5-yl]benzenesulfonamide N-[4-[2-[[2-hydroxy-2-(3-pyridinyl)ethyl]amino]ethyl]phenyl]-4-( 3-pentyl-[1,2,4]-thiadiazol-5-yl)benzenesulfonamide N-[4-[2-[[2-hydroxy-2-(3-pyfidinyl)ethyl]amino]ethyl]phenyl]-4-( 3-hexyl-[1,2,4]-thiadiazol-5-yl)benzenesulfonamide N-[4-[2-[[2-hydroxy-2-(3-pyridinyl)ethyl]amino]ethyl]phenyl]-4-( 3-heptyl-[1,2,4]-thiadiazol-5-yl)benzenesulfonamide N-[4-[2-[[2-hydroxy-2-(3-pyridinyl)ethyl]amino]ethyl]phenyl]-4-( 3-octyl-[1,2,4]-thiadiazol-5-yl)benzenesulfonamide N-[4-[2-[[2-hydroxy-2-(3-pyfidinyl)ethyl]amino]ethyl]phenyl]-4-[3-(2-cyclopentylethyl)-[1,2,4]-thiadiazol-5-yl]benzenesulfonamide N-[4-[2-[[2-hydroxy-2-(3-pyfidinyl)ethyl]amino]ethyl]phenyl]-4-[3-(3-cyclopentylpropyl)-[1,2,4]-thiadiazol-5-yl]benzenesulfonamide N-[4-[2-[[2-hydroxy-2-(3-pyridinyl)ethyl]amino]ethyl]phenyl]-4-( 5-pentyl-[1,2,4]-thiadiazol-3-yl)benzenesulfonamide N-[4-[2-[[2-hydroxy-2-(3-pyridinyl)ethyl]amino]ethyl]phenyl]-4-( 5-hexyl-[1,2,4]-thiadiazol-3-yl)benzenesulfonamide N-[4-[2-[[2-hydroxy-2-(3-pyridinyl)ethyl]amino]ethyl]phenyl]-4-( 5-heptyl-[1,2,4]-thiadiazol-3-yl)benzenesulfonamide N-[4-[2-[[2-hydroxy-2-(3-pyridinyl)ethyl]amino]ethyl]phenyl]-4-( 5-octyl-[1,2,4]-thiadiazol-3-yl)benzenesulfonamide N-[4-[2-[[2-hydroxy-2-(3-pyridinyl)ethyl]amino]ethyl]phenyl]-4-[5-( 2-cyclopentylethyl)-[1,2,4 ]-thiadiazol-3-yl]benzenesulfonamide N-[4-[2-[[2-hydroxy-2-(3-pyridinyl)ethyl]amino]ethyl]phenyl]-4-[ 5-( 3-cyclopentylpropyl)-[1,2,4]-thiadiazol-3-yl]benzenesulfonamide N-[4-[2-[[2-hydroxy-2-(3-pyridinyl)ethyl]amino]ethyl]phenyl]-4-( 4-pentyl-3-oxo-[1,2,4]-triazol-2-yl)benzenesulfonamide N-[4-[2-[[2-hydroxy-2-(3-pyridinyl)ethyl]amino]ethyl]phenyl]-4-( 4-hexyl-3-oxo-[1,2,4]-triazol-2-yl)benzenesulfonamide N-[4-[2-[[2-hydroxy-2-(3-pyridinyl)ethyl]amino]ethyl]phenyl]-4-( 4-heptyl-3-oxo-[1,2,4]-triazol-2-yl)benzenesulfonamide N-[4-[2-[[2-hydroxy-2-(3-pyridinyl)ethyl]amino]ethyl]phenyl]-4-(4-octyl- 3-oxo-[1,2,4]-triazol-2-yl)benzenesulfonamide N-[4-[2-[[2-hydroxy-2-(3-pyridinyl)ethyl]amino]ethyl]phenyl]-4-[4-( 2-cyclopentylethyl)-3-oxo-[1,2,4]-triazol-2-yl]benzenesulfonamide N-[4-[2-[[2-hydroxy-2-(3-pyridinyl)ethyl]amino]ethyl]phenyl]-4-[4-( 3-cyclopentylpropyl)-3-oxo-[ 1,2,4]-triazol-2-yl]benzenesulfonamide N-[4-[2-[[2-hydroxy-2-(3-pyridinyl)ethyl]amino]ethyl]phenyl]-4-( 5-pentyloxazol-2-yl)benzenesulfonamide N-[4-[2-[[2-hydroxy-2-(3-pyridinyl)ethyl]amino]ethyl]phenyl]-4-( 5-hexyloxazol-2-yl)benzenesulfonamide
N-[4-[2-[[2-hydroxy-2-(3-pyridinyl)ethyl]amino]ethyl]phenyl]-4-( 5-heptyloxazol-2-yl)benzenesulfonamide
N-[4-[2-[[2-hydroxy-2-(3-pyridinyl)ethyl]amino]ethyl]phenyl]-4-( 5-octyloxazol-2-yl)benzenesulfonamide
N-[4-[2-[[2-hydroxy-2-(3-pyridinyl)ethyl]amino]ethyl]phenyl]-4-[5-( 2-cyclopentylethyl)oxazol-2-yl]benzenesulfonamide
N-[4-[2-[[2-hydroxy-2-(3-pyridinyl)ethyl]amino]ethyl]phenyl]-4-[5-( 3-cyclopentylpropyl)oxazol-2-yl]benzenesulfonamide
N-[4-[2-[[2-hydroxy-2-(3-pyridinyl)ethyl]amino]ethyl]phenyl]-4-( 4-pentyloxazol-2-yl)benzenesulfonamide
N-[4-[2-[[2-hydroxy-2-(3-pyridinyl)ethyl]amino]ethyl]phenyl]-4-( 4-hexyloxazol-2-yl)benzenesulfonamide
N-[4-[2-[[2-hydroxy-2-(3-pyridinyl)ethyl]amino]ethyl]phenyl]-4-( 4-heptyloxazol-2-yl)benzenesulfonamide
N-[4-[2-[[2-hydroxy-2-(3-pyridinyl)ethyl]amino]ethyl]phenyl]-4-( 4-octyloxazol-2-yl)benzenesulfonamide
N-[4-[ 2-[[ 2-hydroxy-2-(3-pyridinyl)ethyl]amino]ethyl]phenyl]-4-[4-( 2-cyclopentylethyl)oxazol-2-yl]benzenesulfonamide
N-[4-[ 2-[[ 2-hydroxy-2-(3-pyridinyl)ethyl]amino]ethyl]phenyl]-4-[4-( 3-cyclopentylpropyl)oxazol-2-yl]benzenesulfonamide
N-[4-[2-[[2-hydroxy-2-(3-pyridinyl)ethyl]amino]ethyl]phenyl]-4-( 2-hexyloxazol-5-yl)benzenesulfonamide
N-[4-[2-[[2-hydroxy-2-(3-pyridinyl)ethyl]amino]ethyl]phenyl]-4-( 2-heptyloxazol-5-yl)benzenesulfonamide
N-[4-[2-[[2-hydroxy-2-(3-pyridinyl)ethyl]amino]ethyl]phenyl]-4-[2-( 3-cyclopentylpropyl)oxazol-5-yl]benzenesulfonamide
N-[4-[2-[[2-hydroxy-2-(3-pyridinyl)ethyl]amino]ethyl]phenyl]-4-[2-( 4-cyclohexylbutyl)oxazol-5-yl]benzenesulfonamide
N-[4-[2-[[2-hydroxy-2-(3-pyridinyl)ethyl]amino]ethyl]phenyl]-4-[2-[2-(4-fluorophenyl)ethyl]oxazol-5-yl]benzenesulfonamide
N-[4-[2-[[2-hydroxy-2-(3-pyridinyl)ethyl]amino]ethyl]phenyl]-4-( 2-pentyloxazol-4-yl)benzenesulfonamide
N-[4-[2-[[2-hydroxy-2-(3-pyridinyl)ethyl]amino]ethyl]phenyl]-4-( 2-hexyloxazol-4-yl)benzenesulfonamide
N-[4-[2-[[2-hydroxy-2-(3-pyridinyl)ethyl]amino]ethyl]phenyl]-4-( 2-heptyloxazol-4-yl)benzenesulfonamide
N-[4-[2-[[2-hydroxy-2-(3-pyridinyl)ethyl]amino]ethyl]phenyl]-4-( 2-octyloxazol-4-yl)benzenesulfonamide
N-[4-[2-[[2-hydroxy-2-(3-pyridinyl)ethyl]amino]ethyl]phenyl]-4-[2-( 2-cyclopentylethyl)oxazol-4-yl]benzenesulfonamide
N-[4-[2-[[2-hydroxy-2-(3-pyridinyl)ethyl]amino]ethyl]phenyl]-4-[2-( 3-cyclopentylpropyl)oxazol-4-yl]benzenesulfonamide
N-[4-[2-[[2-hydroxy-2-(3-pyridinyl)ethyl]amino]ethyl]phenyl]-4-( 5-pentylthiazol-2-yl)benzenesulfonamide
N-[4-[2-[[2-hydroxy-2-(3-pyridinyl)ethyl]amino]ethyl]phenyl]-4-( 5-hexylthiazol-2-yl)benzenesulfonamide
N-[4-[2-[[2-hydroxy-2-(3-pyridinyl)ethyl]amino]ethyl]phenyl]-4-( 5-heptylthiazol-2-yl)benzenesulfonamide
N-[4-[2-[[2-hydroxy-2-(3-pyridinyl)ethyl]amino]ethyl]phenyl]-4-( 5-octylthiazol-2-yl)benzenesulfonamide
N-[4-[2-[[2-hydroxy-2-(3-pyridinyl)ethyl]amino]ethyl]phenyl]-4-[5-( 2-cyclopentylethyl)thiazol-2-yl]benzenesulfonamide
N-[4-[2-[[2-hydroxy-2-(3-pyridinyl)ethyl]amino]ethyl]phenyl]-4-[5-( 3-cyclopentylpropyl)thiazol-2-yl]benzenesulfonamide
N-[4-[2-[[2-hydroxy-2-(3-pyridinyl)ethyl]amino]ethyl]phenyl]-4-( 4-pentylthiazol-2-yl)benzenesulfonamide
N-[4-[2-[[2-hydroxy-2-(3-pyridinyl)ethyl]amino]ethyl]phenyl]-4-( 4-hexylthiazol-2-yl)benzenesulfonamide
N-[4-[2-[[2-hydroxy-2-(3-pyridinyl)ethyl]amino]ethyl]phenyl]-4-( 4-heptylthiazol-2-yl)benzenesulfonamide
N-[4-[2-[[2-hydroxy-2-(3-pyridinyl)ethyl]amino]ethyl]phenyl]-4-( 4-octylthiazol-2-yl)benzenesulfonamide
N-[4-[2-[[2-hydroxy-2-(3-pyridinyl)ethyl]amino]ethyl]phenyl]-4-[4-( 2-cyclopentylethyl)thiazol-2-yl]benzenesulfonamide
N-[4-[2-[[2-hydroxy-2-(3-pyridinyl)ethyl]amino]ethyl]phenyl]-4-[4-( 3-cyclopentylpropyl)thiazol-2-yl]benzenesulfonamide
N-[4-[2-[[2-hydroxy-2-(3-pyridinyl)ethyl]amino]ethyl]phenyl]-4-( 2-pentylthiazol-4-yl)benzenesulfonamide
N-[4-[2-[[2-hydroxy-2-(3-pyridinyl)ethyl]amino]ethyl]phenyl]-4-( 2-hexylthiazol-4-yl)benzenesulfonamide
N-[4-[2-[[2-hydroxy-2-(3-pyridinyl)ethyl]amino]ethyl]phenyl]-4-( 2-heptylthiazol-4-yl)benzenesulfonamide
N-[4-[2-[[2-hydroxy-2-(3-pyridinyl)ethyl]amino]ethyl]phenyl]-4-( 2octylthiazol-4-yl)benzenesulfonamide
N-[4-[2-[[2-hydroxy-2-(3-pyridinyl)ethyl]amino]ethyl]phenyl]-4-[2-( 2-cyclopentylethyl)thiazol-4-yl]benzenesulfonamide
N-[4-[2-[[2-hydroxy-2-(3-pyridinyl)ethyl]amino]ethyl]phenyl]-4-[2-( 3-cyclopentylpropyl)thiazol-4-yl]benzenesulfonamide
N-[4-[2-[[2-hydroxy-2-(3-pyridinyl)ethyl]amino]ethyl]phenyl]-4-( 2-pentylthiazol-5-yl)benzenesulfonamide
N-[4-[2-[[2-hydroxy-2-(3-pyridinyl)ethyl]amino]ethyl]phenyl]-4-( 2-hexylthiazol-5-yl)benzenesulfonamide
N-[4-[2-[[2-hydroxy-2-(3-pyridinyl)ethyl]amino]ethyl]phenyl]-4-( 2-heptylthiazol-5-yl)benzenesulfonamide
N-[4-[2-[[2-hydroxy-2-(3-pyridinyl)ethyl]amino]ethyl]phenyl]-4-( 2-octylthiazol-5-yl)benzenesulfonamide
N-[4-[2-[[2-hydroxy-2-(3-pyridinyl)ethyl]amino]ethyl]phenyl]-4-[2-( 2-cyclopentylethyl)thiazol-5-yl]benzenesulfonamide
N-[4-[2-[[2-hydroxy-2-(3-pyridinyl)ethyl]amino]ethyl]phenyl]-4-[2-( 3-cyclopentylpropyl)thiazol-5-yl]benzenesulfonamide
N-[4-[2-[[2-hydroxy-2-(3-pyridinyl)ethyl]amino]ethyl]phenyl]- 1-( 5-methylthiazol-2-yl)-5-indolinesulfonamide
N-[4-[2-[[2-hydroxy-2-(3-pyridinyl)ethyl]amino]ethyl]phenyl]-1-( 5-pentylthiazol-2-yl)-5-indolinesulfonamide
N-[4-[2-[[2-hydroxy-2-(3-pyridinyl)ethyl]amino]ethyl]phenyl]-1-( 5-hexylthiazol-2-yl)-5-indolinesulfonamide
N-[4-[2-[[2-hydroxy-2-(3-pyridinyl)ethyl]amino]ethyl]phenyl]-1-( 5-heptylthiazol-2-yl)-5-indolinesulfonamide
N-[4-[2-[[2-hydroxy-2-(3-pyridinyl)ethyl]amino]ethyl]phenyl]-1-( 5-octylthiazol-2-yl)-5-indolinesulfonamide
N-[4-[2-[[2-hydroxy-2-(3-pyridinyl)ethyl]amino]ethyl]phenyl]-1-[5-( 2-cyclopentylethyl)thiazol-2-yl]-5-indolinesulfonamide
N-[4-[2-[[2-hydroxy-2-(3-pyridinyl)ethyl]amino]ethyl]phenyl]-1-[5-( 3-cyclopentylpropyl)thiazol-2-yl]-5-indolinesulfonamide
N-[4-[2-[[2-hydroxy-2-(3-pyridinyl)ethyl]amino]ethyl]phenyl]-1-( 4-pentylthiazol-2-yl)-5-indolinesulfonamide
N-[4-[2-[[2-hydroxy-2-(3-pyridinyl)ethyl]amino]ethyl]phenyl]-1-( 4-hexylthiazol-2-yl)-5-indolinesulfonamide
N-[4-[2-[[2-hydroxy-2-(3-pyridinyl)ethyl]amino]ethyl]phenyl]-1-( 4-heptylthiazol-2-yl)-5-indolinesulfonamide
N-[4-[2-[[2-hydroxy-2-(3-pyridinyl)ethyl]amino]ethyl]phenyl]-1-[4-(2-cyclopentylethyl)thiazol-2-yl]-5-indolinesulfonamide N-[4-[2-[[2-hydroxy-2-(3-pyridinyl)ethyl]amino]ethyl]phenyl]-1-[4-( 3-cyclopentylpropyl)thiazol-2-yl]-5-indolinesulfonamide
N-[4-[2-[[2-hydroxy-2-(3-pyridinyl)ethyl]amino]ethyl]phenyl]-1-( 5-methyloxazol-2-yl)-5-indolinesulfonamide
N-[4-[2-[[2-hydroxy-2-(3-pyridinyl)ethyl]amino]ethyl]phenyl]-1-( 5-pentyloxazol-2-yl)-5-indolinesulfonamide
N-[4-[2-[[2-hydroxy-2-(3-pyridinyl)ethyl]amino]ethyl]phenyl]-1-( 5-hexyloxazol-2-yl)-5-indolinesulfonamide
N-[4-[2-[[2-hydroxy-2-(3-pyridinyl)ethyl]amino]ethyl]phenyl]-1-( 5-heptyloxazol-2-yl)-5-indolinesulfonamide
N-[4-[2-[[2-hydroxy-2-(3-pyridinyl)ethyl]amino]ethyl]phenyl]-1-( 5-octyloxazol-2-yl)-5-indolinesulfonamide
N-[4-[2-[[2-hydroxy-2-(3-pyridinyl)ethyl]amino]ethyl]phenyl]-1-[5-( 2-cyclopentylethyl)oxazol-2-yl]-5-indolinesulfonamide
N-[4-[2-[[2-hydroxy-2-(3-pyridinyl)ethyl]amino]ethyl]phenyl]-1-[5-( 3-cyclopentylpropyl)oxazol-2-yl]-5-indolinesulfonamide
N-[4-[2-[[2-hydroxy-2-(3-pyridinyl)ethyl]amino]ethyl]phenyl]-1-( 4-methyloxazol-2-yl)-5-indolinesulfonamide
N-[4-[2-[[2-hydroxy-2-(3-pyridinyl)ethyl]amino]ethyl]phenyl]-1-( 4-pentyloxazol-2-yl)-5-indolinesulfonamide
N-[4-[2-[[2-hydroxy-2-(3-pyridinyl)ethyl]amino]ethyl]phenyl]-1-( 4-hexyloxazol-2-yl)-5-indolinesulfonamide
N-[4-[2-[[2-hydroxy-2-(3-pyridinyl)ethyl]amino]ethyl]phenyl]-1-( 4-heptyloxazol-2-yl)-5-indolinesulfonamide
N-[4-[2-[[2-hydroxy-2-(3-pyridinyl)ethyl]amino]ethyl]phenyl]-1-( 4-octyloxazol-2-yl)-5-indolinesulfonamide
N-[4-[2-[[2-hydroxy-2-(3-pyridinyl)ethyl]amino]ethyl]phenyl]-1-[4-( 2-cyclopentylethyl)oxazol-2-yl]-5-indolinesulfonamide
N-[4-[2-[[2-hydroxy-2-(3-pyridinyl)ethyl]amino]ethyl]phenyl]-1-[4-( 3-cyclopentylpropyl)oxazol-2-yl]-5-indolinesulfonamide
N-[4-[2-[[2-hydroxy-2-(3-pyridinyl)ethyl]amino]ethyl]phenyl]-1-( 3-methyl-[1,2,4]-oxadiazol-5-yl)-5-indolinesulfonamide
N-[4-[2-[[2-hydroxy-2-(3-pyridinyl)ethyl]amino]ethyl]phenyl]-1-( 3-pentyl-[1,2,4]-oxadiazol-5-yl)-5-indolinesulfonamide
N-[4-[2-[[2-hydroxy-2-(3-pyridinyl)ethyl]amino]ethyl]phenyl]-1-( 3-hexyl-[1,2,4]-oxadiazol-5-yl)-5-indolinesulfonamide
N-[4-[2-[[2-hydroxy-2-(3-pyridinyl)ethyl]amino]ethyl]phenyl]-1-( 3-heptyl-[1,2,4]-oxadiazol-5-yl)-5-indolinesulfonamide
N-[4-[2-[[2-hydroxy-2-(3-pyridinyl)ethyl]amino]ethyl]phenyl]-1-( 3-octyl-[1,2,4]-oxadiazol-5-yl)-5-indolinesulfonamide
N-[4-[2-[[2-hydroxy-2-(3-pyridinyl)ethyl]amino]ethyl]phenyl]-1-[3-( 2-cyclopentylethyl)-[1,2,4]-oxadiazol-5-yl]-5-indolinesulfonamide
N-[4-[2-[[2-hydroxy-2-(3-pyridinyl)ethyl]amino]ethyl]phenyl]-1-[3-( 3-cyclopentylpropyl)-[1,2,4]-oxadiazol-5-yl]-5-indolinesulfonamide
N-[4-[2-[[2-hydroxy-2-(3-pyridinyl)ethyl]amino]ethyl]phenyl]-1-( 5-methyl-[1,2,4]-oxadiazol-3-yl)-5-indolinesulfonamide
N-[4-[2-[[2-hydroxy-2-(3-pyridinyl)ethyl]amino]ethyl]phenyl]-1-( 5-pentyl-[1,2,4]-oxadiazol-3-yl)-5-indolinesulfonamide
N-[4-[2-[[2-hydroxy-2-(3-pyridinyl)ethyl]amino]ethyl]phenyl]-1-( 5-hexyl-[1,2,4]-oxadiazol-3-yl)- 5-indolinesulfonamide
N-[4-[2-[[2-hydroxy-2-(3-pyridinyl)ethyl]amino]ethyl]phenyl]-1-( 5-heptyl-[1,2,4]-oxadiazol-3-yl)-5-indolinesulfonamide
N-[4-[2-[[2-hydroxy-2-(3-pyridinyl)ethyl]amino]ethyl]phenyl]-1-( 5-octyl-[1,2,4]-oxadiazol-5-yl)-3-indolinesulfonamide
N-[4-[2-[[2-hydroxy-2-(3-pyridinyl)ethyl]amino]ethyl]phenyl]-1-[5-( 2-cyclopentylethyl)-[1,2,4]-oxadiazol-3-yl]-5-indolinesulfonamide
N-[4-[2-[[2-hydroxy-2-(3-pyridinyl)ethyl]amino]ethyl]phenyl]-1-[5-( 3-cyclopentylpropyl)-[1,2,4]-oxadiazol-3-yl]-5-indolinesulfonamide
N-[4-[2-[[2-hydroxy-2-(3-pyridinyl)ethyl]amino]ethyl]phenyl]-4-[2-(cyclopentylmethyl)oxazol-5-yl]benzenesulfonamide
N-[4-[2-[[2-hydroxy-2-(3-pyridinyl)ethyl]amino]ethyl]phenyl]-4-( 4-diphenylhydroxymethyl-5-methyl-[1,2,3]-triazol-2-yl)benzenesulfonamide
N-[4-[2-[[2-hydroxy-2-(3-pyridinyl)ethyl]amino]ethyl]phenyl]-4-[4-[bis( 4-fluorophenyl)hydroxymethyl]-5-methyl-[1,2,3]-triazol- 2-yl]benzenesulfonamide
N-[4-[2-[[2-hydroxy-2-(3-pyridinyl)ethyl]amino]ethyl]phenyl]-4-( 3-hexylpyrazol-1-yl)benzenesulfonamide
N-[4-[2-[[2-hydroxy-2-(3-pyridinyl)ethyl]amino]ethyl]phenyl]-4-[5-( 1-hydroxypentyl)-[1,2,4]-oxadiazol-3-yl]benzenesulfonamide
N-[4-[2-[[ 2-hydroxy-2-(3-pyridinyl)ethyl]amino]ethyl]phenyl]-4-[4-[( 4-fluorophenyl)hydroxymethyl]-5-methyl-[1,2,3]-triazol- 2-yl]benzenesulfonamide
N-[4-[2-[[2-hydroxy-2-(3-pyridinyl)ethyl]amino]ethyl]phenyl]-4-( 2-pentyltetrazol-5-yl)benzenesulfonamide
N-[4-[2-[[2-hydroxy-2-(3-pyridinyl)ethyl]amino]ethyl]phenyl]-4-( 2-hexyltetrazol-5-yl)benzenesulfonamide
N-[4-[2-[[2-hydroxy-2-(3-pyridinyl)ethyl]amino]ethyl]phenyl]-4-( 2-heptyltetrazol-5-yl)benzenesulfonamide
N-[4-[2-[[2-hydroxy-2-(3-pyridinyl)ethyl]amino]ethyl]phenyl]-4-( 2-octyltetrazol-5-yl)benzenesulfonamide
N-[4-[2-[[2-hydroxy-2-(3-pyridinyl)ethyl]amino]ethyl]phenyl]-4-[2-( 2-cyclopentylethyl)tetrazol-5-yl]benzenesulfonamide
N-[4-[2-[[2-hydroxy-2-(3-pyridinyl)ethyl]amino]ethyl]phenyl]-4-[2-( 3-cyclopentylpropyl)tetrazol-5-yl]benzenesulfonamide
N-[4-[2-[[2-hydroxy-2-(3-pyridinyl)ethyl]amino]ethyl]phenyl]-4-( 5-pentyltetrazol-2-yl)benzenesulfonamide
N-[4-[2-[[2-hydroxy-2-(3-pyridinyl)ethyl]amino]ethyl]phenyl]-4-( 5-hexyltetrazol-2-yl)benzenesulfonamide
N-[4-[2-[[2-hydroxy-2-(3-pyridinyl)ethyl]amino]ethyl]phenyl]-4-( 5-heptyltetrazol-2-yl)benzenesulfonamide
N-[4-[2-[[2-hydroxy-2-(3-pyridinyl)ethyl]amino]ethyl]phenyl]-4-( 5-octyltetrazol-2-yl)benzenesulfonamide
N-[4-[2-[[2-hydroxy-2-(3-pyridinyl)ethyl]amino]ethyl]phenyl]-4-[5-( 2-cyclopentylethyl)tetrazolo2-yl]benzenesulfonamide
N-[4-[2-[[2-hydroxy-2-(3-pyridinyl)ethyl]amino]ethyl]phenyl]-4-[5-( 3-cyclopentylpropyl)tetrazol-2-yl]benzenesulfonamide.

The compounds of the instant invention all have at least one asymmetric center as noted by the asterisk in structural Formula I. Additional asymmetric centers may be present on the molecule depending upon the nature of the various substituents on the molecule, in particular, $R^2$ and $R^3$. Each such asymmetric center will produce two optical isomers and it is intended that all such optical isomers, as separated, pure or partially purified optical isomers or racemic mixtures thereof, be included within the ambit of the instant invention. In the case of the asymmetric center represented by the asterisk in Formula I, it has been found that the compound in which the hydroxy substituent is above the plane of the structure, as seen in Formula Ic, is more active and thus more preferred over the compound in which the hydroxy substituent is below the plane of the structure.

The following stereospecific structure represents the preferred stereoisomers of the instant invention:

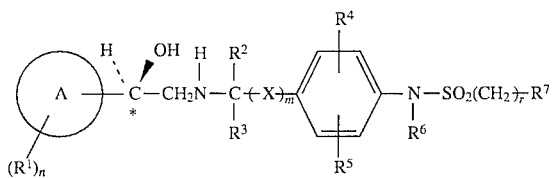

where n, m, r, A, $R^1$, $R^2$, $R^3$, $R^4$, $R^5$, $R^6$, $R^7$ and X are as defined above under formula I.

Throughout the instant application, the following terms have the indicated meanings:

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The alkoxy groups specified above are intended to include those alkoxy groups of the designated length in either a straight or branched configuration. Exemplary of such alkoxy groups are methoxy, ethoxy, propoxy, isopropoxy, butoxy, isobutoxy, tertiary butoxy, pentoxy, isopentoxy, hexoxy, isohexoxy and the like.

The term "halogen" is intended to include the halogen atoms fluorine, chlorine, bromine and iodine.

Examples of 5 and 6-membered heterocycles and fused heterocycles of A, Z and $R^{1a}$ include pyridyl, quinolinyl, pyrimidinyl, pyrrolyl, thienyl, imidazolyl, thiazolyl, benzimidazolyl, thiadiazolyl, benzothiadiazolyl, indolyl, indolinyl, benzodioxolyl, benzodioxanyl, benzothiophenyl, benzofuranyl, benzoxazinyl, benzisoxazolyl, benzothiazolyl, tetrahydronaphthyl, dihydrobenzofuranyl, tetrahydroquinolinyl, furopyridine and thienopyridine.

The preferred values of A and Z are phenyl, naphthyl, benzene ring fused to a 5 or 6-membered heterocyclic ring with from 1 to 4 heteroatoms selected from oxygen, sulfur and nitrogen, or heterocycles with from 1 to 4 heteroatoms independently selected from one of oxygen or sulfur, and/or 1 to 4 nitrogen atoms.

The more preferred values of A are phenyl, pyridyl, quinolinyl, pyrimidinyl, pyrrolyl, thienyl, imidazolyl, and thiazolyl.

The more preferred values of Z are phenyl, naphthyl, quinolinyl, thienyl, benzimidazolyl, thiadiazolyl, benzothiadiazolyl, indolyl, indolinyl, benzodioxolyl, benzodioxanyl, benzothiophenyl, benzofuranyl, benzoxazinyl, benzisoxazolyl, benzothiazolyl, tetrahydronaphthyl, dihydrobenzofuranyl, triazolyl, tetrazolyl, oxadiazolyl, imidazolyl, oxazolyl, thiazolyl, imidazolidinyl, pyrazolyl, isoxazolyl, pyridyl, pyrimidyl, pyrazolyl, tetrahydrobenzothiazolyl and tetrahydroquinolinyl. When Z is attached to $-NSO_2(CH_2)_r-$, it is preferably phenyl, naphthyl or a benzene ring fused to a 5 or 6-membered heterocyclic ring with from 1 to 4 heteroatoms selected from oxygen, sulfur and nitrogen. When Z is part of the definition of R8, it is preferably phenyl, a 5 or 6-membered heterocyclic ring with from 1 to 4 heteroatoms selected from oxygen, sulfur and nitrogen, a benzene ring fused to a 5 or 6-membered heterocyclic ring with from 1 to 4 heteroatoms selected from oxygen, sulfur and nitrogen, or a 5 or 6-membered heterocyclic ring with from 1 to 4 heteroatoms selected from oxygen, sulfur and nitrogen fused to a $C_3-C_8$ cycloalkyl ring.

The preferred heterocycles of $R^{1a}$ are thienyl, thiadiazolyl, triazolyl, tetrazolyl, oxadiazolyl, imidazolyl, oxazolyl, thiazolyl, imidazolidinyl, isoxazolyl, pyridyl, pyrimidyl, and pyrazolyl.

Certain of the above defined terms may occur more than once in the above formula and upon such occurrence each term shall be defined independently of the other; thus for example, $NR^8R^8$ may represent $NH_2$, $NHCH_3$, $N(CH_3)CH_2CH_3$, and the like.

The following abbreviations are used throughout the specification:

Boc :tert-butyloxycarbonyl

Cbz :carbobenzyloxy

DIP-Cl :diisopinocampheylchloroborane

DMF :dimethylformamide

DMSO :dimethylsulfoxide

HPLC :high pressure liquid chromatography

Me :methyl

MPLC :medium pressure liquid chromatography

Ms :methanesulfonyl (mesyl)

NBS :N-bromosuccinimide

NCS :N-chlorosuccinimide nHex :n-hexyl

TB AF :tetrabutylammonium fluoride

TBS (TBDMS) :t-butyldimethylsilyl

TFA :trifluoroacetic acid

THF :tetrahydrofuran

The compounds (I) of the present invention can be prepared from epoxide intermediates such as those of formula II and amine intermediates such as those of formula III. The preparation of these intermediates is described in the following schemes.

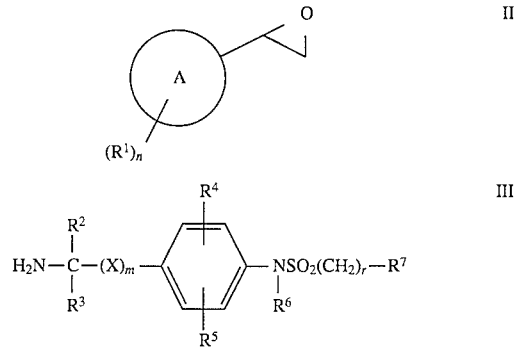

where n, m, r, A, $R^1$, $R^2$, $R^3$, $R^4$, $R^5$, $R^6$, $R^7$ and X are as defined above.

Compounds II are known in the literature or may be conveniently prepared by a variety of methods familiar to those skilled in the art. One common route is illustrated in Scheme 1. Acid chloride 1, which may be commercially available or readily prepared from the corresponding acid by treatment with, for example, thionyl chloride or oxalyl chloride, is treated with diazomethane in a solvent such as diethyl ether. The resultant diazoketone is then treated with hydrogen chloride to give chloroketone 2 (X=Cl). The haloketone 2 is then reduced with a reducing agent such as sodium borohydride. The resultant alcohol 3 is treated with base such as potassium carbonate in refluxing acetone to provide the desired epoxide II. The enantiomerically enriched (R) and (S) epoxides II are readily available by asymmetric reduction of haloketones 2 using chiral reducing agents such as (−) or (+)-DIP-Cl, (R) or (S)-Alpine borane or (R) or (S)-tetrahydro-1-methyl-3,3-diphenyl-1H, 3H-pyrrolo[1,2-c][1,3,2]oxazaborole-borane ((R) or (S)-

OAB·BH$_3$).

SCHEME 1

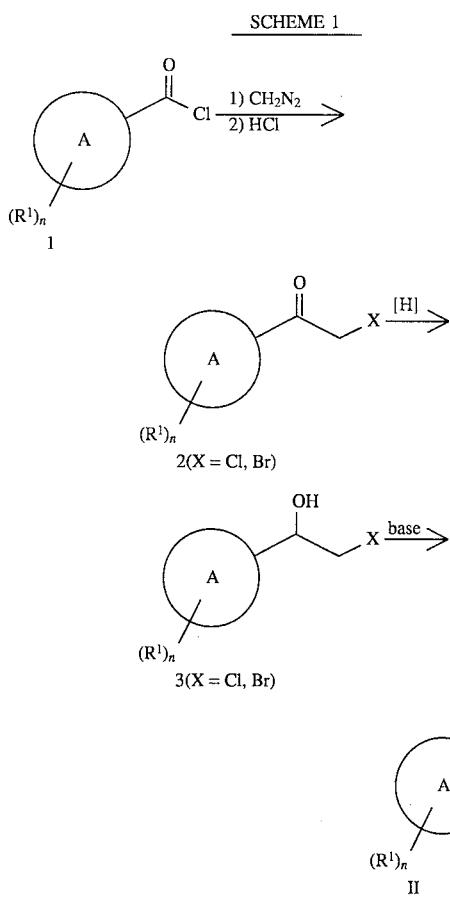

An alternate route to the desired haloketones 2 is illustrated in Scheme 2. Methylketone 4 may be converted to the corresponding haloketone using a variety of reagents known to those in the art and summarized in Larock Comprehensive Organic Transformations; VCH: New York, 1989, 369–372. Conveniently, methylketone 4 is treated with chlorine or N-chlorosuccinimide in acetic acid with an additional acid source such as hydrogen chloride or aluminum chloride. For the synthesis of 2 (X=Br), bromine, dibromobarbituric acid or NBS with hydrogen bromide or aluminum bromide may be used. In some cases, the chloro or bromoketones 2 may be commercially available.

SCHEME 2

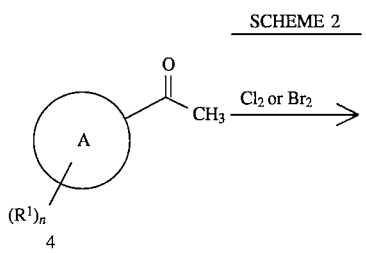

SCHEME 2 -continued

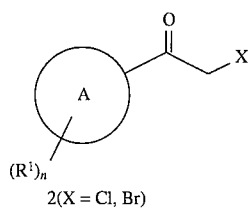

Many of the methylketones 4 are commercially available or readily prepared by methods described in the literature and known to those skilled in the art. $R^1$ substituents on the acid chlorides 1 or methylketones 4 may need to be protected during the subsequent procedures. A description of such protecting groups may be found in: *Protective Groups in Organic Synthesis,* 2nd Ed., T. W. Greene and P. G. M. Wuts, John Wiley and Sons, New York, 1991.

Compounds III can be conveniently prepared by a variety of methods familiar to those skilled in the art. A convenient route for their preparation when $R^6$ is hydrogen is illustrated in Scheme 3. Compound 5 is selectively protected as a suitable carbamate derivative 6 with, for example, di-tert-butyl dicarbonate or carbobenzyloxy chloride. This compound is then treated with a sulfonyl halide, preferably the sulfonyl chloride 7, and a base such as pyridine in an anhydrous solvent such as dichloromethane or chloroform for 0.5 to 24 hours at temperatures of −20° to 50° C., preferably 0° C., to provide the sulfonamide 8. The protecting group is then removed with, for example, trifluoracetic acid in the case of Boc or catalytic hydrogenation in the case of Cbz, to give the desired amine 9.

SCHEME 3

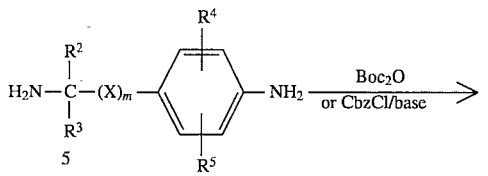

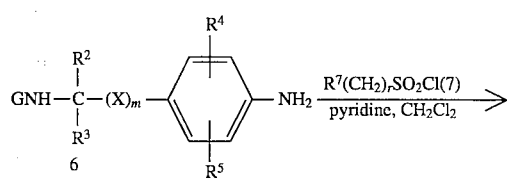

G = Boc or Cbz

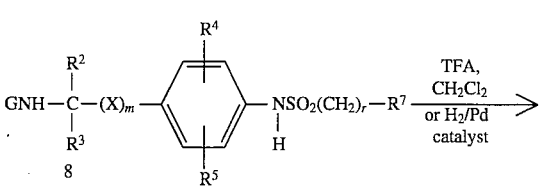

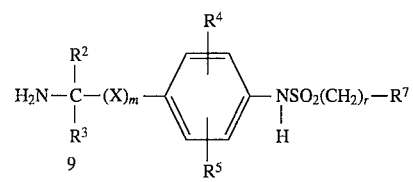

Compounds III where $R^6$ is not hydrogen may be conveniently prepared as illustrated in Scheme 4. Sulfonamide 8, prepared as described above, is alkylated with an appropriate alkylating agent 10 in the presence of base to provide sulfonamide 11. Removal of the protecting group as above gives the desired compound 9a.

SCHEME 4

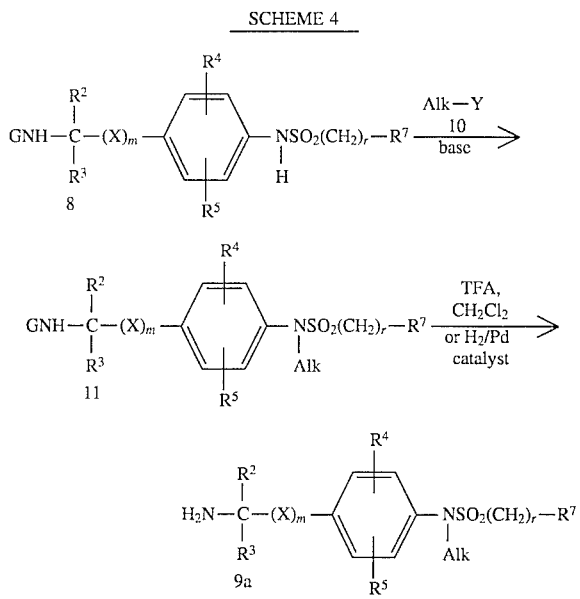

G = Boc or Cbz
Y = Cl, Br, or I
Alk = $C_1$–$C_6$ alkyl

The sulfonyl chlorides 7, many of which are commercially available, can also be readily prepared by a number of methods familiar to those skilled in the art. One suitable method involves the addition of an organolithium reagent or a Grignard reagent to sulfuryl chloride following the procedure of S. N. Bhattacharya, et. al., J. Chem. Soc. (C), 1265–1267 (1969). Another convenient method involves the treatment of a thiol with sulfuryl chloride and a metal nitrate according to the procedure of Y. J. Park, et. al., Chemistry Letters, 1483–1486 (1992). Sulfonic acids are also conveniently converted to the corresponding sulfonyl chloride by treatment with $PCl_5$, $PCl_3$ or $SOCl_2$ (J. March, *Advanced Organic Chemistry*, 4th Ed., John Wiley and Sons, New York: 1992, p 1297 and references cited therein). Aromatic and heteroaromatic compounds may be chlorosulfonylated directly by treatment with Vilsmeier's reagent or chorosulfonic acid (Organic Synthesis, I, 8).

The diamines 5 are commercially available or readily prepared by methods described in the literature or known to those skilled in the art. Compound 5 where $R^2$ or $R^3$ is methyl can be prepared from the corresponding amino acid following the method of J. D. Bloom, et. al., J. Med. Chem., 35, 3081–3084 (1992). As illustrated in Scheme 5 for $R^3$=methyl, the appropriate (R) amino acid 12 is esterified, conveniently by treatment with methanolic hydrochloric acid, and then treated with di-tert-butyl dicarbonate to give compound 13. The ester group is reduced with a hydride source such as lithium borohydride and the resultant alcohol is converted to a leaving group such as a mesylate. Removal of the Boc protecting groups gives diamine 14. This compound is subjected to catalytic hydrogenation in the presence of base such as sodium acetate to give the desired α-methyl amine 15. The other enantiomer is available through an analogous sequence starting with the corresponding (S) amino acid.

SCHEME 5

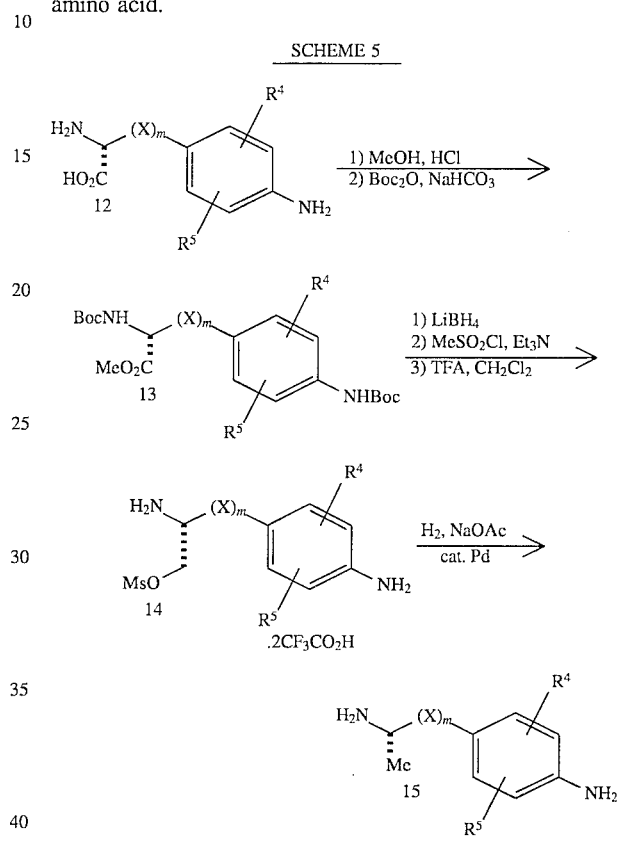

Diamines 5 or sulfonamide amines 9 where X is —$CH_2O$— and m is 1 are also readily prepared by methods described in the literature or known to those skilled in the art. For example, as shown in Scheme 6, the sodium salt of 4-nitrophenol 16 is alkylated with 1-bromo-2-chloroethane, conveninetly in refluxing 2-butanone with a base such as potassium carbonate to give chloro derivative 17. The chloride is converted to the corresponding amine by treatment with lithium azide followed by reduction with, for example, triphenylphosphine in aqueous tetrahydrofuran. Protection of the resultant amine, conveniently as its t-butyl carbamate by treatment with di-tertobutyldicarbonate, gives derivative 18. The nitro group is then reduced, for example, by catalytic hydrogenation to provide amine 19. Acylation of intermediate 19 with sulfonyl chloride 7, followed by deprotection with acid such as trifluoroacetic acid gives the desired intermediate 20.

SCHEME 6

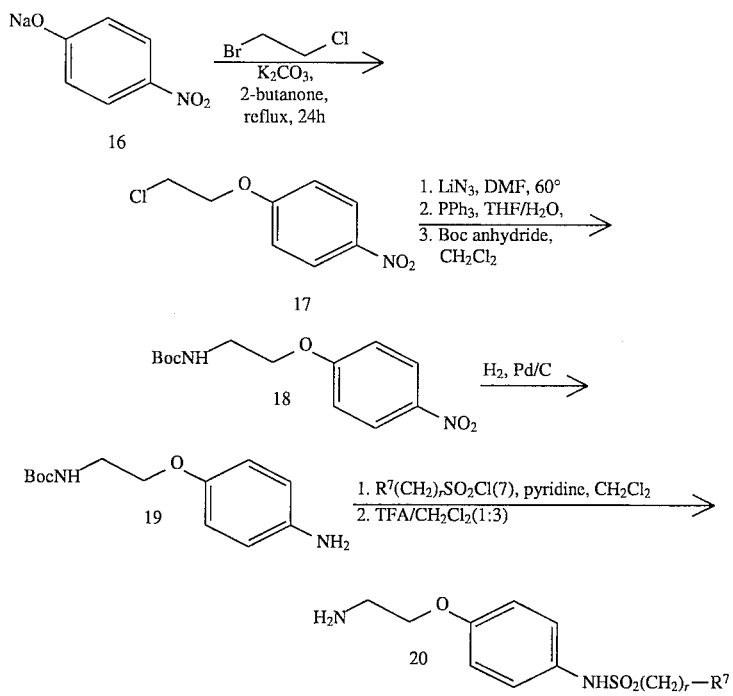

Alternatively, diamine 5 where X is —CH$_2$O— and m is 1 is available from intermediate 19 by treatment with trifluoroacetic acid. This diamine may then be modified as illustrated in Scheme 3.

Diamines 5 and sulfonamide amines 9 where X is —CH$_2$CH$_2$— and m is 1 are also readily prepared by methods described in the literature or known to those skilled in the art. For example, as shown in Scheme 7, bromo derivative 21 is treated with sodium cyanide to provide nitrile 22. The nitro group is selectively reduced by treatment with hydrogen and catalytic palladium to provide amine 23. Amine 23 is acylated with sulfonyl chloride 7 to give the corresponding sulfonamide 24. Reduction of compound 24 with cobalt chloride and sodium borohydride provides the desired amine 25.

SCHEME 7

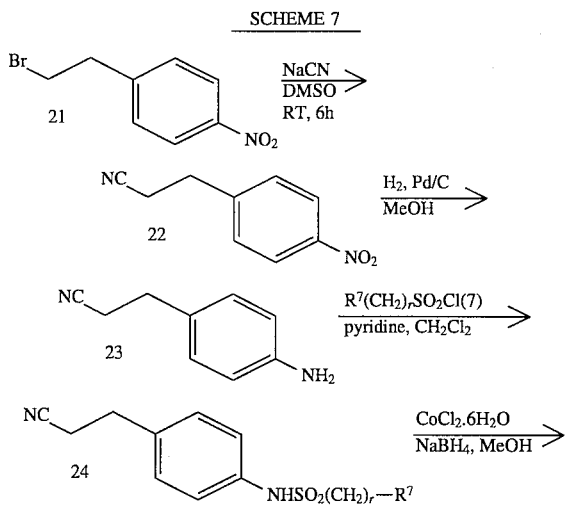

-continued
SCHEME 7

Alternatively, diamine 5 where X is —CH$_2$CH$_2$— and m is 1 is available from intermediate 23 by reduction of the nitrile group with, for example, cobalt chloride and sodium borohydride. This diamine may then be modified as illustrated in Scheme 3.

Intermediates II and III are coupled by heating them neat or as a solution in a polar solvent such as methanol, acetonitrile, tetrahydrofuran, dimethylsulfoxide or N-methyl pyrrolidinone for 1 to 24 hours at temperatures of 30° to 150° C. to provide compounds I as shown in Scheme 8. The reaction is conveniently conducted in refluxing methanol. Alternatively, a salt of amine III, such as the trifluoroacetate or hydrochloride salt, may be used. In these cases, a base such as sodium bicarbonate or diethylisopropylamine is added to the reaction mixture. The product is purified from unwanted side products by recrystallization, trituration, preparative thin layer chromatography, flash chromatography on silica gel as described by W. C. Still, et. al., J. Org. Chem. 43, 2923 (1978), medium pressure liquid chromatography, or HPLC. Compounds which are purified by HPLC may be isolated as the corresponding salt. Purification of intermediates is achieved in the same manner.

SCHEME 8

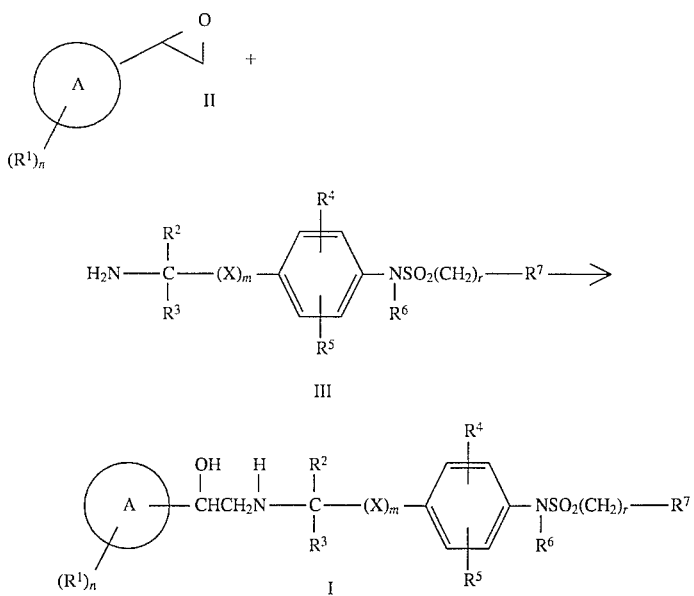

In some cases, the coupling product I from the reaction described in Scheme 8 may be further modified, for example, by the removal of protecting groups or the manipulation of substituents on, in particular, R¹ and R⁷. These manipulations may include, but are not limited to, reduction, oxidation, alkylation, acylation, and hydrolysis reactions which are commonly known to those skilled in the art.

An alternate method for the synthesis of compound I is illustrated in Scheme 9. Epoxide II is coupled to amine 5 as described above for coupling intermediates II and III (Scheme 8) to give aniline derivative 27. The secondary amine is selectively protected, for example, as a carbamate by treatment with di-tert-butyldicarbonate to provide carbamate 29. Alternatively, nitro amine 26 is used in the coupling reaction to provide 28. Following protection as described above, the nitro group is reduced, for example, by catalytic hydrogenation with palladium catalyst or raney nickel, to provide intermediate 29. In some cases, other group may be reduced concomitantly. For example, if R¹ is halogen in intermediate 28, it may be converted to hydrogen in intermediate 29. Treatment with a sulfonyl chloride in the presence of a base such as pyridine followed by removal of the protecting group with, in the case of a tert-butylcarbamate, acid such as trifluoroacetic acid or methanolic hydrogen chloride, provides the sulfonamide I.

SCHEME 9

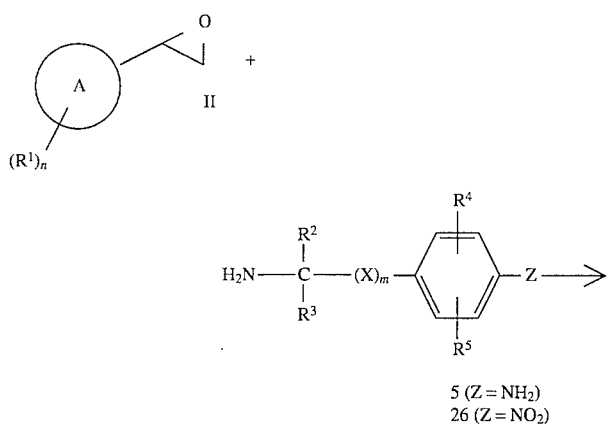

-continued
SCHEME 9

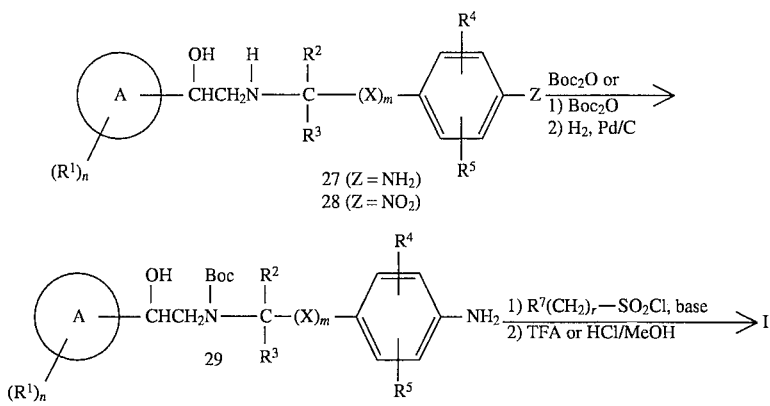

In some cases, compound I from the reaction sequence illustrated in Scheme 9 may be further modified, for example, by the removal of protecting groups or the manipulation of substituents on, in particular, $R^1$ and $R^7$, as described above. In addition, manipulation of substituents on any of the intermediates in the reaction sequence illustrated in Scheme 9 may occur. One such example is illustrated in Scheme 10. Compound 30, which is prepared as outlined in Scheme 9 from the corresponding epoxide, is subjected to reduction using tin(II) chloride to provide compound 31. Other examples of substituents on compound I which may be reduced to the corresponding amine by methods commonly known to those skilled in the art include nitro groups, nitriles, and azides.

2, as shown in Scheme 11. Amine III is alkylated with haloketone derivative 2, conveniently by treatment of a mixture of III and 2 with base such as potassium carbonate or triethylamine in a polar solvent such as acetonitrile, acetone or dimethylformamide. The resultant aminoketone 32 is reduced with, for example, sodium borohydride in methanol to give the desired aminoalcohol I.

SCHEME 10

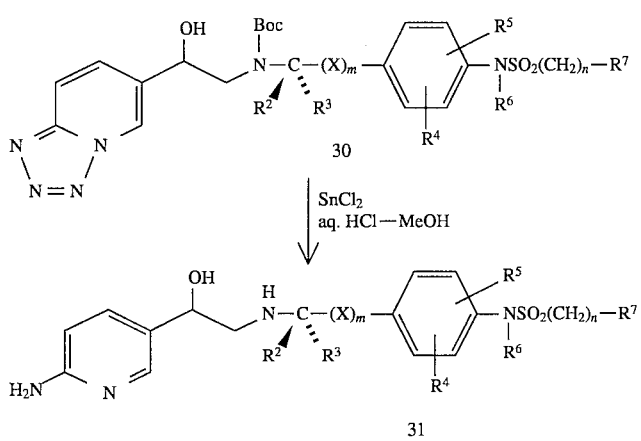

The compounds (I) of the present invention can also be prepared from amine intermediates such as those of formula III and haloketone intermediates such as those of formula

SCHEME 11

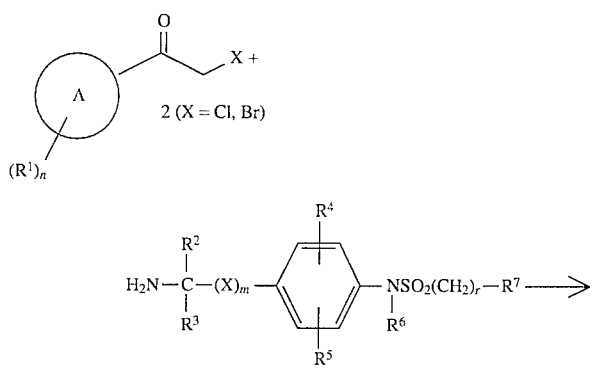

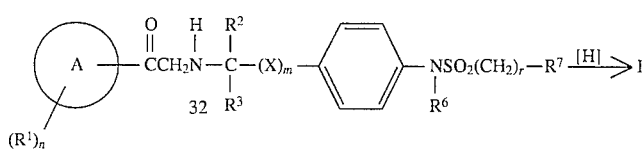

III

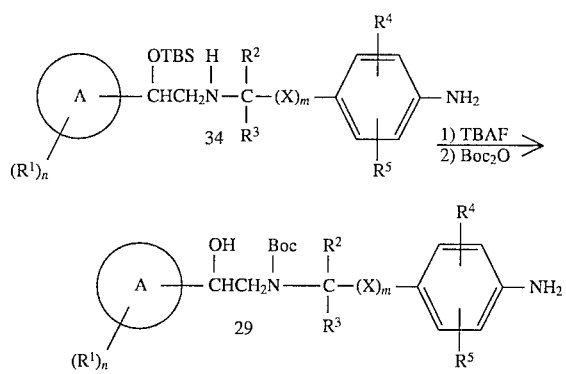

In some cases, the product I from the reaction described in Scheme 11 may be further modified, for example, by the removal of protecting groups or the manipulation of substituents on, in particular, $R^1$ and $R^7$. These manipulations may include, but are not limited to, reduction, oxidation, alkylation, acylation, and hydrolysis reactions which are commonly known to those skilled in the art.

An alternate synthesis of key intermediate 29 is shown is Scheme 12. The alcohol of intermediate 3 is protected, for example, as its t-butyldimethylsilyl ether to give TBS derivative 33. This compound is then treated with amine 5 and a base such as diisopropylethylamine in a solvent, typically polar aprotic such as acetonitrile, at temperatures of 25° to 150° C. for 1 to 72 hours. Typically, an iodide source such as sodium iodide is added to facilitate the reaction. The protecting group is then removed, in the case of silyl ether, by treatment of the resultant amine 34 with a fluoride source such as tetrabutylammonium fluoride. Protection of the secondary amine as before gives key intermediate 29.

SCHEME 12

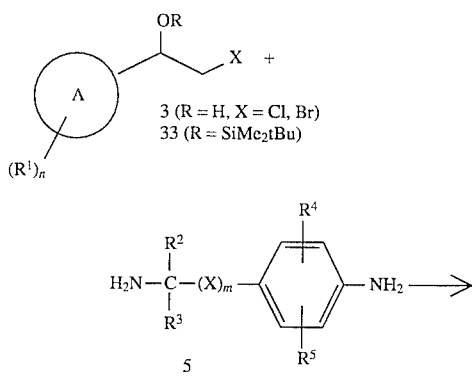

In some cases, compound I may be synthesized directly from intermediate 27 without protection of the secondary amine. For example, when $R^2$ and $R^3$ are both methyl, aniline derivative 27 is treated with sulfonyl chloride 7 and a base such as pyridine in a solvent such as dichloromethane at a temperature of −30° to 50° C., typically 0° C., to provide compound I.

In some cases, the product I from the reaction described in Scheme 13 may be further modified, for example, by the removal of protecting groups or the manipulation of substituents on, in particular, $R^1$ and $R^7$, as described above.

SCHEME 13

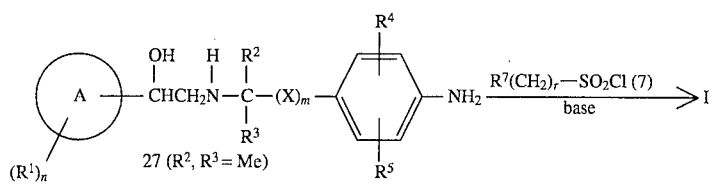

The compounds (I) of the present invention where $R^2$ and $R^3$ are hydrogen can also be prepared from acid intermediates of formula 36 and aminoalcohols of formula 37, as shown in Scheme 14. Acid 36 is available from the corresponding ester 35, typically a methyl or ethyl ester, by treatment with sulfonyl chloride 7 and a base such as pyridine, followed by hydrolysis of the ester with aqueous acid or base. Acid 36 is coupled to amine 37, which is known in the literature or readily prepared by methods known to those skilled in the art, using a coupling agent such as benzotriazolyl-N-oxy-tris(dimethylamino)phosphonium hexafluorophosphate or 1-(3-dimethylaminopropyl)-3-ethylcarbodiimide methiodide to provide the amide 38. This is treated with a reducing agent, typically borane, to provide the desired compound I.

SCHEME 14

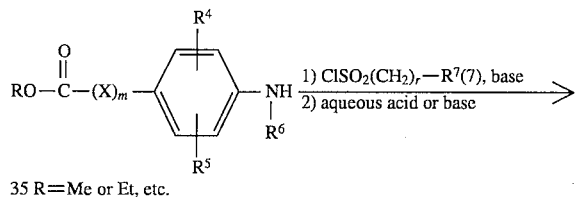

35 R=Me or Et, etc.

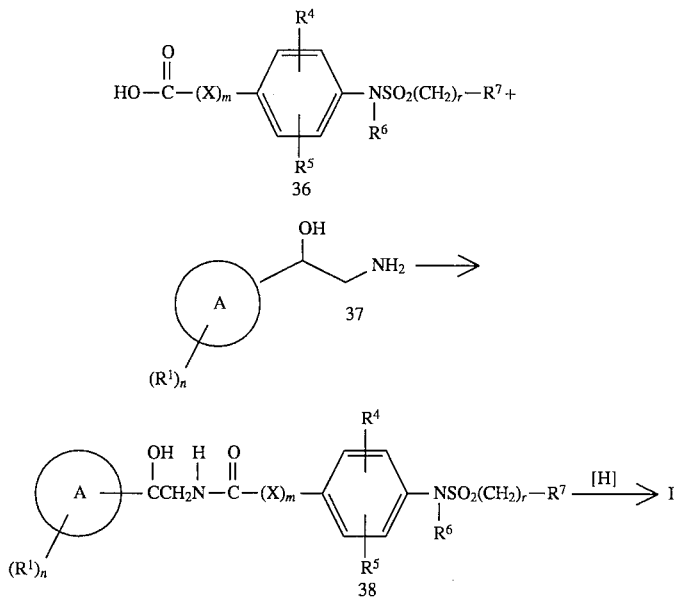

Compounds of the general Formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of a compound of the general Formula I may be obtained by stereospecific synthesis using optically pure starting materials of known configuration.

The instant compounds can be isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic and the like. In addition, certain compounds containing an acidic function such as a carboxy or tetrazole, can be isolated in the form of their inorganic salt in which the counterion can be selected from sodium, potassium, lithium, calcium, magnesium and the like, as well as from organic bases.

As previously indicated, the compounds of the present invention have valuable pharmacological properties.

The present invention also provides a compound of the general Formula I or a pharmaceutically acceptable salt thereof for use as an active therapeutic substance.

In one aspect, the present invention provides a compound of the general Formula I or a pharmaceutically acceptable ester thereof: or a pharmaceutically acceptable salt thereof for use in the treatment of obesity in human or non-human animals.

The present invention further provides a compound of the general Formula I, or a pharmaceutically acceptable ester thereof; or pharmaceutically acceptable salt thereof, for use in the treatment of hyperglycemia (diabetes) in human or non-human animals.

The disease diabetes mellitus is characterized by metabolic defects in production and utilization of glucose which result in the failure to maintain appropriate blood sugar levels. The result of these defects is elevated blood glucose or hyperglycemia. Research on the treatment of diabetes has centered on attempts to normalize fasting and postprandial blood glucose levels. Treatments have included parenteral administration of exogenous insulin, oral administration of drugs and dietary therapies.

Two major forms of diabetes mellitus are now recognized. Type I diabetes, or insulin-dependent diabetes, is the result of an absolute deficiency of insulin, the hormone which regulates glucose utilization. Type II diabetes, or insulin-independent diabetes, often occurs in the face of normal, or even elevated levels of insulin and appears to be the result of the inability of tissues to respond appropriately to insulin. Most of the Type II diabetics are also obese.

In addition the compounds of the present invention lower triglyceride levels and cholesterol levels and raise high density lipoprotein levels and are therefore of use in combatting medical conditions wherein such lowering (and raising) is thought to be beneficial. Thus they may be used in the treatment of hyper-triglyceridaemia, hypercholesterolaemia and conditions of low HDL (high density lipoprotein) levels in addition to the treatment of atherosclerotic disease such as of coronary, cerebrovascular and peripheral arteries, cardiovascular disease and related conditions.

Accordingly, in another aspect the present invention provides a method of lowering triglyceride and/or cholesterol levels and/or increasing high density lipoprotein levels which comprises administering, to a human or a non-human animal in need thereof, a therapeutically effective amount of a compound of the formula (I) or pharmaceutically acceptable salt thereof. In a further aspect the present invention provides a method of treating atherosclerosis which comprises administering, to an animal in need thereof; a therapeutically effective amount of a compound of the formula (I) or pharmaceutically acceptable salt thereof. The compositions are formulated and administered in the same general manner as detailed below for treating diabetes and obesity. They may also contain other active ingredients known for use in the treatment of atherosclerosis and related conditions, for example fibrates such as clofibrate, bezafibrate and gemfibrozil; inhibitors of cholesterol biosynthesis such as HMG-CoA reductase inhibitors for example lovastatin, simvastatin and pravastatin; inhibitors of cholesterol absorption for example beta-sitosterol and (acyl CoA:cholesterol acyl-transferase) inhibitors for example melinamide; anion exchange resins for example cholestyramine, colestipol or a dialkylaminoalkyl derivatives of a cross-linKed dextran; nicotinyl alcohol, nicotinic acid or a salt thereof; vitamin E; and thyromimetics.

The compounds of the instant invention also have the effect of reducing intestinal motility and thus find utility as aiding in the treatment of various gastrointestinal disorders such as irritable bowel syndrome. It has been proposed that the motility of non-sphincteric smooth muscle contraction is mediated by activity at $\beta_3$ adrenoreceptors. The availability of a $\beta_3$ specific agonist, with little activity at $\beta_1$ and $\beta_2$ receptors will assist in the pharmacologic control of intestinal motility without concurrent cardiovascular effects. The instant compounds are administered generally as described below with dosages similar to those used for the treatment of diabetes and obesity.

It has also been found unexpectedly that the compounds which act as agonists at $\beta_3$ adrenoreceptors may be useful in the treatment of gastrointestinal disorders, especially peptic ulcerations, esophagitis, gastritis and duodenitis, (including that induced by *H. pylori*), intestinal ulcerations (including inflammatory bowel disease, ulcerative colitis, Crohn's disease and proctitis) and gastrointestinal ulcerations.

In addition, $\beta_3$ receptors have been indicated to have an effect on the inhibition of the release of neuropeptides in certain sensory fibers in the lung. As sensory nerves may play an important role in the neurogenic inflammation of airways, including cough, the instant specific $\beta_3$ agonists may be useful in the treatment of neurogenetic inflammation, such as asthma, with minimal effects on the cardiopulmonary system.

$\beta_3$ adrenoreceptors are also able to produce selective antidepressant effects by stimulating the $\beta_3$ receptors in the brain and thus an additional contemplated utility of the compounds of this invention are as antidepressant agents.

The active compounds of the present invention may be orally administered as a pharmaceutical composition, for example, with an inert diluent, or with an assimilable edible carder, or they may be enclosed in hard or soft shell capsules, or they may be compressed into tablets, or they may be incorporated directly with the food of the diet. For oral therapeutic administration, which includes sublingual administration, these active compounds may be incorporated with excipients and used in the form of tablets, pills, capsules, ampules, sachets, elixirs, suspensions, syrups, and the like. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The effective dosage of active ingredient employed may vary depending on the particular compound employed, the mode of administration, the condition being treated and the severity of the condition being treated.

When treating diabetes mellitus and/or hyperglycemia generally satisfactory results are obtained when the compounds of the present invention are administered at a daily dosage of from about 0.001 milligram to about 100 milligram per kilogram of animal body weight, preferably given in a single dose or in divided doses two to six times a day, or in sustained release form. In the case of a 70 kg adult human, the total daily dose will generally be from about 0.07 milligrams to about 350 milligrams. This dosage regimen may be adjusted to provide the optimal therapeutic response.

When treating obesity, in conjunction with diabetes and/or hyperglycemia, or alone, generally satisfactory results are obtained when the compounds of the present invention are administered at a daily dosage of from 0.01 milligram to about 100 milligrams per kilogram of animal body weight, preferably given in a single dose or in divided doses two to six times a day, or in sustained release form. In the case of a 70 kg adult human, the total daily dose will generally be from about 0.7 milligrams to about 3500 milligrams. This dosage regimen may be adjusted to provide the optimal therapeutic response.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

These active compounds may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

The following examples are provided so that the invention might be more fully understood. They should not be construed as limiting the invention in any way.

EXAMPLE 1

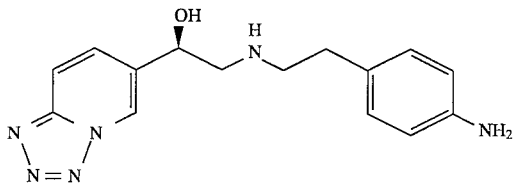

(R)-N-[2-[4-(aminophenyl)]ethyl]-2-hydroxy-2-(tetrazolo[1,5-a]pyrid- 6-yl)ethylamine A solution of 1.62 g (10 mmol) of (R)-2-(tetrazolo[1,5-a]pyrid-6-yl)oxirane (See Fisher and Wyvratt, European Patent Application 0 318 092 A2 for the synthesis of this compound.) and 4.1 g (30 mmol) of 2-(4-aminophenyl)ethylamine in 30 mL of methanol was heated at reflux for 5h. The reaction mixture was concentrated and the residue chromatographed on silica gel (2% methanol/98% methylene chloride) to give 1.69 g (56%) of the title compound: $^1$H NMR (400 MHz, CD$_3$OD) δ 9.01 (d, 1H, J=1.3 Hz), 8.02 (d, 1 H, J=9.2 Hz), 7.82 (dd, 1H, J=1.3, 9.2 Hz), 6.94 (d, 2H, J=6.3 Hz), 6.63 (d, 2H, J=6.3 Hz), 4.91 (m, 1H), 2.82 (m, 4H), 2.67 (t, 2 H, J=7.1Hz).

EXAMPLE 2

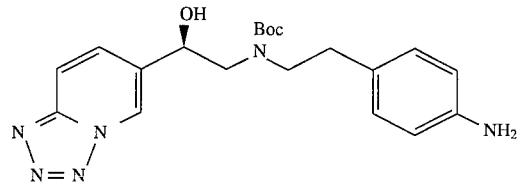

(R)-N-[2-[4-(aminophenyl)]ethyl]-2-hydroxy-2-(tetrazolo[1,5-a]pyrid- 6-yl)ethylcarbamic acid 1,1-dimethylethyl ester A solution of 1.69 g (56.7 mmol) of the amine from Example 1 and 1.23 g (56.7 mmol) of di-tert-butyl dicarbonate in 10 mL of tetrahydrofuran (THF) at 0° C. was stirred for 2 h. The reaction mixture was concentrated and the residue chromatographed on silica gel (4% methanol/96% methylene chloride) to afford 2.2 g (97%) of the title compound: $^1$H NMR (400 MHz, CD3OD) δ5 8.96 (s, 1H), 8.05 (m, 2H), 7.85 (m, 2H), 6.93 (dd, 2H, J=7.7, 8.3 Hz), 6.66 (d, 2H, J=8.3 Hz), 4.99 (m, 1H), 3.49 (m, 4H), 2.70 (t, 2H, J=6.5 Hz), 1.26 (s, 9H).

EXAMPLE 3

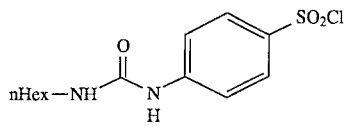

4-(Hexylaminocarbonylamino)benzenesulfonyl chloride

Hexylamine, 12.15 ml (9.2 mmol), was added dropwise to a solution of 10 ml (9.2 mmol) of phenyl isocyanate in THF (150 ml) at 0° C., and stirring was continued for 1 h. The solvent was removed in vacuo, and the resultant hexyl phenyl urea was used without further purification.

A 6-g (2.7 mmol) portion was added over 20 min to chlorosulfonic acid at 0° C., followed by heating at 60° C. for 2h. After cooling, the mixture was added to ice/water (100 ml) and the aqueous phase extracted with EtOAc (3×100 ml). The combined organic phase was washed with brine (50 ml), dried with MgSO$_4$, concentrated, and purified by flash chromatography (silica gel, 75% hexane/25% ethyl acetate) to give 6 g (70%) of the title compound: $^1$H NMR (CDCl$_3$) δ7.85 (d, 2H, J=9.6 Hz), 7.54 (d, 2H, J=9.6 Hz), 6.79 (br.s, 1H), 4.71(br. s, 1H), 3.23 (t, 2H, J=8 Hz), 1.54-1.44 (m, 2H), 1.33-1.20 (m, 6H), 0.91-0.79 (m, 3H).

EXAMPLE 4

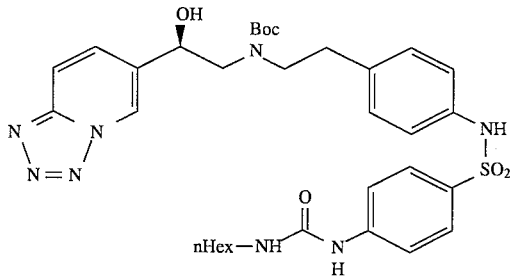

(R)-N-[4-[2-[N-(1,1-dimethylethoxycarbonyl)-N-[2-hydroxy- 2-(tetra-zolo[ 1,5-a]pyrid-6-yl)]ethyl]amino]ethyl]phenyl]- 4-(hexylaminocarbon-ylamino)benzenesulfonamide To a stirred solution of 0.200 g (0.502 mmol) of the Boc-compound from Example 2 in 3 mL of methylene chloride was added 80 mg(1.00 mmol) of pyridine followed by 0.16 g (0.75 mmol) of the sulfonyl chloride from Example 3. After being stirred for 5h, the reaction mixture was concentrated and the residue chromatographed on silica gel (10% methanol/90% methylene chloride) to afford 0.303 g (88%) of the title compound: $^1$H NMR (400 Hz, CD3OD) δ8.95 (s, 1H), 8.0–8.08 (m, 1H), 7.75–7.87 (m, 1H), 7.40–7.62 (m, 4H), 7.00 (m, 4H), 4.95 (m, 2H), 3.47 (m, 2H), 3.15 (m, 2H), 2.75 (m, 2H), 1.52 (t, 2H, J=6.0 Hz), 1.33 (m, 8H), 1.21 (s, 9H), 0.90 (t, 3H, J=6.0 Hz).

EXAMPLE 5

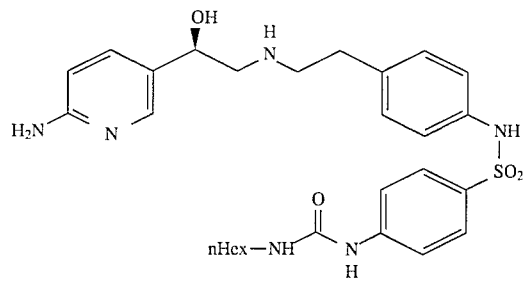

(R)-N-[4-[2-[[2-hydroxy-2-(6-aminopyridin-3-yl)ethyl]amino]ethyl]-phenyl]- 4,-(hexylaminocarbonylamino)benzenesulfonamide A mixture of 0.302 g (0.44 mmol) of the tetrazine from Example 4, 0.20 g (0.88 mol) of tin(II) chloride dihydrate and 0.3 ml of concentrated aqueous hydrochloric acid in 2 mL of methanol was heated at reflux for 5 h. The reaction mixture was concentrated and the residue purified by reverse-phase MPLC (C8, 47%methanol/53 0.1% trifluoroacetic acid buffer) to give 0.32 g (78%) of the title compound as its bistrifluoroacetate salt: $^1$H NMR (400 MHz, CD$_3$OD) δ 7.96 (dd, 1H, J=2.0, 9.2 Hz), 7.86 (d, 1H, J=2.0 Hz), 7.59 (d, 2H, J=8.8 Hz), 7.43 (d, 2H, J=8.8 Hz), 7.14 (d, 2H, J=8.4 Hz), 7.07 (d, 2H, J=8.4 Hz), 7.03 (d, 1H, J=9.2 Hz), 4.92 (m, 1H), 3.23 (m, 2H), 3.15 (m, 2H), 2.93 (m, 2H, 4.0 Hz), 1.49 (t, 2H, J=6.0Hz), 1.32 (m, 8H), 0.91 (t, 3H, J=6.0 Hz); CI MS m/z 555(M+1).

Following the procedures outlined for Examples 1–5, the compounds listed in Table 1 were prepared.

TABLE 1

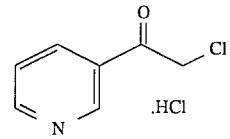

| Example | R | Selected $^1$H NMR (CD$_3$OD) Data |
|---|---|---|
| 6 | Ph, trifluoroacetate salt | 7.74(m, 2H), 7.53(m, 1H), 7.45 (m, 2H). |
| 7 | 2-naphthyl, trifluoroacetate salt | 7.93(m, 4H), 7.75(d, 1H, J=1.7 Hz), 7.61(m, 2H) |
| 8 | 3-quinolinyl, trifluoroacetate salt | 9.00(d, 1H, J=2.3Hz), 8.06(m, 2H), 7.94(m, 2H), 7.72(t, 1H, J= 7.2Hz) |
| 9 | 1,2-benzisoxazol-5-yl, trifluoroacetate salt | 9.02(s, 1H), 8.30(d, 1H, J=1.3 Hz), 7.90(m, 1H), 7.77(m, 1H) |
| 10 | 4-iodophenyl, trifluoroacetate salt | 7.83(d, 2H, J=8.6Hz), 7.46(d, 2H, J=8.6Hz) |
| 11 | 4-[(N-hexyl, N-methyl-aminocarbonyl)amino]-phenyl, trifluoroacetate salt | 7.62(d, 2H, J=4.6Hz), 7.48(d, 2H, J=4.6Hz), 2.99(s, 3H) |
| 12 | 4-[(N,N-dimethyl-aminocarbonyl)amino]-phenyl, trifluoroacetate salt | 3.0(s, 6H) |
| 13 | 4-(3-hexyl-2-imidazolidinon-1-yl)phenyl, trifluoroacetate salt | 3.88–3.83(m, 2H), 3.57–3.50(m, 2H), 2.89–2.95(m, 2H), 1.61–1.52 (m, 2H), 1.37–1.30(m, 6H), and 0.93–0.88(m, 3H) |

EXAMPLE 14

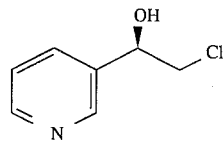

3-(2-Chloroacetyl)pyridine hydrochloride

To a solution of 12 g (11 mL, 100 mmol) of 3-acetylpyridine in 100 mL of ethyl ether was added 100 mL of 1 M ethereal hydrogen chloride. The resultant precipitate was filtered and 15.0 g (95.2 mmol) was collected and placed in a 500-mL round bottom flask equipped with a magnetic stir bar. To this was added 95 mL of 1 M hydrogen chloride in acetic acid. After the mixture was stirred until all the solid had dissolved, 12.7 g (95.2 mmol) of N-chlorosuccinimide (NCS) was added in one portion. The solution turned yellow and the NCS gradually dissolved. After 4 h, a white precipitate had formed. The mixture was allowed to stir for 2.5 days. It was then filtered. The solid collected was washed with 10 mL of acetic acid and 200 mL of ethyl ether to give 15.2 g (83%) of the title compound as a white solid: 1H NMR (200 MHz, d$_6$-DMSO) δ9.22 (t, H, J=1 Hz), 8.29 (dd, 1H, J=1.6, 5.1 Hz), 8.55 (td, 1H, J=2, 8.1 Hz), 7.82 (ddd, 1H, J=0.8, 5.1, 8.1 Hz), 5.27 (s, 2H).

EXAMPLE 15

(R)-α-Chloromethyl-3-pyridinemethanol

To a stirred solution of 3.67 g (11.5 mmol) of (–)-B-chlorodiisopinocampheylborane [(–)-DIP-Cl] in 11 mL of THF at –25° C. was added a slurry of 1.00 g (5.21 mmol) of the product from Example 14 in 5 mL of THF via a cannula. Following the addition of 0.80 mL (5.79 mmol) of triethylamine, the reaction mixture was stirred at –25° C. for 4 days. To the mixture was added 10 mL of water which was then allowed to warm to room temperature. To the mixture was added 20 mL of ethyl acetate and the organic phase separated. The aqueous phase was neutralized with saturated NaHCO₃ solution then extracted six times with ethyl acetate. The combined organic phase was concentrated in vacuo to afford a yellow oil. Hash chromatography (silica gel, 75–100% ethyl acetate-hexanes) afforded 561 mg (68%) of the title compound as a pale yellow oil: $^1$H NMR (400 MHz, CD3OD) δ5 8.58 (d, 1H, J=1.8 Hz), 8.46 (dd, 1H, J =4.9, 1.5 Hz), 7.90 (d, 1H, J=7.9 Hz), 7.44 (dd, 1H, J=7.9, 4.9 Hz), 4.93 (m, 1H), 3.75 (m, 2H).

EXAMPLE 16

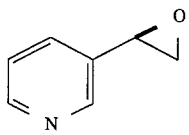

(R)-(Pyrid-3-yl)oxirane

To a solution of 557 mg (3.55 mmol) of the product from Example 15 in 16 mL of acetone was added 1.80 g of potassium carbononate. The mixture was heated at reflux for 20 h then cooled to room temperature. The mixture was filtered and the flitrate evaporated in vacuo. Flash chromatography (silica gel, 2% methanol-methylene chloride) afforded 262 mg (61%) of the title compound as a pale yellow oil: 1H NMR (200 MHz, CDCl₃) δ 8.54 (m, 2H), 7.52 (m, 1H), 7.24 (m, 1H), 3.86 (dd, 1H, J= 4.0, 2.5 Hz), 3.17 (dd, 1H, J=5.4, 4.0 Hz), 2.80 (dd, 1H, J=5.4, 2.5 Hz).

EXAMPLE 17

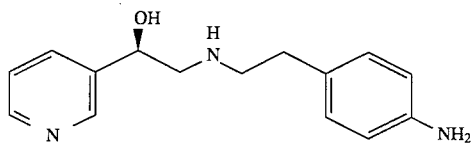

(R)-N-[2-[4-(Aminophenyl)]ethyl]-2-hydroxy-2-(pyrid-3-yl)ethylamine

To a stirred solution of 377 mg (2.44 mmol) of 4-aminophenethylamine in 10 mL of methanol was added a solution of 300 mg (2.48 mmol) of the product from Example 16 in 15 mL of methanol. The mixture was heated at reflux for 16 h then cooled to room temperature. The methanol was removed in vacuo and the residue chromatographed (silica gel, 6–8% methanol, 1% ammonia-methylene chloride) to afford 101 mg (16%) of the title compound together with 279 mg of a mixture that was rechromatographed (5% methanol, 1% ammonia-methylene chloride) to give a further 54 mg (9%) of the title compound as an off-white solid: $^1$H NMR (500 MHz, CD₃OD) δ8.52 (d, 1H, J=1.8 Hz), 8.43 (dd, 1H, J=4.8, 1.4 Hz), 7.81 (m, 1H), 7.40 (m, 1H), 6.95 (d, 2H, J=8.3 Hz), 6.67 (d, 2H, J=8.3 Hz), 4.81 (m, 1H), 2.90-2.65 (m, 6H).

EXAMPLE 18

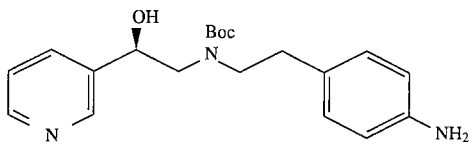

(R)-N-[2-[4-(aminophenyl)]ethyl]-2-hydroxy-2-(pyrid-3-yl) ethylcarbamic acid 1,1-dimethylethyl ester A solution of 386 mg(1.77 mmol) of di-tert-butyl dicarbonate in 3.5 mL of THF was added, via a cannula, to a stirred slurry of 456 mg (1.77 mmol) of the product from Example 17 in 3.6 mL of THF cooled to 0° C. The yellow solution was stirred at 0° C. for 3 h, then the THF was removed in vacuo. Hash chromatography (silica gel, 10% methanol, 1% ammonia-methylene chloride) afforded 549 mg (87%) of the title compound as an off white solid: $^1$H NMR (500 MHz, CD₃OD, mixture of rotomers) δ5 8.45 (m, 2H), 7.83 (d, 0.6H, J=7.4 Hz), 7.78 (d, 0.4H, J=6.9 Hz), 7.41 (m, 1H), 6.94 (d, 0.8H, J=8.0 Hz), 6.89 (d, 1.2H, J=7.8 Hz), 6.66 (d, 2H, J=7.3 Hz), 4.89 (m, 1H), 3.42-3.21 (m, 4H), 2.67 (m, 2H), 1.39 (s, 5.4H), 1.36 (s, 3.6H).

An alternative synthesis of the aniline derivative in Example 18 is illustrated in Examples 19–23:

EXAMPLE 19

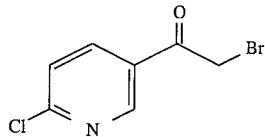

2-Chloro-5-(2-bromoacetyl)pyridine

A solution of 784 mg of 2-chloro-5-acetylpyridine in 10 mL of THF was added via canula to a solution of 1.44 g of dibromobarbituric acid (DBBA) in 10 mL of THF. The resultant solution was heated at 50°–55° C. for 12 h, and then an additional 0.72 g DBBA was added. After stirring at 50°–55° C. for 2.5 more hours, 0.36 g DBBA was added. The mixture was allowed to stir for 2 h at which point NMR analysis of an aliquot indicated 87% conversion. The reaction mixture was cooled, diluted with ethyl acetate, washed with two portions of saturated aqueous sodium bicarbonate, water, and brine, dried over magnesium sulfate and concentrated. Purification by flash chromatography (silica gel, 15% ethyl acetate/hexane) provided 0.86 g (73%) of the title compound as a white solid: $^1$H NMR (400 MHz, CDCl₃) δ8.96 (d, 1H, J=2.6 Hz), 8.21 (dd, 1H, J=2.5, 8.3 Hz), 7.46 (d, 1H, J=8.4 Hz), 4.37 (s, 2H). The NMR also indicated the presence of the corresponding 2-bromo derivative. The ~4:1 mixture was carried on through the synthesis.

EXAMPLE 20

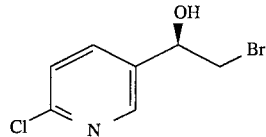

(R)-α-Bromomethyl-3-(6-chloropyridine)methanol

To a solution of 602 mg(1.88 mmol) of (–)-DIP-Cl in 0.5 mL of THF at –25° C. was added via canula 200 mg of ketone from Example 19 in 1.5 mL of THF at –25° C. The reaction mixture was allowed to stir at −25° C. for 17 h. It was then quenched by the addition of water and extracted with ether. The ether phase was diluted with ethyl acetate, washed with two portions of saturated aqueous sodium bicarbonate, water, and brine, dried over magnesium sulfate and concentrated. Purification by flash chromatography (silica gel, 15 and 25% ethyl acetate/hexane) gave 170 mg (84%) of the title compound: 1H NMR (400 MHz, CDCl₃) δ 8.38 (d, 1H), 7.70 (dd, 1H), 7.32 (d, 1H), 4.97 (m, 1H), 3.61 (dd, 1H), 3.50 (dd, 2.85 (d,

EXAMPLE 21

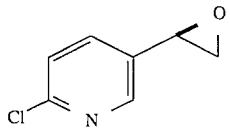

(R)-(2-chloropyrid-5-yl)oxirane

To a solution of 100 mg of bromoalcohol from Example 20 in mL of 1:1 THF:water was added 1 mL of 5 N aqueous sodium hydroxide solution. The mixture was allowed to stir for 10 min. It was then extracted with three portions of dichloromethane. The combined organic phases were washed with two portions of water and brine, dried over magnesium sulfate, and concentrated to give 98 mg (93%) of the title compound which was used without further purification: ¹H NMR (400 MHz, CDCl₃) δ 8.34 (d, 1H), 7.48 (dd, 1H), 7.29 (d, 1H), 3.86 (dd, 1H), 3.18 (dd, 1H), 2.78 (dd, 1H).

EXAMPLE 22

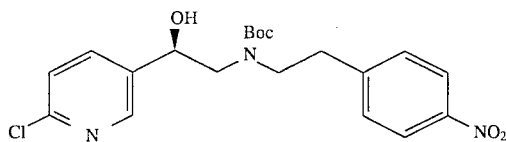

(R)-N-[2-[4-(Nitrophenyl)]ethyl]-2-hydroxy-2-(2-chloropyrid- 5-yl)ethylcarbamic acid 1,1-dimethylethyl ester Following the procedure outlined in Examples 17 and 18, the title compound was prepared from the epoxide from Example 21 and 4-nitrophenylethylamine: ¹H NMR (400 MHz, CDCl₃) δ 8.32 (d, 1H, J=1.3 Hz), 8.13 (d, 2H, J=8.6 Hz), 7.66 (br m, 1H), 7.30 (d, 2H, J=8.1 Hz), 7.27 (br m, 1H), 4.94 (br m), 3.38 (br m, 4H), 2.84 (br m, 2H), 1.40 (s, 9H).

EXAMPLE 23

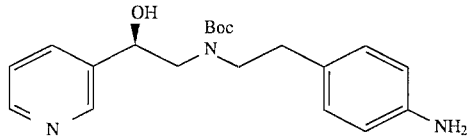

(R)-N-[2-[4-(aminophenyl)]ethyl]-2-hydroxy-2-(pyrid-3-yl-)ethylcarbamic acid 1,1-dimethylethyl ester To a solution of 80 mg (0.19 mmol) of the nitro compound from Example 22 in 2 mL of ethanol was added 0.114 mL (0.57 mmol) of 5 N aqueous sodium hydroxide solution and 20 mg of raney nickel. The reaction mixture was shaken at room temperature under 45 psi hydrogen for 16 h. The mixture was neutralized with saturated aqueous sodium phosphate monobasic and extracted with three portions of ethyl acetate. The combined organic phases were washed with water and brine, dried (magnesium sulfate), and concentrated to give 40 mg (59%) of the title compound which was identical to the sample prepared in Example 18.

EXAMPLE 24

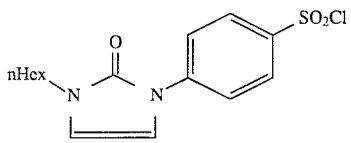

4-(3-Hexyl-2-imidazolon-1-yl)benzenesulphonyl chloride

Hexyl iodide (50 mmol, 7.38 ml) was added to a mixture of 2-amino acetaldehyde dimethyl acetal (100 mmol, 11 ml) and potassium carbonate (50 mmol, 6.9 g) in DMF (10 ml) at 0° C. Stirring was continued for 16h before diluting with ethyl acetate (200 ml), and ffitering the solution through a plug of celite. Concentration in vacuo was follwed by column chromatography (eluant ethyl acetate) to give N-hexyl 2-amino acetaldehyde dimethyl acetal (7.39 g, 78%) as a colourless oil.

To the amine (38.6 mmol, 7.3 g) in methylene chloride (100 ml) at 0° C. was added 4-(chlorosulphonyl) phenyl isocyanate (38.6 mmol, 8.4 g). The reaction mixture was stirred for 20 mins until a clear solution had formed, and 1:1 water:trifluoroacetic acid (100 ml total) was added. Vigorous stirring was continued for 16h., the layers separated, the organic layer was diluted with ethyl acetate (500 ml) and washed with saturated sodium bicarbonate solution (4'50 ml), brine (50 ml), dried with anhydrous magnesium sulphate, and concentrated in vacuo. Column chromatography (eluant 3 hexane/1 ethyl acetate) yielded the title compound as pale yellow crystals (8.8 g, 67%).

EXAMPLE 25

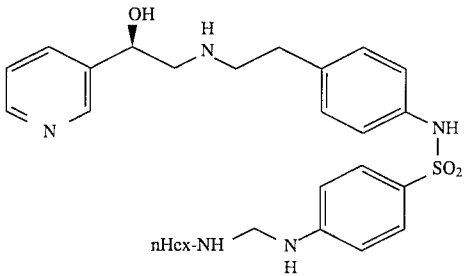

(R)-N-[4-[2-[[2-Hydroxy-2-(pyridin-3-yl)ethyl]amino] ethyl]phenyl]- 4-(hexylaminocarbonylamino)benzenesulfonamide To a solution of 302 mg (0.845 mmol) of the product from Example 18 and 137 mL (1.69 mmol) of pyridine in 10 mL of methylene chloride was added 296 mg (0.928 mmol) of 4-(hexylaminocarbonylamino)benzenesulfonyl chloride from Example 3. The reaction was stirred for 12 h then the solvent removed in vacuo. Hash chromatography (silica gel, 6% methanol, 0.5% ammonia-methylene chloride) afforded 468 mg (87%) of the BOC-protected title compound.

A solution of 468 mg (0.731 mmol) of BOC-protected tire compound in 5 mL of methylene chloride and 5 mL of trifluoroacetic acid was stirred for 30 min then the volatile components removed in vacuo. The residue was azeotroped twice with 10% methanol/toluene, twice with methanol, then dried in vacuo to give 521 mg (93%) of the title compound as its trifluroracetate salt: ¹H NMR (400 MHz, CD₃OD) δ 8.88 (s, 1H), 8.79 (d, 1H, J=5.5 Hz), 8.53 (d, 1H, J=8.2 Hz), 7.99 (m, 1H), 7.59 (dd, 2H, J=6.9, 1.9 Hz), 7.43 (dd, 2H, J=6.9, 1.9 Hz), 7.15 (dd, 2H, J=8.6, 2.1 Hz ), 7.08 (dd, 2H, J=8.6, 2.1 Hz), 5.23 (m, 1H), 3.40-3.10 (m, 6H), 2.94 (m, 2H), 1.49 (m, 2H), 1.32 (m, 6H), 0.90 (m, 2H).

EXAMPLE 26

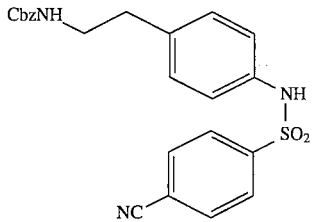

(N)-[4-[2-[(phenylmethoxycarbonyl)amino]ethyl]phenyl]-4-cyanobenzensulfonamide

Following the procedure outlined in Example 4, the title compound was prepared from 2-(4-aminophenyl)ethylcarbamic acid phenylmethyl ester (see Fisher, et. al., Eur. Pat. Appl. 0 611 003 A1, 1994) and 4-cyanobenzenesulfonyl chloride: ¹H NMR (400 MHz, CD₃OD) δ¹H NMR (400 MHz, CDCl₃) δ7.81 (d, 2H, J=8.7Hz), 7.69 (d, 2H, J=8.7Hz), 7.32 (m, 5H), 7.06 (d, 2H, J=8.4Hz), 6.96 (d, 2H, J=8.4Hz), 6.75 (s, 1H), 5.06 (s, 2H), 4.71 (t, br, 1H), 3.38 (q, 2H, J=6.9Hz), 2.74 (t, 2H, J=7.0Hz).

EXAMPLE 27

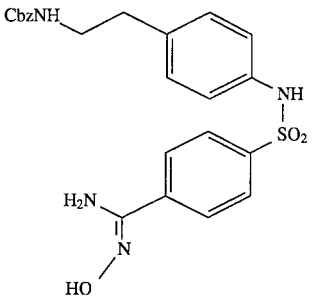

(N)-[4-[2-[(phenylmethoxycarbonyl)amino]ethyl]phenyl]-4-aminooximidomethyl)benzensulfonamide A mixture of the nitrile from Example 26 (2.71 g, 6.23 mmol), absolute ethanol (65 ml), finely divided K₂CO₃ (5.17 g, 37.4 mmol), and hydroxylamine hydrochloride (2.17 g, 31.2 mmol) was refluxed for 6 h. The ethanol was removed under reduced pressure. The resulting solid was dissolved in ethyl acetate and washed with water 3 times. The organic phase was concentrated in vacuo to 2.87 g (98%) of the title compound as a white powder which was of sufficient purity to be used in subsequent steps: 1H NMR (400 MHz, CD₃OD) δ7.71 (s, 4H), 7.31 (m, 5H), 7.04 (d, 2H, J=8.4Hz), 6.99 (d, 2H, J=8.4Hz), 5.02 (s, 2H), 3.25 (t, 2H, J=6.8Hz), 2.67 (t, 2H, J=6.7Hz).

EXAMPLE 28

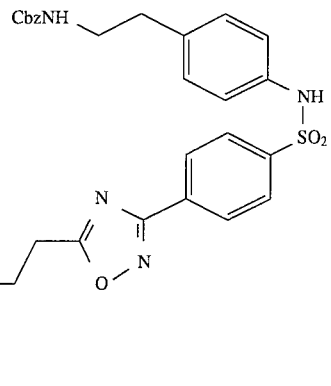

(N)-[4-[2-[(phenylmethoxycarbonyl)amino]ethyl]phenyl]-4-[5-( 3-cyclopentylpropyl)-[1,2,4]-oxadiazol-3-yl]benzensulfonamide To a solution of compound from Example 27 (0.468 g, 1.00 mmol) in dry pyridine (5.0 ml) was added 4-cyclopentylbutyryl chloride (0.175 g, 1.00 mmol). The mixture was refluxed for 3.5 h. The pyridine was removed under reduced pressure. The resulting residue was purified by silica gel chromatography (35% ethyl acetate in hexanes) to give 0.152 g (26%) of the title compound: 1H NMR (400 MHz, CDCL₃) δ 8.12 (d, 2H, J=8.7Hz), 7.81 (d, 2H, J=8.7Hz), 7.31 (m, 5H), 7.03 (d, 2H, J=8.1Hz), 6.97 (d, 2H, J=8.4Hz), 6.67 (s, 1H), 5.05 (s, 2H), 4.70 (t, br, H), 3.37 (q, 2H, J=6.5Hz), 2.91 (t, 2H, J=7.6Hz), 2.72 (t, 2H, J=7.0), 1.90-1.70 (m, 5H), 1.65-1.30 (m, 6H), 1.06 (m, 2H).

EXAMPLE 29

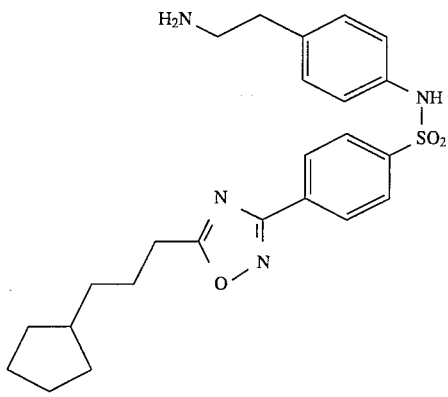

N-[4-(2-aminoethyl)phenyl]-4-[5-(3-cyclopentylpropyl)-[1,2,4]-oxadiazol-3-yl]benzensulfonamide A mixture of Cbz amine from Example 28 (0.145 g, 0.246 mmol), palladium hydroxide on carbon (0.02 g), and glacial acetic acid (5.0 ml) was hydrogenated for 2 h. The acetic acid was removed under reduced pressure. The residue was purified by silica gel chromatography (1:9 of 10% ammonium hydroxide in methanol:methylene chloride) to give 0.058 g (52%) of the title compound: 1H NMR (400 MHz, CD₃OD) δ 8.11 (d, 2H, J=8.6Hz), 7.87 (d, 2H, J=8.5Hz), 7.06 (d, 2H, J=8.6Hz), 7.02 (d, 2H, J=8.7Hz), 2.97 (t, 2H, J=7.5Hz), 2.84 (t, 2H, J=6.9Hz), 2.67 (t, 2H, J=7.5Hz), 1.90-1.75 (m, 5H), 1.70-1.40 (m, 6H), 1.12 (m, 2H).

EXAMPLE 30

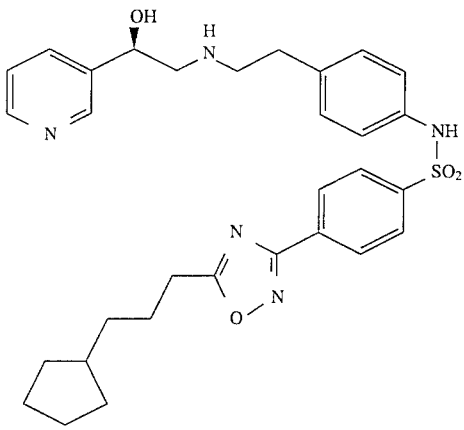

(R)-N-[4-[2-[[2-Hydroxy-2-(pyridin-3-yl)ethyl]amino] ethyl]phenyl]-4-[5-(3-cyclopentylpropyl)-[1,2,4]-oxadiazol-3-yl]benzensulfonamide To a solution of amine from Example 29 (0.053 g, 0.117 mmol) in dry methanol (30.0 ml) was added 3-pyridine epoxide from Example 16 (0.021 g, 0.175 mmol). The resulting solution was refluxed overnight. After concentration, the residue was purified by silica gel chromatography (13% methanol in methylene chloride) to give 0.01 g (15%) of the title compound: $^1$H NMR (400 MHz, CD$_3$OD) δ 8.52 (d, 1H, J=1.9Hz), 8.42 (dd, 1H, J-1.5, 4.8Hz), 8.13 (d, 2H, J-8.6Hz), 7.85 (m, 3H), 7.40 (dd, 1H, J=4.8, 7.8Hz), 7.10 (d, 1H, J=8.6Hz), 7.03 (d, 2H, J=8.6Hz), 4.81 (dd, 1H, J=4.9, 8.1Hz), 2.96 (t, 2H, J=7.5Hz), 2.93-2.70 (m, 6H), 1.90-1.72 (m, 5H), 1.68-2.48 (m, 4H), 1.42 (m, 2H), 1.11 (m, 2H).

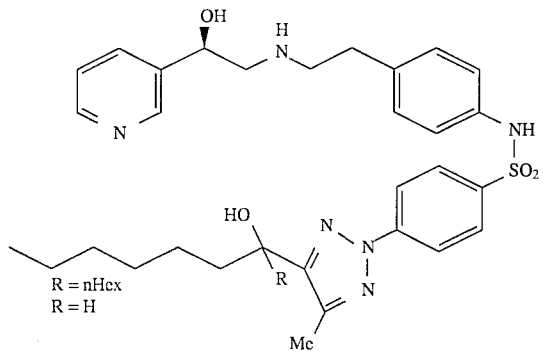

EXAMPLE 31

(R)-N-[4-[2-[[2-Hydroxy-2-(pyridin-3-yl)ethyl]amino] ethyl]phenyl]-4-[4-(1-hydroxy-1-hexylheptyl)-5-methyl-[1,2,3]-triazol-2-yl]benzenesulfonamide and (R)-N-[4-[2-[[2-Hydroxy-2-(pyridin-3-yl)ethyl]amino]ethyl]phenyl]-4-[4-(1-(R,S)-hydroxyheptyl)-5-methyl-[1,2,3]-triazol-2-yl]benzenesulfonamide To a solution of 180 mg of (R)-N-[4-[2-[[2-Hydroxy-2-(pyridin-3-yl)ethyl]amino]ethyl]phenyl]-4-(4-methoxycarbonyl-5-methyl-[1,2,3]-triazol-2-yl)benzenesulfonamide (prepared according to the procedures outlined in examples 14–25) in 2 mL of distilled THF under argon at 0° C. was added, dropwise, 2 mL of a 2.0M solution of n-hexylmagnesium bromide in ether. After 5 min, the reaction was quenched with cautious addition of 5 mL of aqueous ammonium chloride followed by ethyl acetate extraction of the aqueous layer. The combined organic extracts were dried over sodium sulfate, filtered, and concentrated in vacuo to yield the crude products. Preparative layer chromatography (PLC) on 2×0.5 mm thick silica gel plates eluted in 9:1 (v/v) dichloromethane:methanol gave two bands A (20 mg) and B (60mg). $^1$H NMR (500 MHz, CD$_3$OD) of A: δ8.51 (d, 1H, J=2 Hz), 8.41 (dd, 1H, J=1.5, 5 Hz), 8.01 (dd, 2H, 3=2.5, 6.5Hz), 7.81 (m, 1H), 7.78 (dd, 2H, J=2.0, 9.0 Hz), 7.37 (m, 1H), 7.07;7.02 (ABq, 4H, Jab=8.5 Hz), 4.86 (s, CD3OH), 4.79 (dd, 1H, J=7.5, 8 Hz), 2.9-2.7 (m, 6H), 2.44 (s, 3H), 1.85 (m, 4H), 1.40-1.15 (m, 16H), 0.83 (t, 6H, J=7 Hz) indicating the dihexyl tertiary alcohol adduct, mass spec. expected 677 found 677. $^1$H NMR (500 MHz, CD$_3$OD) of B: 8.51 (d, 1H, J=2 Hz), 8.41 (dd, 1H, J=1.5, 5 Hz), 8.03 (d, 2H, J=9 Hz), 7.78 (d, 2H, J=9 Hz), 7.37 (dd, 1H, J=4.8, 7.7 Hz), 7.07;7.02 (ABq, 4H, Jab=8 Hz), 4.86 (s, CD3OH), 4.80 (m, 2H), 2.9-2.7 (m, 6H), 2.38 (s, 3H), 1.87 (m, 2H), 1.44 (m, 1H), 1.4-1.2 (m, 7H), 0.87 (t, 3H, J=7 Hz) indicating the mono-hexyl adduct. Mass spec expected 591 (for the hexyl ketone) found 593 (hexyl alcohol, intermediate ketone reduced by Grignard reagent in situ).

Following the procedures outlined for Examples 14–31, the compounds listed in Table 2 were prepared. The preparation of compounds of Examples 70, 73 and 80 is also provided in more detail herein below.

TABLE 2

| Example | R | Selected $^1$H NMR (CD$_3$OD) Data |
|---|---|---|
| 32 | 4-isopropylphenyl | 7.64(d, 2H, J=8.0Hz), 7.33(d, 2H, J=8.0Hz), 4.80(m, 1H), 2.95–2.70(m, 7H), 1.22(d, 6H, J=6.7Hz) |
| 33 | 4-iodophenyl, bistrifluoroacetate salt | 7.84(d, 2H, J=8.6Hz), 7.47(d, 2H, J=8.6Hz), 5.19(dd, 1H, J= 10.1, 3.0Hz), 3.40-3.20(m, 4H), 2.96(m, 2H) |
| 34 | 2-naphthyl | 8.28(s, 1H), 7.94(m, 3H), 7.72 (dd, 1H, J=8.7, 1.9Hz), 7.60(m, 2H) |
| 35 | 3-quinolinyl, bistrifluoroacetate salt | 9.01(d, 1H, J=2.3Hz), 8.76(d, 1H, 1.8Hz), 8.08(d, 1H, J=8.7 Hz), 8.04(d, 1H, J=8.0Hz), 7.93 (m, 1H), 7.73(m, 1H) |
| 36 | 4-[(N-hexyl,N-methyl-aminocarbonyl)-amino]phenyl, bistrifluoroacetate salt | 5.12(d, 1H, J=8.7Hz), 3.40-3.10 (m, 6H), 2.99(s, 3H), 2.95(m, 2H), 1.56(m, 2H), 1.31(m, 6H), 0.88 (m, 3H) |
| 37 | 4-(3-hexyl-2-imidazolidinon-1-yl)phenyl, bistrifluoroacetate salt | 5.15(m, 1H), 3.85(m, 2H), 3.53 (m, 2H), 3.40-3.15(m, 6H), 2.94 (m, 2H), 1.55(m, 2H), 1.32(m, 6H), 0.89(m, 3H). |
| 38 | 4-[(1-oxoheptyl)-amino]phenyl, bistrifluoroacetate salt | 2.35(tr, 2H, J=7.5Hz), 1.65 (quint., 2H, J=7.1Hz), 1.32(m, 6H), 0.892(tr, 3H, J=6.8Hz). |
| 39 | 4-[(1-oxo-4-phenyl-butyl)amino]phenyl, bistrifluoroacetate salt | 7.34–7.25(m, 4H), 7.15–7.05(m, 5H), 2.71(tr, 2H, J=7.7Hz), 2.36 (tr, 2H, J–7.4Hz), 1.96(m, 2H). |
| 40 | 4-[(propoxycarbonyl)-amino]phenyl | 4.07(tr, 2H, J=6.6Hz), 1.67 (sextet, 2H, J=7.0Hz).0.968(tr, 3H, J=7.4Hz). |
| 41 | 4-[[[(fur-2-ylmethyl)amino]carbonyl]amino]phenyl, | 7.40(d, 1H, J=0.9Hz), 6.32(dd, 1H, J=2.9, 1.8Hz), 6.23(d, 1H, J= 2.9Hz), 4.34(s, 2H) |

TABLE 2-continued

[Structure: 3-pyridyl-CH(OH)-CH2-NH-CH2-CH2-C6H4-NH-S(=O)2-R]

| Example | R | Selected ¹H NMR (CD₃OD) Data |
|---------|---|------------------------------|
| 42 | 4-[[[(2-phenylethyl)amino]carbonyl]amino]phenyl, bistrifluoroacetate salt | 7.38–7.02(m, 9H), 3.50–3.15(m, 6H), 2.80(m, 2H) |
| 43 | 4-[[[(2-indol-3-ylethyl)amino]carbonyl]amino]phenyl | 7.58–7.53(m, 3H), 7.42–7.30(m, 4H), 7.08–6.94(m, 7H), 3.48(tr, 2H, J=6.9Hz) 2.94(tr, 2H, J=6.8Hz). |
| 44 | 4-[[(octylamino)carbonyl]amino]phenyl, bistrifluoroacetate salt | 2.94(m, 2H), 1.51(tr, 2H, J=6.8Hz), 1.30(m, 10H), 0.884(tr, 3H, J=6.9Hz). |
| 45 | 1-[(hexylamino)carbonyl]indolin-5-yl | 7.83(d, 2H, J=9.2Hz), 7.48(m, 2H), 3.92(t, 2H, J=8.8Hz), 3.1–3.2(two overlap-ping t, 4H), 1.54 (m, 2H), 1.30(m, 6H), 0.90(t, 3H, J=6.8Hz). |
| 46 | 1-[(octylamino)carbonyl]indolin-5-yl | 7.83(d, 2H, J=9.2Hz), 7.48(m, 2H), 3.92(t, 2H, J=8.8Hz), 3.1–3.2(two overlap-ping t, 4H), 1.63 (m, 2H), 1.30(m, 10H), 0.89(t, 3H, J=6.9Hz). |
| 47 | 1-[(N-methyl-N-octylamino)carbonyl]-indolin-5-yl | 7.53(m, 2H), 6.90(d, 1H, J=8.3 Hz), 3.89(t, 2H, J=8.4Hz), 3.26 (t, 2H, J=7.6Hz), 3.04(t, 2H, J= 8.4Hz), 2.91(s, 3H), 1.60(m, 2H), 1.27(m, 10H), 0.87(t, 3H, J=6.8). |
| 48 | 1-(1-oxononyl)indolin-5-yl | 7.49(m, 2H), 8.09(d, 1H, J=9.1), 4.04(t, 2H, J=8.5), 3.07(t, 2H, J=8.5), 2.41(t, 2H, J=7.5), 1.62(m, 2H), 1.30(m, 10H), 0.88(t, 3H, J=6.8) |
| 49 | 1-(4-methylthiazol-2-yl)indolin-5-yl | 7.87(d, 1H, J=8.6Hz), 7.58(1H, dd, J=2.0, 8.6Hz), 7.52(d, 1H, J= 2.0Hz), 6.48(s, 1H), 4.08(t, 2H, J=8.7Hz), 3.25(t, 2H, J=8.7Hz), 2.30(s, 3H). |
| 50 | 1-(4-octylthiazol-2-yl)indolin-5-yl | 7.97(d, 1H, J=8.6Hz), 7.57(1H, dd, J=2.0, 8.6Hz), 7.53(d, 1H, J= 2.0Hz), 6.49(s, 1H), 4.06(t, 2H, J=8.8Hz), 3.24(t, 2H, J=8.8Hz), 2.62(t, 2H, J=7.5Hz), 1.68(m, 2H), 1.2–1.4(m, 10H), 0.88(t, 3H, J=7.0Hz). |
| 51 | 1-(4-ethyl-5-methylthiazol-2-yl)indolin-5-yl | 7.87(d, 1H, J=8.5Hz), 7.54(1H, dd, J=2.0, 8.5Hz), 7.50(d, 1H, J= 2.0Hz), 4.02(t, 2H, J=8.7Hz), 3.20(t, 2H, J=8.7Hz), 2.56(q, 2H, J=7.7Hz), 2.26(s, 3H), 1.20 (t, 3H, J=7.7Hz). |
| 52 | 4-(3-octyl-2-imidazolidinon-1-yl)phenyl | 4.78(m, 1H), 3.83(m, 2H), 3.52 (m, 2H), 3.24(t, 2H, 8Hz), 1.60–1.51(m, 2H), 1.35–1.25(m, 10H), 0.88(t, 2H, 8Hz). |
| 53 | 4-[3-(4,4,4-trifluorobutyl)-2-imidazolidinon-1-yl]phenyl, bistrifluoroacetate salt | 3.86(m, 2H), 3.54(m, 2H), 3.40–3.20(m, 6H), 2.19(m, 2H), 1.82 (quin, J=7.9Hz, 2H) |
| 54 | 4-[3-(3-phenylpropyl)-2-imidazolidinon-1-yl]phenyl, bistrifluoroacetate salt | 7.20(m, 4H), 7.10(m, 1H), 5.15 (dd, 1H, 9.6, 4Hz), 3.75(m, 2H), 3.46(m, 2H), 3.36–3.20(m, 6H), 2.95–2.91(m, 2H), 2.65(t, 2H, 8Hz), 1.90(qu, 2H, 8Hz). |
| 55 | 4-[3-(4,4,5,5,5-pentafluoropentyl)-2-imidazolidinon-1-yl]phenyl, bistrifluoroacetate salt | 3.87(m, 2H), 3.56(m, 2H), 3.40–3.20(m, 6H), 2.14(m, 2H), 1.86 (quin, J=7.8Hz, 2H) |
| 56 | 4-[3-(2-cyclohexylethyl)-2-imidazolidinon-1-yl]phenyl, bistrifluoroacetate salt | 3.82(m, 2H), 3.50(m, 2H), 2.87–2.70(m, 6H), 1.78–1.63(m, 5H), 1.41(quartet, 2H, J=7.2Hz), 1.30–1.18(m, 4H), 0.949(m, 2H). |
| 57 | 4-[3-[3-(4-chlorophenyl)propyl]-2-imidazolidinon-1-yl]phenyl | 7.19(s, 4H), 4.79(m, 1H), 3.74(m, 2H), 3.47(m, 2H), 3.30(m, 2H), 2.63(t, 2H, 7.6Hz), 1.91–1.83(m, 2H). |
| 58 | 4-(3-pentyl-2-imidazolidinon-1-yl)phenyl, bistrifluoroacetate salt | 3.82(m, 2H), 3.53(m, 2H), 2.94 (m, 2H), 1.57(quintet, 2H, J=7.4 Hz), 1.39–1.28(m, 4H), 0.916, (tr, 3H, J=7.1Hz). |
| 59 | 4-[3-(3-cyclopentylpropyl)-2-imidazolidinon-1-yl]phenyl | 3.81(m, 2H), 3.51(m, 2H), 3.23(t, J=7.3Hz, 2H), 1.78(m, 3H), 1.57 (m, 6H), 1.33(m, 2H), 1.17(m, 2H) |
| 60 | 4-[3-(2-cyclopentylethyl)-2-imidazolidinon-1-yl]phenyl, bistrifluoroacetate salt | 3.83(m.2H), 3.53(m, 2H), 2.94 (m, 2H), 1.81(m, 4H), 1.65–1.53 (m, 5H), 1.16(m, 2H). |
| 61 | 4-[3-(3-cyclohexylpropyl)-2-imidazolidinon-1-yl]phenyl | 3.83(m, 2H), 3.51(m, 2H), 3.22(t, J=7.3Hz, 2H), 1.71(m, 5H), 1.56 (m, 6H), 1.20(m, 6H), 0.88(m, 2H) |
| 62 | 4-[3-(2,2-dimethylhexyl)-2-imidazolidinon-1-yl]phenyl | 3.82(m, 2H), 3.60(m, 2H), 3.03(s, 2H), 1.28(m, 6H), 0.93(m, 3H), 0.91(s, 6H). |
| 63 | 4-(3-hexyl-2-imidazolon-1-yl)-phenyl | 6.93(d, 1H, 4Hz), 6.70(d, 1H, 4Hz), 4.79(m, 1H), 3.64(t, 2H, 8Hz), 1.71–1.64(m, 2H), !.35–1.28 (m, 6H), 0.91–0.86(m, 3H). |
| 64 | 4-[3-(4,4,4-trifluorobutyl)-2-imidazolidinon-1-yl]phenyl | 6.97(d, 1H, 3Hz), 6.73(d, 1H, 3Hz), 3.73(t, 2H, 7Hz), 2.23–2.19 (m, 2H), 1.98–1.92(m, 2H). |
| 65 | 4-(3-octyl-2-imidazolon-1-yl)-phenyl | 6.93(d, 1H, 4Hz), 6.69(d, 1H, 4Hz), 3.64(t, 2H, 7Hz), 1.70–1.63 (m, 2H), 1.33–1.23(m, 10H), 0.90–0.85(m, 3H). |
| 66 | 4-[3-(3-cyclopentylpropyl)-2-imidazolon-1-yl]phenyl | 6.93(d, 1H, 3Hz), 6.69(d, 1H, 3Hz), 3.63(t, 2H, 7Hz), 1.80–1.47 (m, 11H), 1.35–1.29(m, 2H), 1.13–1.02(m, 2H). |
| 67 | 4-(2-octyl-3-oxo-[1,2,4]-triazol-4-yl)phenyl | 8.25(s, 1H), 3.79(t, 2H, 7Hz), 1.80–1.70(m, 2H), 1.36–1.25(m, 10H), 0.91–0.86(m, 3H). |
| 68 | 4-(4-hexyl-5-tetrazolon-1-yl)phenyl | 3.98(t, 2H, J=7.1Hz), 2.9–2.7(m, 6H), 1.82(q, 2H, J=7Hz), 1.4–1.27 (m, 6H), 0.89(t, 3H, J=7Hz) |
| 69 | 4-(4-octyl-5-tetrazolon-1-yl)phenyl | 3.98(t, 2H, J=7.1Hz), 2.9–2.7(m, 6H), 1.83(m, 2H), 1.4–1.2(m, 10H), 0.87(t, 3H, J=7Hz) |
| 70 | 4-[4-(3-cyclopentylpropyl)-5-tetrazolon-1-yl]phenyl | 3.97(t, 2H, J=7.1Hz), 2.9–2.7(m, 6H), 1.9–1.7(m, 5H), 1.6(m, 1H), 1.5(m, 1H), 1.37(m, 2H), 1.07(m, 2H) |
| 71 | 4-(2-pentyloxazol-5-yl)phenyl | 7.48(s, 1H), 4.82(m, 1H), 2.92–2.70(m, 8H), 1.80(m, 2H), 1.39 (m, 4H), 0.92(m, 4H) |
| 72 | 4-(2-octyloxazol-5-yl)phenyl | 7.52(s, 1H), 5.09(m, 1H), 3.01–2.82(m, 8H), 1.77(m, 2H), 1.37–1.27(m, 10H), 0.87(m, 1H) |

TABLE 2-continued

Structure: pyridin-3-yl-CH(OH)-CH2-NH-CH2CH2-C6H4-NH-SO2-R

| Example | R | Selected ¹H NMR (CD₃OD) Data |
|---|---|---|
| 73 | 4-[2-(2-cyclopentylethyl)-oxazol-5-yl]phenyl | 7.52(s, 1H), 4.80(m, 1H), 2.94–2.70(m, 8H), 1.79(m, 5H), 1.62 (m, 2H), 1.54(m, 2H), 1.12(m, 2H) |
| 74 | 4-[(4-ethyl-5-methylthiazol-2-yl)amino]phenyl | 7.62(d, 2H, J=9Hz), 7.58(d, 2H, J=9Hz), 2.53(q, 2H, J=7.5Hz), 2.23(s, 3H), 1.18(t, 3H, J=7.5 Hz) |
| 75 | 4-[(4,5,6,7-tetrahydrobenzo-thiazol-2-yl)amino]phenyl | 7.54(d, 2H, J=9Hz), 7.48(d, 2H, J=9Hz), 2.54(m, 2H), 2.50(m, 2H), 1.75(m, 4H) |
| 76 | 4-(2-hexylimidazol-4-yl)phenyl | 7.75(s, 1H), 5.04(m, 1H), 3.29–3.20(m, 4H), 2.97–2.90(m, 4H), 1.82(m, 2H), 1.40–1.30(m, 6H), 0.9(m, 3H) |
| 77 | 4-(1-methyl-2-octylimidazol-5-yl)-phenyl | 7.92(s, 1H), 5.30(m, 1H), 4.84(s, 3H), 3.48–3.25(m, 4H), 3.05–2.95 (m, 4H), 1.80(m, 2H), 1.50–1.26 (m, 10H), 0.89(m, 3H) |
| 78 | 4-[1-methyl-2-(2-cyclopentylethyl)-imidazol-5-yl]phenyl | 7.41(s, 1H), 3.64(s, 3H), 2.96–2.68 (m, 8H), 1.90–1.79(m, 9H), 1.16 (m, 2H) |
| 79 | 4-[1-methyl-2-[2-(4-fluorophenyl)ethyl]-imidazol-5-yl]phenyl | 7.40(s, 1H), 7.10–6.95(m, 4H), 4.91(m, 1H), 3.39(s, 3H), 3.0(bs, 4H) |
| 80 | 4-(5-pentyl-[1,2,4]-oxadiazol-3-yl)phenyl | 2.96(t, 2H, J=7.6Hz), 1.84(t, 2H, J=7.4Hz), 1.39(m, 4H), 0.92(t, 3H, J=7.1) |
| 81 | 4-[5-(2-cyclopentylethyl)-[1,2,4]-oxadiazol-3-yl]phenyl | 2.98(t, 2H, J=7.5Hz), 1.84(m, 5H), 1.70–1.50(m, 4H), 1.16(m, 2H) |
| 82 | 4-(5-hexyl-[1,2,4]-oxadiazol-3-yl)phenyl | 2.96(t, 2H, J=7.5Hz), 1.84(quin, 2H, J=7.4Hz), 1.48–1.28(m, 6H), 0.90(t, 3H, J=7.0Hz) |
| 83 | 4-(5-heptyl-[1,2,4]-oxadiazol-3-yl)phenyl | 2.96(t, 2H, J=7.5Hz), 1.84(quin, 2H, J=7.0Hz), 1.46–1.26(m, 8H), 0.89(t, 3H, J=6.9Hz) |
| 84 | 4-(5-hexylthio-[1,2,4]-triazol-3-yl)phenyl | 3.11(t, 2H, J=7.3Hz), 2.98–2.84 (m, 4H), 2.76(t, 2H, J=7.3Hz), 1.65 (q, 2H, J=7.3Hz), 1.37 (q, 2H, J=7.1Hz), 1.28–1.23(m, 4H), 0.84(t, 3H, J=6.9Hz) |
| 85 | 4-[[4-(4-propylpiperidin-1-yl)-1,1-dioxo-[1,2,5]-thiadiazol-3-yl]amino]phenyl | 8.84(s, 1H), 8.75(d, 1H, J=5.07Hz), 8.46(d, 1H, J=8Hz), 7.15 & 7.08 each(d, 2H, J=8Hz), 0.92(t, 3H, J=7Hz) |
| 86 | 4-[[4-(hexylmethylamino)-1,1-dioxo-[1,2,5]-thiadiazol-3-yl]amino]phenyl | 7.15(d, 2H, J=8.5Hz), 7.12(d, 2H, J=8.5Hz), 5.19(dd, 1H, 3.1Hz, 9Hz), 2.93(m, 2H), 0.90(t, 3H, 6.8Hz) |
| 87 | 4-[[4-(heptylmethylamino)-1,1-dioxo-[1,2,5]-thiadiazol-3-yl]amino]phenyl | 7.16(d, 2H, J=8.8Hz), 7.11(d, 2H, J=8.8Hz), 5.01(dd, J=3.2Hz, 9.9Hz), 2.92(m, 2H), 1.68(m, 2H) |
| 88 | 4-(1-octyl-2,4-imidazolidinedion-3-yl)phenyl | 4.09(s, 2H), 3.41(t, 2H, 7hz), 1.65–1.56(m, 2H), 1.30–1.25(m, 10H), 0.91–0.86(m, 3H). |
| 89 | 4-[3-(3-nitrophenyl)-5-pyrazolon-1-yl]phenyl | 8.55(t, 1H, J=1.9Hz), 8.47(d, 1H, J=2.0Hz), 8.37(dd, 1H, J=3.2Hz), 8.14(d, 2H, J=8.9Hz), 8.08(t, 2H, J=8.5Hz), 7.74(d, 3H, J=8.9Hz), 7.56(t, 1H, J= |

TABLE 2-continued

Structure: pyridin-3-yl-CH(OH)-CH2-NH-CH2CH2-C6H4-NH-SO2-R

| Example | R | Selected ¹H NMR (CD₃OD) Data |
|---|---|---|
| | | 8.0Hz), 7.33(dd, 1H, J=4.8Hz), 7.04 (dd, 4H, J=6.6Hz), 4.75(t, 1H, J=2.1Hz), 2.83–2.69(m, 6H) |

EXAMPLE 70

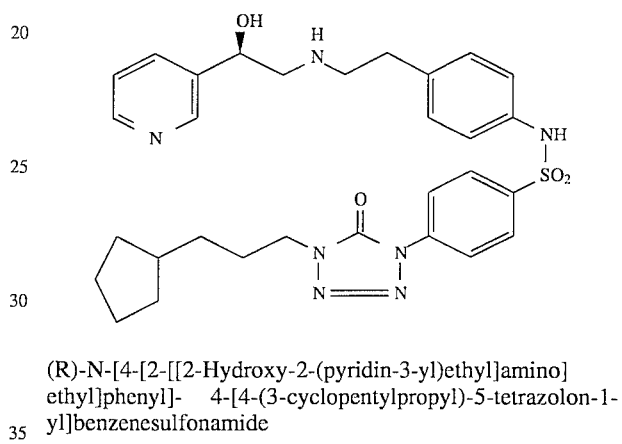

(R)-N-[4-[2-[[2-Hydroxy-2-(pyridin-3-yl)ethyl]amino]ethyl]phenyl]- 4-[4-(3-cyclopentylpropyl)-5-tetrazolon-1-yl]benzenesulfonamide A. Preparation of 3-Cyclopentyl-1-Iodopropane To a solution of 5 g of commercially available 3-cyclopentyl-1-propanol in 20 mL of dichloromethane at 0° C. was added 5 mL of dry triethylamine and 5 g of methanesulfonyl chloride. The mixture containing a heavy white precipitate of triethylamine hydrochloride was stirred an additional 5 min before 70 mL of diethyl ether was added. The mixture was filtered through a glass fritted funnel to remove the precipitate and the filtrate was concentrated in vacuo to afford the mesylate. To this was added 10 g of sodium iodide and 30 mL of acetone. After 18 h at room temperature, the dark slurry was dissolved in water and extracted with dichloromethane. The extracts were combined and washed with excess aqueous sodium sulfite and dried over magnesium sulfate. Filtration and concentration of the dichloromethane solution gave 8 g of the title compound: ¹H NMR (CDCl₃) δ 3.19 (t, 2H, J=7.1 Hz), 1.85 (m, 3H), 1.77 (m, 2H), 1.61 (m, 2H), 1.52 (m, 2H), 1.41 (m, 2H), 1.09 (m, 2H).

B. Preparation of 4-(3-Cyclopentylpropyl)-1-Phenyl-5-Tetrazolone

To a solution of 600 mg of 1-phenyl-5-tetrazolone (for the synthesis of this compound see: Horwitz, J. P.; Fisher, B. E.; Tomasewski, A. J. *J Amer Chem Soc* 1959, 81, 3076) in 2 mL of N,N-dimethylformamide (DMF) was added 280 mg of powdered 85% potassium hydroxide followed by 870 mg of 3-cyclopentyl-1-iodopropane from Step A. The mixture was stirred at 80° C. for 18 h and then quenched by addition of water. The product was extracted with dichloromethane and purification by flash chromatography on silica gel (9:1 hexane:ethyl acetate) afforded 830 mg of the title compound: $^1$H NMR (CDCl$_3$) δ7.96 (d, 2H, J=8.5 Hz), 7.50 (t, 2H, J= 7.5 Hz), 7.37 (t, 1H, J=7.5 Hz), 4.02 (t, 2H, J=7.1 Hz), 1.90 (m, 3H), 1.79 (m, 2H), 1.61 (m, 2H), 1.53 (m, 2H), 1.41 (m, 2H), 1.10 (m, 2H).

C. Preparation of 4-(3-cyclopentylpropyl)-1-(4-nitrophenyl)-5-tetrazolone

To a solution of 7 g of 4-(3-cyclopentylpropyl)-1-phenyl-5-tetrazolone from Step B in 50 mL of dry acetonitrile was added, in one portion, 4.2 g of 95% nitronium tetrafluoroborate with rapid stirring. The reaction mixture was stirred at room temperature for 30 min before an additional 2 g of nitronium tetrafluoroborate was added to react with detectable starting material. The mixture was stirred an additional 30 min before addition of water and extraction with ethyl acetate. The combined ethyl acetate extracts were washed with aqueous sodium bicarbonate and dried over magnesium sulfate. Filtration and concentration of the filtrate gave an orange oil. Flash chromatographic separation on silica gel using 4:1 hexane:ethyl acetate afforded 4.6 g of the para-nitrophenyl title compound as a solid (Rf=0.7) and 2 g of the ortho-nitrophenyl product as an oil (Rf=0.2): Para-nitro product $^1$H NMR (CDCl$_3$) δ8.35 (ABq, 4H, Jab=9.3 Hz), 4.06 (t, 2H, J=7.1 Hz), 1.93 (m, 3H), 1.80 (m, 2H), 1.63 (m, 2H), 1.54 (m, 2H), 1.43 (m, 2H), 1.10 (m, 2H); Ortho-nitro product 1H NMR (CDCl$_3$) δ5 8.13 (dd, 1H, J=1.1, 8.3 Hz), 7.81 (dt, 1H, J=1.3, 7.8 Hz), 7.72 (dd, 1H, J=1.1, 8.0 Hz), 7.67 (dt, 1H, J=1.4, 7.6 Hz), 4.03 (t, 2H, J=7.1 Hz), 1.92 (m, 3H), 1.80 (m, 2H), 1.61 (m, 2H), 1.53 (m, 2H), 1.42 (m, 2H), 1.10 (m, 2H).

D. Preparation of 1-(-Aminophenyl)-4-(3-Cyclopentylpropyl)-5-Tetrazolone

To a solution of 6.23 g of 4-(3-cyclopentylpropyl)-1-(4-nitrophenyl)-5-tetrazolone from Step C in 250 mL of ethanol was added 1.8 g of 10% palladium on carbon. The mixture was stirred under a 1 atmosphere pressure of hydrogen provided by a balloon for 3–6 h. The catalyst was then removed by filtration through a plug of silica gel. The tiltrate was concentrated in vacuo to yield 5.52 g of the title compound as a waxy solid: $^1$H NMR (CDCl$_3$) δ5 7.64 (d, 2H, J=8.9 Hz), 6.77 (d, 2H, J=8.9 Hz), 4.01 (t, 2H, J=7.3 Hz), 3.83 (br s, 2H), 1.90 (m, 3H), 1.79 (m, 2H), 1.60 (m, 2H), 1.54 (m, 2H), 1.41 (m, 2H), 1.10 (m, 2H).

E. Preparation of 4-[4-(3-Cyclopentylpropyl)-5-Tetrazolon-1-Yl]-Benzenesulfonyl Chloride To a solution of 32 mL of concentrated hydrochloric acid and 8 mL of glacial acetic acid at −20° C. was added 5.42 g of powdered 1-(4-aminophenyl)-4-(3-cyclopentylpropyl)-5-tetrazolone from Step D. The mixture was stirred for 5 min before a solution of 1.6 g of sodium nitrite in 10 mL of water was added at a rate which kept the temperature from rising above −10° C. The diazonium salt mixture was stirred an additional 40 min at −20° C. and then added in one portion to a solution of 32 mL of glacial acetic acid containing 690 mg of copper (I) chloride saturated with sulfur dioxide at 0° C. The resultant reaction mixture instantly changed in color from a dark green with nitrogen evolution to a lime green slurry as time progressed. The reaction mixture was allowed to warm from 0° C. to room temperature over 50 min. The mixture was then poured into ice-water and extracted with ethyl acetate. The combined organic extracts were washed once with cold water, dried over magnesium sulfate, filtered, and concentrated in vacuo to remove acetic acid. The crude sulfonyl chloride was purified by flash chromatography (silica gel, dichloromethane) to yield 3.4 g of the title compound as a white solid: 1H NMR (CDCl$_3$) δ8.37 (d, 2H, J=9.1 Hz), 8.20 (d, 2H, J=8.6 Hz), 4.06 (t, 2H, J=7.1 Hz), 1.93 (m, 3H), 1.81 (m, 2H), 1.62 (m, 2H), 1.55 (m, 2H), 1.41 (m, 2H), 1.11 (m, 2H).

F. Preparation of (R)-N-[4-[2-[N-(1,1-Dimethylethoxycarbonyl)-N-[2-Hydroxy-2-(Pyridin-3-Yl)Ethyl]Amino]Ethyl]Phenyl]-4-[4-(3-Cyclopentylpropyl)-5-Tetrazolon-1-Yl]Benzenesulfonamide To 2.84 g of the product from Example 18 was added 30 mL of dichloromethane and 3.01 g of 4-[4-(3-cyclopentylpropyl)- 5-tetrazolon-1-yl]benzenesulfonyl chloride from Step E followed by 5 mL of dry pyridine. The orange solution was stirred at room temperature for 12 h and TLC showed no starting material left. The mixture was concentrated to dryness and the residual solid foam was taken up in dichloromethane and purified by flash chromatography on silica gel (4:6 acetone:hexane) 3 times to obtain 3.1 g of the title compound: 1H NMR (CD$_3$OD) δ8.46 (d, 1H, J=9.2 Hz), 8.41 (m, 1H, J=4.8 Hz), 8.07 (d, 2H, J=6.9 Hz), 7.86 (d, 2H, J=8.3 Hz), 7.80 (dd, 1H, J=6.9, 24.3 Hz), 7.40 (m, 1H, J=5.5 Hz), 7.02 (m, 4H), 4.85 (m, 1H), 4.01 (t, 2H, J=7.1 Hz), 3.43-3.10 (m, 4H), 2.72 (m, 2H), 1.87 (m, 3H), 1.78 (m, 2H), 1.62 (m, 2H), 1.53 (m, 2H), 1.30 (d, H), 1.10 (m, 2H).

G. Preparation of (R)-N-[4-[2-[[2-hydroxy-2-(pyridin-3-yl)ethyl]amino]-ethyl]phenyl]-4-[4-(3-cyclopentylpropyl)-5-tetrazolon-1-yl]benzene-sulfonamide A 3.1-g sample of Boc derivative from Step F was dissolved in 50 mL of methanol and 10 mL of concentrated hydrochloric acid. The solution was heated at 50° C. for 1 h. A precipitate of the hydrochloride salt was obtained. This was cooled and basified with excess sodium bicarbonate solution and extracted with ethyl acetate. The combined extracts were dried over sodium sulfate, filtered, and concentrated in vacuo. The residual solid was purified by flash chromatography (silica gel, 9:1 dichloromethane:methanol) to yield 2.37 g of the title compound as a glass: $^1$H NMR (CD$_3$OD) 15 8.51 (d, 1H, J=2.1 Hz), 8.42 (dd, 1H, J=1.6, 4.8 Hz), 8.09 (d, 2H, J=8.9 Hz), 7.86 (d, 2H, J= 8.7 Hz), 7.81 (d, 1H, J=7.7 Hz), 7.39 (dd, 1H, J=4.6, 7.8 Hz), 7.05 (ABq, 4H, Jab=8.5 Hz), 4.79 (m, H), 3.97 (t, 2H, J=7.1 Hz), 2.90-2.70 (m, 6H), 1.90-1.74 (m, 5H), 1.61 (m, 2H), 1.53 (m, 2H), 1.37 (m, 2H), 1.07 (m, 2H).

EXAMPLE 70A

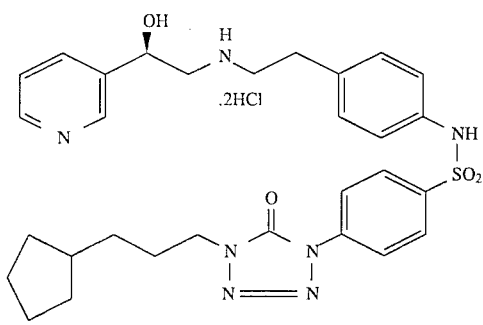

(R)-N-[4-[2-[[2-Hydroxy-2-(pyridin-3-yl)ethyl]amino]
ethyl]phenyl]-4-[4-(3-cyclopentylpropyl)-5-tetrazolono
1-yl]benzenesulfonamide dihydrochloride To 1.56 g of (R)-N-[4-[2-[[2-hydroxy-2-(pyridin- 3-yl)ethyl]amino]ethyl]phenyl]-4-[4-(3-cyclopentylpropyl)-5-tetrazolon- 1-yl]benzenesulfonamide, the free base from Example 70, was added 75 mL of methanol and 3 mL of 2 N hydrochloric acid. The solution was concentrated to dryness in vacuo and the residual salt was redissolved in 30 mL of methanol and 100 mL of boiling ethanol. Upon cooling (ice bath), crystallization occurred to afford 1.15 g of the title compound as a white crystalline solid: mp 198°–202° C. (decomp.); $^1$H NMR (CD$_3$OD) δ8.99 (br s, 1H), 8.86 (d, 1H, J=5.5 Hz), 8.74 (d, 1H, J=8.0Hz), 8.14 (dd, 1H, J=5.5, 8.0 Hz), 8.08 (d, 2H, J=9 Hz), 7.89 (d, 2H, J=9 Hz), 7.15 (ABq, H, Jab=8.4 Hz), 5.35 (dd, 1H, J=2.5, 9.5 Hz), 4.00 (t, 2H, J=7.1 Hz), 3.47 (dd, 1H, J=3.0, 12.8 Hz), 3.35-3.22 (m, 3H), 2.99 (m, 2H), 1.87 (m, 3H), 1.79 (m, 2H), 1.61 (m, 2H), 1.53 (m, 2H), 1.39 (m, 2H), 1.10 (m, 2H).

EXAMPLE 73

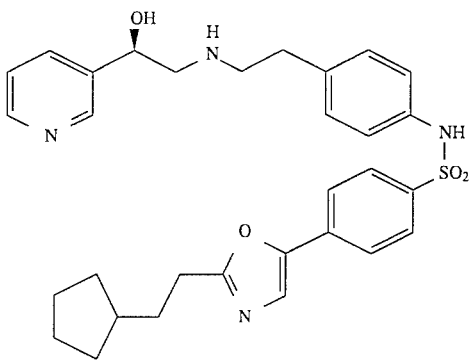

(R)-N-[4-[2-[[2-Hydroxy-2-(pyridin-3-yl)ethyl]amino]
ethyl]phenyl]-4-[2-(2-cyclopentylethyl)oxazol-5-yl]benzenesulfonamide

A. Preparation of 2-Azido-1-Phenylvinyl 3-Cyclopentylpropionate

To a stirred solution of α-azidoacetophenone (3.37 g, 20.9 mmol) in dry THF (50 mL) was added a solution of LDA (2.0 M in cyclohexane, 12.5 mL, 25 mmol) at –78° C. under nitrogen dropwise. After the reaction mixture was stirred for 1 h, a solution of 3-cyclopentylpropionyl chloride (5.04 g, 31.35 mmole, 1.5 eq.) was added to the dark red mixture, and after 10 min, the mixture was slowly warmed to room temperature. Stirring was continued for 1 h and the resultant yellow mixture was poured into water and extracted with ethyl acetate (3×50 mL). The combined organics were washed with water and brine, dried over magnesium sulfate, and filtered. Evaporation of solvent followed by column chromatography on silca gel (eluent: 2:1 ethyl acetate:hexanes) gave 4.0 g (71.5%) of the title compound: $^1$H NMR (400 MHz, CDCl$_3$) ε 7.32-7.26 (m, 5H), 6.53 (s, 1H), 2.58 (t, 2H, J=7.5 Hz), 1.89-1.70 (m, 5H), 1.65-1.40 (m, 4H), 1.2 (m, 2H).

B. Preparation of 2-(2-Cyclopentylethyl)-5-Phenyloxazole

To a stirred solution of 2-azido-1-phenylvinyl 3-cyclopentylpropionate from Step A (4.0 g, 14 mmol) in dry cyclohexane (10 mL) was added triethyl phosphite (12 g, 74 mmol) dropwise. After stirring at room temperature for 1 h, the mixture was heated at 90° C. in an oil bath under nitrogen for 6 h. The mixture was cooled and chromatographed on a silica gel column (eluent: 1:5 ethyl acetate:hexanes) to give 1.57 g (46.6%) of the title compound as a white solid: $^1$H NMR (400 MHz, CDCl$_3$) δ7.59 (dt, 2H, J=2.0,8.2 Hz), 7.38 (dr, 2H, J=1.4, 8.0 Hz), 7.29 (tt, 1H, J=2.0, 8.0 Hz), 7.19 (s, 1H), 2.82 (t, 2H, 7.5 Hz), 1.89-1.75 (m, 5H), 1.61-1.47 (m, 4H), 1.11 (m, 2H).

C. Preparation of 4-[2-(2-Cyclopentylethyl)Oxazol-5-Yl] Benzenesulfonyl Chloride Neat chlorosulfonic acid (2 mL) was added to 2-( 2-cyclopentylethyl)-5-phenyloxazole from Step B (500 mg, 2.07 mmol) at room temperature under nitrogen with stirring. To this brown solution was added sodium chloride (100 mg) in portions and then the mixture was heated at 50° C. in an oil bath. After 2 h at 50° C., the mixture was poured onto ice-water and extracted with ethyl acetate (3×10 mL). The combined organics were washed with saturated aqueous sodium bicarbonate solution, water, and brine, dried over sodium sulfate, and evaporated. The brown residue was chromatogaphed on silica gel (eluent: 2:3 ethyl acetate:hexanes) to give 500 mg (76.9%) of the title compound as an off-white solid: 1H NMR (400 MHz, CDCl$_3$) δ 8.05 (d, 2H, J=8.2 Hz), 7.81 (d, 2H, J=8.2 Hz), 7.45 (s, 1H), 2.85 (t, 2H, 7.5 Hz), 1.90-1.75 (m, 5H), 1.70-1.48 (m, H), 1.12 (m, 2H).

D. Preparation of (R)-N-[4-[2-[N-(1,1-Dimethylethoxycarbonyl)-N-[2-Hydroxy-2-(Pyridin-3-Yl)Ethyl]Amino]Ethyl] Phenyl]-4-[2-(2-Cyclopentylethyl)Oxazol-5-yl]Benzenesulfonamide To a solution of amine from Example 18 (456 mg, 1.28 mmol) in dry methylene chloride (10 mL) was added pyridine (316 mg, 4 mmol) followed by a solution of 4-[2-(2-cyclopentylethyl)oxazol- 5-yl]benzenesulfonyl chloride (420 mg, 1.34 mmol) from Step C at room temperature under nitrogen. After stirring 12 h, the solvent was removed under reduced pressure and the product was isolated by column chromatography on silica gel (eluent: 5:95 methanol:methylene chloride) to give 750 mg (88.8%) of the title compound as a white solid: 1H NMR (400 MHz, CDCl$_3$) δ8.48 (bs, 2H), 7.72 (d 2H, J=8 Hz), 7.64 (m, 1H), 7.6 (d. 2H, J=8 Hz), 7.3, (s, 1H), 7.26 (m, 1H), 6.98 (bs, 4H), 6.60 (bs, 1H), 4.85 (m, 1H), 3.42-3.20 (m, 4H), 2.8 (t, 2H, J=7.5 Hz), 2.63 (m, 2H), 1.82-1.76 (m, 5H), 1.62-1.48 (m, 4H), 1.12 (m, 2H).

E. Preparation of (R)-N-[4-[2-[[2-Hydroxy-2-(Pyridin-3-Yl)Ethyl]Amino]-Ethyl]Phenyl]-4-[2-(2-Cyclopentylethyl)Oxazol-5-Yl]Benzenesulfonamide (R)-N-[4-[2-[N-(1,1-dimethylethoxycarbonyl)-N-[2-hydroxy-2-(pyridin-3-yl)ethyl]amino]ethyl]phenyl]-4-[2-(2-cyclopentylethyl)oxazol_ 5-yl]benzenesulfonamide (740 mg, 1.12 mmol) from Step D was treated with freshly prepared methanolic hydrogen chloride (5 mL) overnight. The solvent was removed under reduced pressure and the free base was isolated by column chromatography on silica gel (eluent: 1:9 10% ammonium hydroxide in methanol:methylene chloride) to afford the title compound as a white solid (560 mg, 89.3%): 1H NMR (500 MHz, CD$_3$OD) δ8.52 (d, 1H, J=2.0 Hz), 8.43 (dd, 1H, J=1.5, 5 Hz), 7.81 (bd, H), 7.77 (d, 2H, J=8.5 Hz), 7.74 (d, 2H, J=8.5 Hz), 7.52 (s, 1H), 7.38 (dd, 1H, J=5, 7.5 Hz), 7.08 (d, 2H, J = 8.5 Hz), 7.02 (d, 2H, J=8.5 Hz), 4.80 (m, 1H), 2.94-2.70 (m, 8H), 1.79 (m, 5H), 1.62 (m, 2H), 1.54 (m, 2H), 1.12 (m, 2H).

EXAMPLE 80

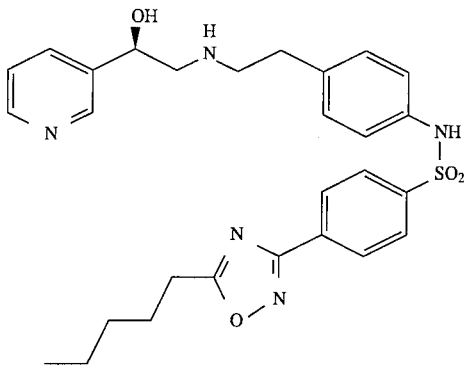

(R)-N-[4-[2-[[2-Hydroxy-2-(pyridin-3-yl)ethyl]amino]ethyl]phenyl]-4-( 5-pentyl-[1.2.4]-oxadiazol- 3-yl)benzensulfonamide

A. Preparation of (R)-N-[4-[2-[N-(1,1-Dimethylethoxycarbonyl)-N-[2-Hydroxy-2-(Pyridin-3-Yl)ethyl]Amino]Ethyl]Phenyl]- 4-Cyano-Benzensulfonamide To a solution of 780 mg (2.18 mmol) of amine from Example in 10 mL of methylene chloride was added 0.16 mL of pyridine and 450 mg of 4-cyanobenzenesulfonyl chloride. The reaction mixture was stirred at room temperature overnight. TLC (acetone 25%, methylene chloride 5%) on silica gel indicated the formation of a major fast moving (rf 0.48) spot. Purification by flash chromatography (silica gel, 25% acetone/dichloromethane) gave 716 mg of the title compound as a white solid: $^1$H NMR (400 MHz, CDCl$_3$) δ8.53-8.44 (m, 2H), 7.78 (d, J=8.7 Hz, 2H), 7.72-7.68 (m, 1H), 7.67 (d, J=8.7 Hz, 2H), 7.3-7.23 (m, 1H), 7.1-6.9 (m, 4H), 4.8 (m, 1H), 3.5-2.6 (m, 6H), 1.42 (s, 9H).

B. Preparation of (R)-N-[4-[2-[N-(1,1-Dimethylethoxycarbonyl)-N-[2-Hydroxy-2-(Pyridin-3-Yl)Ethyl]Amino] Ethyl]Phenyl]-4-(Aminooximidomethyl)Benzensulfonamide The cyano compound from Step A (250 mg), 175 mg of hydroxylamine hydrochloride, and 414 mg of finely ground potassium carbonate were suspended in 10 mL of ethanol and heated at reflux overnight. TLC (acetone/methylene chloride 40:60) indicated the formation of a new low rf product (rf 0.18). The mixture was filtered. The tiltrate was concentrated to give the title compound, which was used without further purification: 1H NMR (400 MHz, CDCl$_3$) δ8.42-8.35 (m, 2H), 7.62 (m, 1H), 7.54 (s, 4H), 7.18 (m, 1H), 6.95-6.8 (m, 4H), 5.03 (br s, 2H), 4.73 (m, 1H), 3.25-3.0 (m, 4H), 2.6-2.5 (m, 2H), 1.30 (s, 9H).

C, Preparation of (R)-N-[4-[2-[[2-Hydroxy-2-(Pyridin-3-Yl)Ethyl]Amino]Ethyl]Phenyl]-4-(5-Pentyl-[1,2,4]-Oxadiazol- 3-Yl)Benzensulfonamide.

To a solution of 111 mg of amidoxime from Step B in 0.5 mL of pyridine was added 0.028 mL of hexanoyl chloride. The reaction mixture was stirred for 1.5 hours. TLC analysis indicated that a new spot more mobile than the amidoxime formed (rf 0.67, 4:6 acetone:methylene chloride). Stirring was continued overnight until the reaction was complete by TLC analysis, and then the mixture was heated at reflux for 2 hours. A new, more mobile spot was evident by TLC (rf .80, 4:6 acetone:methylene chloride). The pyridine was distilled off and the residue purified by flash chromatography (4:6 acetone:methylene chloride). The resultant intermediate was deprotected by stirring with 2 mL of 1:1 TFA/methylene chloride for 30 min. The volatile portion was distilled off and the residue treated twice with methanol/ammonium hydroxide solution (9/1). The residue left after evaporation was purified by flash chromatography on silica gel (90/9/1 methylene chloride-methanol-conc. ammonium hydroxide) to yield 61.3 mg of the title compound: $^1$H NMR (400 MHz, CD$_3$OD) δ 8.51 (d, J=2.0, 1H), 8.42 (dd, J=1.7, 4.9 Hz, 1H), 8.13 (d, J=8.7, 2H), 7.85-7.80 (m, 1H), 7.83 (d, J=8.7, 2H), 7.38 (m, H), 7.09 (d, J=8.6, 2H), 7.02 (d, J=8.6, 2H), 4.79 (m, 1H), 2.96 (t, J=7.6 Hz, 2H), 2.8-2.7 (m, 6H), 1.84 (m, 2H), 1.39 (m, 4H), 0.92 (t, J=7.1 Hz, 3H).

Starting with commercially available (R)-styrene epoxide and following the procedures outlined for Examples 17,18 and 25, the compounds listed in Table 3 were prepared.

TABLE 3

| Example | R | Selected $^1$H NMR (CD$_3$OD) Data |
|---|---|---|
| 90 | 4-iodophenyl, trifluoroacetate salt | 7.84(d, 2H, J=8.6Hz), 7.45(d, 2H, J=8.5Hz) |
| 91 | 2-naphthyl, trifluoroacetate salt | 8.31(s, 1H), 7.96–7.90(m, 3H), 7.74(dd, 1H, J=1.8, 8.7Hz), 7.63 (t, 1H), 7.58(t, 1H) |
| 92 | 3-quinolinyl, trifluoroacetate salt | 9.01(d, 1H, J=2.2Hz), 8.75(d, 1H, J=2.1Hz), 8.07(d, 1H, J=8.4 Hz), 8.03(d, 1H, J=8.3Hz), 7.92 (t, 1H, J=7.0Hz), 7.72(t, 1H, J= 7.1Hz) |

EXAMPLE 93

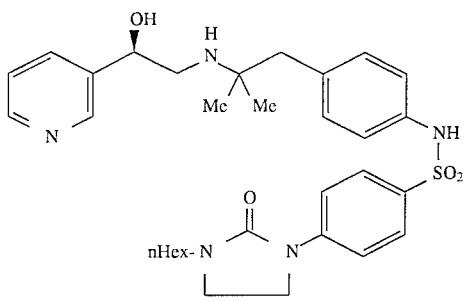

(R)-N-[4-[2-[[2-Hydroxy-2-(pyridin-3-yl)ethyl]amino]-2-methylpropyl]-phenyl]-4-(3-hexyl-2-imidazolidinon-1-yl)benzenesulfonamide A solution of pyridine epoxide (160mg,1.32 mmol) from example 16 and 4-amino-a,a-dimethylphenethylamine (1 .2 g, 7.3 mmol), prepared according to J. Biol. Chem. 1981, 256, 11944–50, in methanol (8 ml) was warmed at reflux for 16 hours. After cooling, the reaction mixture was concentrated and purified by flash chromatography (silica gel, 95:5 $CH_2Cl_2$: 10% $NH_4OH/CH_3OH$) to give 23 mg (0.080 mmol) of product as an oil.

The above product (18 mg, 0.063 mmol) was dissolved in $CH_2Cl_2$ (1 mL) and pyridine (0.05 mL). The resulting solution was cooled to 0° C. and treated with 4-(3-hexyl-2-imidazolidinon-1-yl)benzenesulfonyl chloride (22 mg, 0.063 mmol). The mixture was allowed to stir at 0° C. for hours and was then purified by flash chromatography (silica gel, 95:5 $CH_2Cl_2$:10% $NH_4OH/CH_3OH$) to give the desired product (21 mg, 0.035 mmol) as an oil: 1HNMR (CD3OD) δ 8.53 (s, 1H), 8.44 (d, 1H, J=5.0), 7.83 (d, 1H, J=7.9), 7.63 (m, 4H), 7.40 (dd, 1H, J=5.0, 7.9), 6.98 (m, 4H), 4.72 (dd, 1H, J=4.0, 8.4), 3.80 (m, 2H), 3.49 (m, 2H), 3.22 (t, H, J=7.2), 2.78 (m, 2H), 2.62 (m, 2H), 1.55 (m, 2H), 1.31 (m, 6H), 1.01 (s, 3H), 0.99 (s, 3H), 0.89 (m, 3H).

Following the procedure outlined above, the compounds in Table 4 were prepared.

TABLE 4

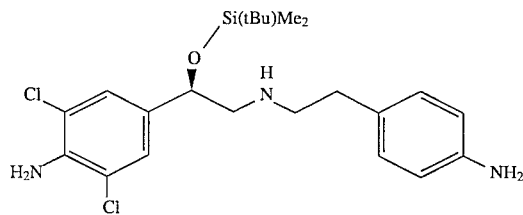

| Example | R | Selected $^1$H NMR (CD$_3$OD) Data |
|---|---|---|
| 94 | 4-iodophenyl | 7.82(d, 2H, J=8.6), 7.42(d, 2H, J=8.6) |
| 95 | 4-[[(hexylamino)carbonyl]amino]phenyl | 7.55(d, 2H, J=8.8), 7.42(d, 2H, J=8.8), 3.11(t, 2H, J=7.0), 1.49(m, 2H), 1.30(m, 6H), .089(m, 3H) |

EXAMPLE 96

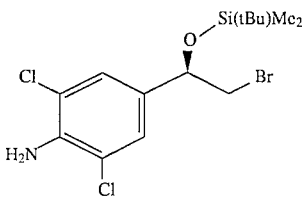

(R)-4-amino-α-(bromomethyl)-3,5-dichlorobenzenemethanol, dimethyl-1,1-dimethylethylsilyl ether A solution of t-butyldimethylsilyl chloride (1.67 g, 11.1 mmol) in DMF (15 mL) was added slowly to a stirred solution of (R)- 4-amino-α-(bromomethyl)-3,5-dichlorobenzenemethanol (2.1 g, 7.4 mmol, see Judkins, et. al, European Patent Application 0 460 924) and imidazole (0.75 g, 11.1 mmol) in DMF (6 mL) with an ice-water bath cooling. After being stirred at RT for 3h, the reaction mixture was poured into water (300 mL) and the product was extracted with ether. The organic phase was washed with saturated aqueous sodium bicarbonate solution, brine, dried-(MgSO$_4$) and evaporated to dryness. The crude product was purified on silica (95/5 hexane/ethyl acetate) to give the title compound (2.73 g, 93% $^1$H NMR (400 MHz, CDCl$_3$) δ7.14 (s, 2H), 4.67 (dd, 1H, J=2.1, 6.4 Hz), 3.33 (m, 2H), 0.87 (s, 9H), 0.89(s, 6H)

EXAMPLE 97

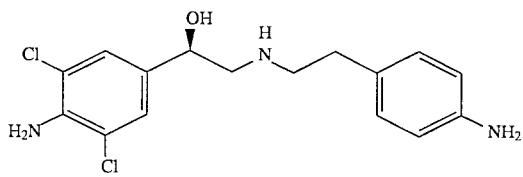

(R)-N-[2-[4-(Aminophenyl)]ethyl]-2-[(dimethyl- 1,1-dimethylethyl-silyl)oxy]-2-(4-amino-3,5-dichlorophenyl)ethylamine O-TBDMS bromo compound from Example 96 (2.73 g, 6.86 mmol) was dissolved in CH$_3$CN (50 mL) and 4-aminophenethylamine (1.86 g, 13.72 mmol) was added, followed by the addition of N,N'-diisopropylethylamine (3.58 mL, 20.6 mmol) and sodium iodide (1.03 g, 6.86 mmol). After being heated at reflux for 48 h, the reaction mixture was concentrated and the residue chromatographed on silica (50/50 ethyl acetate/hexane) to provide the title compound (2.3 g, 75 %): 1H NMR (400 MHz, CDCl$_3$) δ7.08 (s, 2H), 6.94 (AA', 2H, J=8.4 Hz), 6.60 (BB', 2H, J=8.4 Hz), 4.63 (m, 1H), 4.37 (s, 2H), 3.53 (br s, 2H), 2.87-2.60 (m, 6H), 0.80 (s, 9H),-0.03 (s, 6H)

EXAMPLE 98

(R)-N-[2-[4-(Aminophenyl)]ethyl]-2-hydroxy-2-(4-amino-3,5-dichlorophenyl)ethylamine To a stirred solution of silyl compound from Example 97 (2.2 g, 4.8 mmol) in THF (20 mL) at RT was added tetrabutylammonium fluoride (10 mL of 1.0 M solution in THF) in one portion. After being stirred at RT for 2h, the reaction mixture was concentrated and chromatographed on silica (10/90 $CH_3OH/CH_2Cl_2$) to give the title compound (1.59 g, 97 %): $^1H$ NMR (400 MHz, $CD_3OD$) δ7.15 (s, 2H), 6.92 (AA', 2H, J=8.3 Hz), 6.60 (BB', 2H, 8.3 Hz), 4.58 (m, 1H), 2.83-2.65 (m, 6H)

EXAMPLE 99

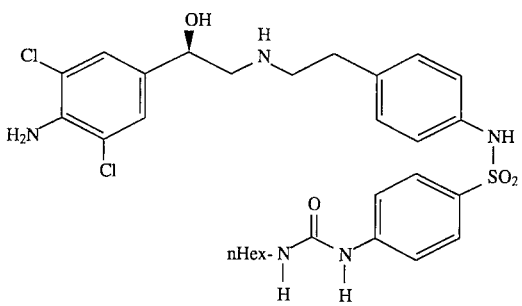

(R)-N-[4-[2-[[2-Hydroxy-2-(4-amino- 3,5-dichlorophenyl)ethyl]amino]-ethyl]-phenyl]-4-(hexylaminocarbonylamino)benzenesulfonamide Following the procedure outlined in Example 18 and 25, the title compound was prepared from the aniline derivative from Example 98: NMR (400 MHz, $CD_3OD$) 7.57 (AA', 2H, J=2.7 Hz), 7.42 (BB', 2H, J=2.7 Hz), 7.16 (s, 2H), 7.04 (AA', 2H, J=2.0 Hz), 7.00 (BB', 2H, J=2.0 Hz), 4.58 (t, 1H, j=7.1 Hz), 3.14 (t, 1H, J=7.0 Hz), 2.80 (m, 2H), 2.73 (m, 4H), 1.49 (m, 2H), 1.32 (m, 6H), 0.90 (t, 3H, J=6.7 Hz). ESI MS m/z 622 (M).

Following the procedure outlined in Examples 96–99, the compounds in Table 5 were prepared.

TABLE 5

| Example | R | Selected $^1H$ NMR ($CD_3OD$) Data |
|---|---|---|
| 100 | 1-[(octylamino)carbonyl]-indolin-5-yl | 7.82(d, 1H, J=9.2Hz), 7.47(m, 2H), 3.93(t, 2H, J=9.0Hz), 3.18 (m, 4H), 1.53(m, 2H), 1.31(m, 10H), 0.88(t, 3H, J=7.1Hz) |
| 101 | 4-(3-hexyl-2-imidazolidinon-1-yl)phenyl | 7.68–7.60(AA'BB', 4H), 3.82(t, 2H, J=6.2Hz), 3.52(t, 2H, J=6.2Hz), 3.30(t, 2H, J=6.0Hz), 1.54(m, 2H), 1.31(m, 6H), 0.89(t, 3H J=6.0Hz) |
| 102 | 4-(3-octyl-2-imidazolidinon-1-yl)phenyl | 7.65–7.60(AA'BB', 4H), 3.82(t, 2H, J=6.2Hz), 3.52(t, 2H, J=6.2Hz), 3.29(t, 2H, J=6.0Hz), 1.54(m, 2H), 1.30(m, 10H), 0.87(t, 3H, J=6.1HZ) |

EXAMPLE 103

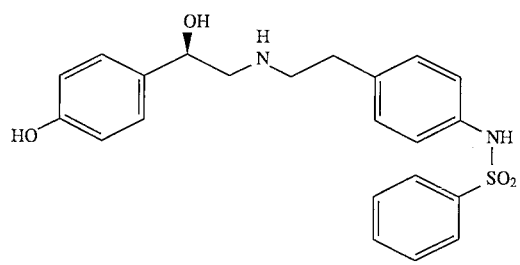

(R)-N-[4-[2-[[2-Hydroxy-2-(4-hydroxyphenyl)ethyl]amino]ethyl]phenyl]-benzenesulfonamide A solution of 5 g of 4-aminophenethyl alcohol in 50 mL of DMF was silylated with 5.5 g of t-butyldimethylsilyl chloride (TBDMS-Cl) and 2.5 g of imidazole overnight at room temperature. Extraction of the product following an aqueous ammonium chloride workup afforded 6.6 g of the O-TBDMS ether. This aniline derivative was then coupled to benzenesulfonyl chloride in pyridine:dichloromethane to give the sulfonamide in greater than 80% yield after chromatographic purification. The TBDMS group of the sulfonamide was removed with methanolic HCl at room temperature for 30 min. The crude alcohol was oxidized to the corresponding carboxylic acid with Jones reagent in acetone (RT 30 min, ethyl acetate extraction).

To a solution of 180 mg of (R)-octopamine and 300 mg of the resultant 4-N-benzenesulfonamidophenylacetic acid in 7 mL of DMF was added 0.5 mL of triethylamine and 490 mg of benzotriazolyl-N-oxy-tris(dimethylamino)phosphonium hexafluorophosphate. The reaction mixture was stirred at RT 2h, flash chromatography over silica gel eluting with 95:5 chloroform-methanol gave 322 mg of purified amide.

A solution of 220 mg of this amide in 13 mL of 1.0 M borane-THF was refluxed under argon for 2h followed by the addition of 3 mL of N,N-dimethylaminoethanol and further reflux for another hour. The solvent and excess volatiles were removed in vacuo and the residual solid was taken up in acetone and purified by PLC on silica gel (9:1 ethyl acetate:methanol) to yield 61 mg of the title compound: $^1H$ NMR (500 MHz, $CD_3OD$) δ7.73 (dt, 2H, J=2.1, 8.2Hz), 7.53 (tt, 1H, J=1.4, 7.6Hz), 7.44 (t, 2H, J=8 Hz), 7.18 (d, 2H, J=8.4 Hz), 7.05 (ABq, 4H, Jab=8.5 Hz), 6.76 (d, 2H, J=8.4Hz), 4.75 (dd, 1H, J=7.5, 7.6 Hz), 3.05-2.90 (m, 4H), 2.81 (t, 2H, J=7.6 Hz). Mass spec calcd. 412.5 found 4 13.2.

EXAMPLE 104

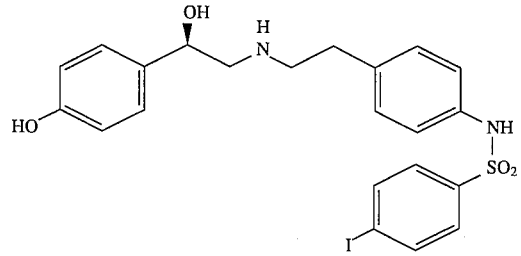

(R)-N-[4-[2-[[2-Hydroxy-2-(4-hydroxyphenyl)ethyl]amino]ethyl]phenyl]- 4-iodobenzenesulfonamide Following the procedure outlined in Example 103, the title compound was prepared: $^1H$ NMR (500 MHz, $CD_3OD$) δ7.77 (d, 2H, J=8.5 Hz), 7.43 (d, 2H, J=8.5 Hz), 7.15 (d, 2H, J=8.5 Hz), 7.02 (ABq, 4H, Jab=8.7 Hz), 6.75 (d, 2H, J=8.5

Hz), 4.67 (dd, 1H, J=4.4, 6.6 Hz), 2.90-2.66 (m, 6H). Mass spec calcd. 538.4 found 538.9.

EXAMPLE 105

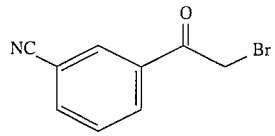

3-(2-bromoacetyl)benzonitrile

To a solution of 1.02 g (7.04 mmol) of 3-acetylbenzonitrile in mL of ethyl ether was added 1.02 g (3.52 mmol, 0.5 equiv) of dibromobarbituric acid. The mixture was allowed to stir at room temperature overnight. The resultant white slurry was filtered and the tiltrate was concentrated. Purification by flash chromotography (silica gel, ethyl acetate/hexane) gave 1.28 g (81%) of the title compound as a white solid: 1H NMR (400 MHz, CDCl$_3$) δ 8.26 (t, 1H, J=1.4 Hz), 8.20 (td, 1H, J=1.5, 8.0 Hz), 7.87 (dd, 1H, J=1.3, 7.8 Hz), 7.64 (t, 1H, J=7.9 Hz), 4.40 (s, 2H).

EXAMPLE 106

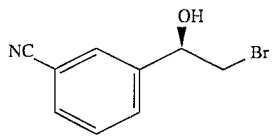

(R)-α-Bromomethyl-3-cyanophenylmethanol

To a suspension of 181 mg (0,623 mmol) of (R)-tetrahydro- 1-methyl-3,3-diphenyl- 1H,3H-pyrrolo[ 1,2c][1,3, 2]oxazaborole-borane (R-OAB catalyst) in 6 mL of THF at 0° C. was added dropwise 6.24 mL (6.24 mmol) of a 1 M solution of borane in THF. The resultant clear solution was allowed to stir for 5 min, and then a solution of 1.27 g (5.67 mmol) of bromoketone from Example 105 in 6 mL of THF was added slowly over 1 h. After the reaction was allowed to stir for 30 rain more, it was quenched by the dropwise addition of 6 mL of methanol and concentrated. Purification by flash chromatography (silica gel, 20–25% ethyl acetate/hexane) provided 944 mg (74%) of the title compound as a clear oil which crystallized: $^1$H NMR (400 MHz, CDCl$_3$) δ 7.70 (d, 1H, J=1.5 Hz), 7.62-7.60 (m, 2H), 7.48 (t, 1H, J=7.7 Hz), 4.95 (rid, 1H, J=3.4, 8.4 Hz), 3.63 (dd, 1H, J=3.4 Hz), 3.49 (dd, 1H, J=8.4 Hz).

EXAMPLE 107

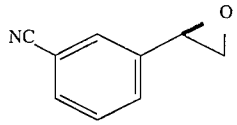

(R)-(3-cyanophenyl)oxirane

To a solution of 937 mg (4.14 mmol) of bromohydrin from Example 106 in 8 mL of methanol was added 601 mg (4.35 mmol, 1.05 equiv) of potassium carbonate. The reaction mixture was allowed to stir at room temperature for 7 h. It was then diluted with ethyl acetate, washed with water, dried over magnesium sulfate, and concentrated. Purification by flash chromatography (silica gel, 20% ethyl acetate/hexane) provided 573 mg (95%) of the title compound: $^1$H NMR (400 MHz, CDCl$_3$) δ0.7.59-7.55 (m, 2H), 7.49 (dd, 1H, J=1.6, 7.9 Hz), 7.44 (t, 1H, J=7.7 Hz), 3.87 (dd, 1H, J=2.5, 4.0 Hz), 3.17 (dd, 1H, J=4.1, 5.5 Hz), 2.74 (dd, 1H, J=2.5, 5.4 Hz).

EXAMPLE 108

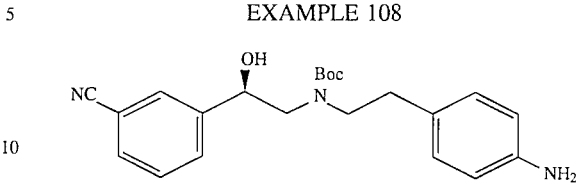

(R)-N-[2-[4-(aminophenyl)]ethyl]-2-hydroxy-2-( 3-cyanophenyl)ethyl-carbamic acid 1,1-dimethylethyl ester Following the procedures outlined in Examples 17 and 18, the title compound was prepared from the epoxide from Example 107: $^1$H NMR (400 MHz, CDCl$_3$) δ7.58-7.52 (br m, 3H), 7.41 (t, 1H, J=7.5 Hz), 6.89 (br d, 2H, J=7.6 Hz), 6.65 (br d, 2H, J=7.8 Hz), 4.82 (br dd, 1H, J=2.7, 7.9 Hz), 3.42-3.05 (br m, 4H), 2.75-2.55 (br m, 2H).

EXAMPLE 109

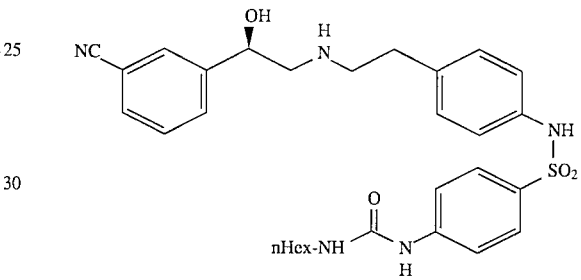

(R)-N-[4-[2-[[2-Hydroxy-2-(3-cyanophenyl)ethyl]amino] ethyl]phenyl]- 4-(hexylaminocarbonylamino)benzenesulfonamide Following the procedure outlined in Example 25, the title compound was prepared from the Boc aniline derivative from Example 108: $^1$H NMR (400 MHz, CD$_3$OD) δ7.70 (s, 1H), 7.63-7.57 (m, 4H), 7.48 (t, 1H, J=7.7 Hz), 7.43 (d, 2H, J=8.9 Hz), 7.06 (d, 2H, J=8.5 Hz), 6.99 (d, 2H, J=8.5 Hz), 4.77 (dd, 1H, J=3.9, 8.5 Hz), 3.15 (t, 2H, J=7.0 Hz), 2.86-2.69 (m, 6H), 1.49 (br m, 2H), 1.31 (br m, 6H), 0.90 (br t, 3H).

EXAMPLE 110

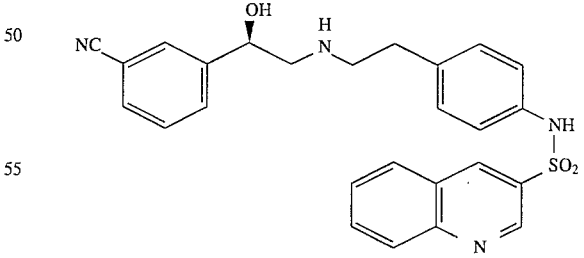

(R)-N-[4-[2-[[2-Hydroxy-2-(3-cyanophenyl)ethyl]amino] ethyl]phenyl]- 3-quinolinesulfonamide Following the procedure outlined in Example 25, the title compound was prepared from the Boc aniline derivative from Example and 3-quinolinesulfonyl chloride: $^1$H NMR (400 MHz, CD$_3$OD) δ9.02 (d, 1H, J=2.3 Hz), 8.68 (d, 1H, J=1.9 Hz), 8.06 (d, 1H, J=8.3 Hz), 8.02 (d, 1H, J=7.9 Hz), 7.90 (ddd, 1H, J=1.4, 7.0, 8.4 Hz), 7.72-7.69 (m, H), 7.62–7.58 (m, 2H), 7.47 (t, 1H, J=7.7 Hz), 7.07 (d, 2H, J=8.7 Hz), 7.03 (d, 2H, J=8.7 Hz), 4.76 (dd, 1H, J=4.0, 8.5 Hz), 2.85–2.68 (m, 6H).

Following the procedures outlined for Examples 14–31, the compounds listed in Table 6 were prepared.

TABLE 6

[Structure image]

| Example | R | Selected ¹H NMR (CD₃OD) Data |
|---|---|---|
| 111 | 4-(3-hexyl-2,4-imidazolidinedion-1-yl)phenyl | 4.40(s, 2H), 3.54(m, 2H), 1.68–1.59(m, 2H), 1.37–1.28(m, 6H), 0.91(m, 3H). |
| 112 | 4-(3-octyl-2,4-imidazolidinedion-1-yl)phenyl | 4.40(s, 2H), 3.52(m, 2H), 1.68–1.59(m, 2H), 1.38–1.23(m, 10H), 0.89(m, 3H). |
| 113 | 4-[2-(4-cyclohexylbutyl)-oxazol-5-yl]phenyl, trihydrochloride | 7.66(s, 1H), 5.35(m, 1H), 3.22–3.32(m, 5H), 2.95(m, 2H), 2.90(t, J=6.5Hz, 2H), 1.8(m, 2H), 1.69(m, 5H), 1.45(m, 2H), 1.24(m, 6H), 0.89(m. 2H) |
| 114 | 4-[2-[2-(4-fluorophenyl)ethyl]-oxazol-5-yl]phenyl | 7.49(s, 1H), 7.2(m, 2H), 6.99(m, 2H), 4.90(m, 1H), 3.05(m, 4H), 2.70–2.85(m, 6H) |
| 115 | 4-[2-(3-cyclopentylpropyl)-oxazol-5-yl]phenyl | 7.51(s, 1H), 4.90(m, 1H), 2.65–2.90(m, 8H), 1.80(m, 5H), 1.46–1.62(m, 4H), 1.05(m, 2H) |
| 116 | 4-(4-hexyl-3-oxo-[1,2,4]-triazol-2-yl)phenyl | 8.04(s, 1H), 3.69(m, 2H), 1.78–1.69(m, 2H), 1.39–1.28(m, 6H), 0.90(m, 3H). |
| 117 | 4-(4-octyl-3-oxo-[1,2,4]-triazol-2-yl)phenyl | 8.03(s, 1H), 3.69(m, 2H), 1.77–1.69(m, 2H), 1.38–1.25(m, 10H), 0.89(m, 3H). |
| 118 | 4-(4-heptyl-5-methyl-[1,2,3]-triazol-2-yl)phenyl | 2.28(s, 3H), 1.67(t, 2H, J=6.9Hz), 1.36–1.34(m, 4H), 1.31–1.29(m, 2H), 1.18(d, 4H, J=2.5Hz), 0.88(t, 3H, J=7.0Hz) |
| 119 | 4-[2-(cyclopentylmethyl)-oxazol-5-yl]phenyl | 7.50(s, 1H), 4.83(m, 1H), 2.95–2.70(m, 8H), 2.33(m, 1H), 1.81 (m, 2H), 1.67(m, 2H), 1.57(m 2H), 1.27(m, 2H) |
| 120 | 4-(4-diphenylhydroxymethyl-5-methyl-[1,2,3]-triazol-2-yl)phenyl | 7.36–7.33(m, 5H), 7.27(t, 4H, J=5.3Hz), 7.23(d, 2H, J=4.5Hz), 2.04(s, 3H) |
| 121 | 4-[4-[bis(4-fluorophenyl)hydroxymethyl]-5-methyl-[1,2,3]-triazol-2-yl]phenyl | 7.36–7.33(m, 5H), 7.05–6.99(m, 8H), 2.09(s, 3H) |
| 122 | 4-(3-hexylpyrazol-1-yl)phenyl | 8.13(d, 1H, J=2.5Hz), 7.75(s, 4H), 6.33(d, 1H, J=2.5Hz), 2.60 (t, 2H, J=7.6Hz), 1.65(m, 2H), 1.38–1.28(m, 6H), 0.88(t, 3H, J= 6.8Hz) |
| 123 | 4-[5-(1-hydroxypentyl)-[1,2,4]-oxadiazol-3-yl]phenyl | (CDCl₃) 4.98–4.91(m, 2H), 3.23–3.19(m, 1H), 1.99–1.93(m, 2H), 1.49–1.32(m, 4H), 0.92–0.86(m, 3H) |
| 124 | 4-[4-[(4-fluorophenyl)-hydroxymethyl]-5-methyl-[1,2,3]-triazol-2-yl]phenyl | 7.44–7.42(m, 2H), 7.09–7.02(m, 6H), 2.20(s, 3H) |

What is claimed is:

1. A compound having the formula I:

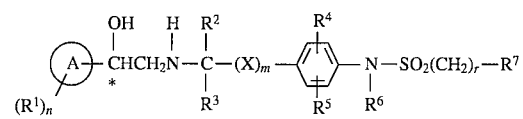

where n is 0 to 5;

m is 0 or 1;

r is 0 to 3;

A is Pyridinyl;

$R^1$ is (1) hydroxy, (2) oxo, (3) halogen, (4) cyano, (5) $NR^8R^8$, (6) $SR^8$, (7) trifluoromethyl, (8) $C_1$–$C_{10}$ alkyl, (9) $OR^8$, (10) $SO_2R^9$, (11) $OCOR^9$, (12) $NR^8COR^9$, (13) $COR^9$, (14) $NR^8SO_2R^9$, (15) $NR^8CO_2R^8$, or (16) $C_1$–$C_{10}$ alkyl substituted by hydroxy, halogen, cyano, $NR^8R^8$, $SR^8$, trifluoromethyl, $OR^8$, $C_3$–$C_8$ cycloalkyl, phenyl, $NR^8COR^9$, $COR^9$, $SO_2R^9$, $OCOR^9$, $NR^8SO_2R^9$ or $NR^8CO_2R^8$;

$R^2$ and $R^3$ are independently (1) hydrogen, (2) $C_1$–$C_{10}$ alkyl or (3) $C_1$–$C_{10}$ alkyl with 1 to 4 substituents selected from hydroxy, $C_1$–$C_{10}$ alkoxy, and halogen;

X is (1) —CH₂—, (2) —CH₂—CH₂—, (3) —CH=CH— or (4) —CH₂O—;

$R^4$ and $R^5$ are independently (1)hydrogen, (2) $C_1$–$C_{10}$ alkyl, (3) halogen, (4) $NHR^8$, (5) $OR^8$, (6) $SO_2R^9$ or (7) $NHSO_2R^9$;

$R^6$ is (1) hydrogen or (2) $C_1$–$C_{10}$ alkyl;

$R^7$ is Z-$(R^{1a})_n$;

$R^{1a}$ is (1) $R^1$, (2) $C_3$–$C_8$ cycloalkyl, (3) phenyl optionally substituted with up to 4 groups independently selected from $R^8$, $NR^8R^8$, $OR^8$, $SR^8$ and halogen, or (4) 5 or 6-membered heterocycle with from 1 to 4 heteroatoms selected from oxygen, sulfur and nitrogen, optionally substituted with up to four groups independently selected from oxo, $R^8$, $NR^8R^8$, $OR^8$, $SR^8$, and halogen;

Z is (1) phenyl, (2) naphthyl, (3) a 5 or 6-membered heterocyclic ring with from 1 to 4 heteroatoms selected from oxygen, sulfur and nitrogen, (4) a benzene ring fused to a $C_3$–$C_8$ cycloalkyl ring, (5) a benzene ring fused to a 5 or 6-membered heterocyclic ring with from 1 to 4 heteroatoms selected from oxygen, sulfur and nitrogen, (6) a 5 or 6-membered heterocyclic ring with from 1 to 4 heteroatoms selected from oxygen, sulfur and nitrogen fused to a 5 or 6-membered heterocyclic ring with from 1 to 4 heteroatoms selected from oxygen, sulfur and nitrogen, or (7) a 5 or 6-membered heterocyclic ring with from 1 to 4 heteroatoms selected from oxygen, sulfur and nitrogen fused to a $C_3$–$C_8$ cycloalkyl ring;

$R^8$ is (1 ) hydrogen, (2) $C_1$–$C_{10}$ alkyl, (3) $C_3$–$C_8$ cycloalkyl, (4) Z optionally having 1 to 4 substituents selected from halogen, nitro, oxo, $NR^{10}R^{10}$, $C_1$–$C_{10}$ alkyl, $C_1$–$C_{10}$ alkoxy, $C_1$–$C_{10}$ alkylthio, and $C_1$–$C_{10}$ alkyl having 1 to 4 substituents selected from hydroxy, halogen, $CO_2H$, $CO_2$—$C_1$—$C_{10}$ alkyl, $SO_2$—$C_1$—$C_{10}$ alkyl, $C_3$–$C_8$ cycloalkyl, $C_1$–$C_{10}$ alkoxy, and Z optionally substituted by from 1 to 3 of halogen, $C_1$–$C_{10}$ alkyl or $C_1$–$C_{10}$ alkoxy, or (5) $C_1$–$C_{10}$ alkyl having 1 to 4 substituents selected from hydroxy, halogen, $CO_2H$, $CO_2$—$C_1$—$C_{10}$ alkyl, $SO_2$—$C_1$—$C_{10}$ alkyl, $C_3$–$C_8$ cycloalkyl, $C_1$–$C_{10}$ alkoxy, $C_1$–$C_{10}$ alkyl, and Z optionally substituted by from 1 to 4 of halogen, $C_1$–$C_{10}$ alkyl or $C_1$–$C_{10}$ alkoxy;

$R^9$ is (1) $R^8$ or (2) $NR^8R^8$;

$R^{10}$ is (1) $C_1$–$C_{10}$ alkyl, or (2) two $R^{10}$ groups together with the N to which they are attached formed a 5 or 6-membered ring optionally substituted with $C_1$–$C_{10}$ alkyl; or a pharmaceutically acceptable salt thereof.

2. A compound of claim 1 where n is 0 to 3;

m is 1;

r is 0 to 2;

X is —$CH_2$—;

$R^1$ is (1) hydroxy, (2) halogen, (3) cyano, (4) trifluoromethyl, (5) $NR^8R^8$, (6) $NR^8SO_2R^9$, (7) $NR^8COR^9$, (8) $NR^8CO_2R^8$, or (9) $C_1$–$C_{10}$ alkyl optionally substituted by hydroxy;

$R^2$, $R^3$ are independently (1) hydrogen or (2) methyl;

$R^4$, $R^5$ and $R^6$ are each hydrogen;

$R^7$ is Z-$(R^{1a})_n$.

3. A compound of claim 1 having the formula Ia:

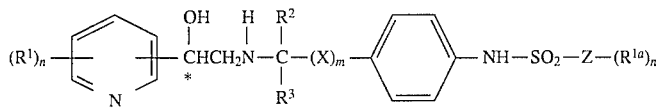

wherein n is 0 to 3;

m is 1

$R^1$ is (1) halogen or (2) $NR^8R^8$; $R^2$, $R^3$ are independently hydrogen or methyl;

$R^{1a}$ is (1) halogen, (2) $C_1$–$C_{10}$ alkyl, (3) $NR^8R^8$, (4) $NR^8COR^9$, (5) $NR^8CO_2R^8$, (6) $COR^9$, (7) $OCOR^9$, or (8) a 5 or 6-membered heterocycle with from 1 to 4 heteroatoms selected from oxygen, sulfur and nitrogen, optionally substituted with up to four groups independently selected from oxo, halogen, $R^8$, $NR^8R^8$, $OR^8$, and $SR^8$;

Z is (1) phenyl, (2) naphthyl, (3) a 5 or 6-membered heterocyclic ring with from 1 to 4 heteroatoms selected from oxygen, sulfur and nitrogen, (4) benzene ring fused to a 5 or 6-membered heterocyclic ring with from 1 to 3 heteroatoms selected from oxygen, sulfur and nitrogen, or (5) a 5 or 6-membered heterocyclic ring with from 1 to 4 heteroatoms selected from oxygen, sulfur and nitrogen fused to a $C_3$–$C_8$ cycloalkyl ring;

X is —$CH_2$—.

4. A compound of claim 3 wherein $R^2$ and $R^3$ are each hydrogen.

5. A compound of claim 1 having the formula Id

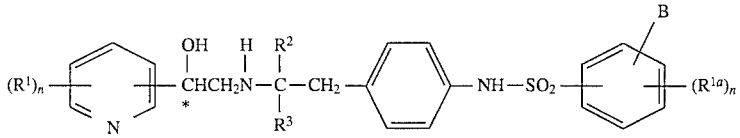

n is 0 or 1;

$R^1$ is $NR^8R^8$;

$R^2$ and $R^3$ are independently (1) hydrogen, or (2) methyl;

B is (1) hydrogen, (2) benzene fused to the benzene ring to form naphthyl, or (3) a 5 or 6-membered heterocycle with 1 to 4 heteroatoms selected from oxygen, sulfur and nitrogen atom fused to the benzene ring;

$R^{1a}$ is (1) halogen, (2) $C_1$–$C_{10}$ alkyl, (3) $NR^8R^8$, (4) $NR^8COR^9$, (5) $NR^8CO_2R^8$, (6) $COR^9$, or (7) a 5 or 6-membered heterocycle with from 1 to 4 heteroatoms selected from oxygen, sulfur and nitrogen, optionally substituted with up to four groups independently selected from oxo, $R^8$, $SR^8$, $OR^8$, and $NR^8R^8$; when B and the benzene ring form a fused ring system, $R^{1a}$ is attached to either ring;

$R^8$ is (1) hydrogen, (2) $C_1$–$C_{10}$ alkyl, (3) Z optionally having 1 to 4 substituents selected from nitro, oxo, and $NR^{10}R^{10}$, or (5) $C_1$–$C_{10}$ alkyl having 1 to 4 substituents selected from hydroxy, halogen, $C_1$–$C_{10}$ alkyl, $C_3$–$C_8$ cycloalkyl, and Z optionally substituted by from 1 to 4 of halogen, $C_1$–$C_{10}$ alkyl or $C_1$–$C_{10}$ alkoxy;

$R^9$ is (1) $R^8$ or (2) $NR^8R^8$;

$R^{10}$ is (1) $C_1$–$C_{10}$ alkyl, or (2) two $R^{10}$ groups together with the N to which they are attached formed a 5 or 6-membered ring optionally substituted with $C_1$–$C_{10}$ alkyl; and Z is (1) phenyl, (2) a 5 or 6-membered heterocyclic ring with from 1 to 4 heteroatoms selected from oxygen, sulfur and nitrogen, (3) a benzene ring fused to a 5 or 6-membered heterocyclic ring with from 1 to 4 heteroatoms selected from oxygen, sulfur and nitrogen, or (4) a 5 or 6-membered heterocyclic ring with from 1 to 4 heteroatoms selected from oxygen, sulfur and nitrogen fused to a $C_3$–$C_8$ cycloalkyl ring.

6. A compound of claim 1 having the formula Ie

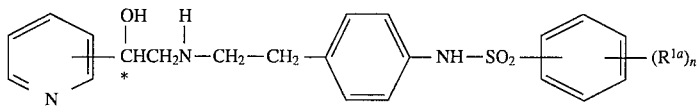

n is 0 or 1;

R$^{1a}$ is (1) halogen, (2) NR$^8$COR$^9$, or (3) a 5-membered heterocycle substituted with 0 or 1 oxo selected from imidazolidinone, imidazolone, oxadiazole, oxazole, triazole and tetrazolone, optionally substituted with up to three groups independently selected from R$^8$;

R$^8$ is (1) hydrogen, (2) C$_1$–C$_{10}$ alkyl, or (3) C$_1$–C$_{10}$ alkyl having 1 to 4 substituents selected from hydroxy, halogen, C$_1$–C$_{10}$ alkyl, C$_3$–C$_8$ cycloalkyl, and Z optionally substituted by from 1 to 4 of halogen, C$_1$–C$_{10}$ alkyl or C$_1$–C$_{10}$ alkoxy;

R$^9$ is NR$^8$R$^8$; Z is phenyl.

7. A compound of claim 1 selected from the group consisting of:

N-[4-[2-[[2-hydroxy-2-(6-aminopyridin-3-yl)ethyl]amino]ethyl]phenyl]- 4-(hexylaminocarbonylamino)benzenesulfonamide;

N-[4-[2-[[2-hydroxy-2-(6-aminopyridin-3-yl)ethyl]amino]ethyl]phenyl]- 4-iodobenzenesulfonamide;

N-[4-[2-[[2-hydroxy-2-(6-aminopyridin-3 -yl)ethyl]amino]ethyl]phenyl]-benzenesulfonamide;

N-[4-[2-[[2-hydroxy-2-(6-aminopyridin-3-yl)ethyl]amino]ethyl]phenyl]- 2-naphthalenesulfonamide;

N-[4-[2-[[2-hydroxy-2-(6-aminopyridin-3-yl)ethyl]amino]ethyl]phenyl]- 3-quinolinesulfonamide;

N-[4-[2-[[2-hydroxy-2-(6-aminopyridin-3-yl)ethyl]amino]ethyl]phenyl]- 5-benzisoxazolesulfonamide;

N-[4-[2-[[2-hydroxy-2-(6-aminopyridin-3-yl)ethyl]amino]ethyl]phenyl]- 4-[(hexylmethylaminocarbonyl)amino]benzenesulfonamide;

N-[4-[2-[[2-hydroxy-2-(6-aminopyridin-3-yl)ethyl]amino]ethyl]phenyl]- 4-[(dimethylaminocarbonyl)amino]benzenesulfonamide;

N-[4-[2-[[2-hydroxy-2-(6-aminopyridin-3-yl)ethyl]amino]ethyl]phenyl]- 4-(3 -hexyl-2-imidazolidinon-1-yl)benzenesulfonamide;

N-[4-[2-[[2-hydroxy-2-(3-pyridinyl)ethyl]amino]ethyl]phenyl]- 4-(hexylaminocarbonylamino)benzenesulfonamide;

N-[4-[2-[[2-hydroxy-2-(3-pyridinyl)ethyl]amino]ethyl]phenyl]- 4-isopropylbenzenesulfonamide;

N-[4-[2-[[2-hydroxy-2-(3-pyridinyl)ethyl]amino]ethyl]phenyl]- 2-naphthalenesulfonamide;

N-[4-[2-[[2-hydroxy-2-(3-pyridinyl)ethyl]amino]ethyl]phenyl]- 3-quinolinesulfonamide;

N-[4-[2-[[2-hydroxy-2-(3-pyridinyl)ethyl]amino]ethyl]phenyl]- 4-[(hexylmethylaminocarbonyl)amino]benzenesulfonamide;

N-[4-[2-[[2-hydroxy-2-(3-pyridinyl)ethyl]amino]ethyl]phenyl]-4-( 3-hexyl-2-imidazolidinon-1-yl)benzenesulfonamide;

N-[4-[2-[[2-hydroxy-2-(3-pyridinyl)ethyl]amino]ethyl]phenyl]- 4-iodobenzenesulfonamide;

N-[4-[2-[[2-hydroxy-2-(3-pyridinyl)ethyl]amino]ethyl]phenyl]-4-[3-( 3-cyclopentylpropyl)-2-imidazolidinon-1-yl]benzenesulfonamide;

N-[4-[2-[[2-hydroxy-2-(3-pyridinyl)ethyl]amino]ethyl]phenyl]-4-(3-octyl- 2-imidazolidinon-1-yl)benzenesulfonamide;

N-[4-[2-[[2-hydroxy-2-(3-pyridinyl)ethyl]amino]ethyl]phenyl]- 4-(3-hexyl-2-imidazolon-1-yl)benzenesulfonamide;

N-[4-[2-[[2-hydroxy-2-(3-pyridinyl)ethyl]amino]ethyl]phenyl]-4-(3-octyl- 2-imidazolon-1-yl)benzenesulfonamide;

N-[4-[2-[[2-hydroxy-2-(3-pyridinyl)ethyl]amino]ethyl]phenyl]-4-[3-( 3-cyclopentylpropyl)-2-imidazolon-1-yl]benzenesulfonamide;

N-[4-[2-[[2-hydroxy-2-(3-pyridinyl)ethyl]amino]ethyl]phenyl]-1-( 4-octylthiazol-2-yl )-5-indolinesulfonamide;

N-[4-[2-[[2-hydroxy-2-(3-pyridinyl)ethyl]amino]ethyl]phenyl]-4-( 5-pentyl-[1,2,4]-oxadiazol-3-yl)benzenesulfonamide;

N-[4-[2-[[2-hydroxy-2-(3-pyridinyl)ethyl]amino]ethyl]phenyl]-4-( 5-hexyl-[1,2,4]-oxadiazol-3-yl)benzenesulfonamide;

N-[4-[2-[[2-hydroxy-2-(3-pyridinyl)ethyl]amino]ethyl]phenyl]-4-( 5-heptyl-[1,2,4]-oxadiazol-3-yl)benzenesulfonamide;

N-[4-[2-[[2-hydroxy-2-(3-pyridinyl)ethyl]amino]ethyl]phenyl]-4-( 5-octyl-[1,2,4]-oxadiazol-3-yl)benzenesulfonamide;

N-[4-[2-[[2-hydroxy-2-(3-pyridinyl)ethyl]amino]ethyl]phenyl]-4-[5-( 2-cyclopentylethyl)-[1,2,4]-oxadiazol- 3-yl]benzenesulfonamide;

N-[4-[2-[[2-hydroxy-2-(3-pyridinyl)ethyl]amino]ethyl]phenyl]-4-[5-( 3-cyclopentylpropyl)-[1,2,4]ooxadiazol-3-yl]benzenesulfonamide;

N-[4-[2-[[2-hydroxy-2-(3-pyridinyl)ethyl]amino]ethyl]phenyl]-4-( 2-pentyloxazol-5-yl)benzenesulfonamide;

N-[4-[2-[[2-hydroxy-2-(3-pyridinyl)ethyl]amino]ethyl]phenyl]-4-( 2-hexyloxazol-5-yl)benzenesulfonamide;

N-[4-[2-[[2-hydroxy-2-(3-pyridinyl)ethyl]amino]ethyl]phenyl]-4-( 2-heptyloxazol-5-yl)benzenesulfonamide;

N-[4-[2-[[2-hydroxy-2-(3-pyridinyl)ethyl]amino]ethyl]phenyl]-4-( 2-octyloxazol-5-yl)benzenesulfonamide;

N-[4-[2-[[2-hydroxy-2-(3-pyridinyl)ethyl]amino]ethyl]phenyl]-4-[2-( 2-cyclopentylethyl)oxazol-5-yl]benzenesulfonamide;

N-[4-[2-[[2-hydroxy-2-(3-pyridinyl)ethyl]amino]ethyl]phenyl]-4-[2-( 3-cyclopentylpropyl)oxazol-5-yl]benzenesulfonamide;

N-[4-[2-[[2-h ydroxy-2-(3-pyridinyl)ethyl]amino]ethyl]phenyl]-4-( 4-hexyl-5-tetrazolon-1-yl)benzenesulfonamide;

N-[4-[2-[[2-hydroxy-2-(3-pyridinyl)ethyl]amino]ethyl]phenyl]-4-(4-octyl- 5-tetrazolon-1-yl)benzenesulfonamide;

N-[4-[2-[[2-hydroxy-2-(3-pyridinyl)ethyl]amino]ethyl]phenyl]-4-[4-( 3-cyclopentylpropyl)-5-tetrazolon-1-yl]benzenesulfonamide;

N-[4-[2-[[2-hydroxy-2-(3-pyridinyl)ethyl]amino]ethyl]phenyl]-4-[2-(cyclopentylmethyl)oxazol-5-yl]benzenesulfonamide;

N-[4-[2-[[2-hydroxy-2-(3-pyridinyl)ethyl]amino]ethyl]phenyl]-4-( 4-diphenylhydroxymethyl-5-methyl-[1,2,3]-triazol-2-yl)benzenesulfonamide;

N-[4-[2-[[2-hydroxy-2-(3-pyridinyl)ethyl]amino]ethyl]phenyl]-4-[4-[bis( 4-fluorophenyl)hydroxymethyl]-5-methyl-[1,2,3]-triazol- 2-yl]benzenesulfonamide;

N-[4-[2-[[2-hydroxy-2-(3-pyridinyl)ethyl]amino]ethyl]phenyl]-4-( 3-hexylpyrazol-1-yl)benzenesulfonamide;

N-[4-[2-[[2-hydroxy-2-(3-pyridinyl)ethyl]amino]ethyl]phenyl]-4-[5-( 1-hydroxypentyl)-[1,2,4]-oxadiazol-3-yl]benzenesulfonamide; and N-[4-[2-[[2-hydroxy-2-(3-pyridinyl)ethyl]amino]ethyl]phenyl]-4-[4-[( 4-fluorophenyl)hydroxymethyl]-5-methyl-[1, 2,3]-triazol- 2-yl]benzenesulfonamide.

8. A compound of claim 1 with the structural formula Ic:

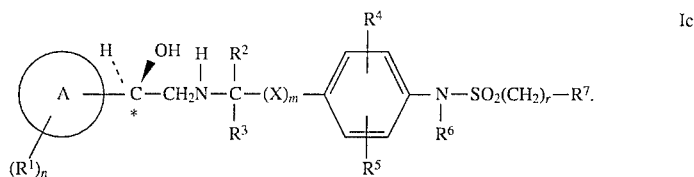

9. A compound of claim 1 which is (R)-N-[4-[2-[[2-hydroxy-2-(pyridin-3-yl)ethyl]amino]ethyl]phenyl]-4-[4-(3-cyclopentylpropyl)-5-tetrazolon-1-yl]benzenesulfonamide or a pharmaceutically acceptable salt thereof.

10. The dihydrochoride salt of the compound of claim 9.

11. A method for the treatment of diabetes which comprises administering to a diabetic patient an effective amount of a compound of claim 1.

12. A method for the treatment of obesity which comprises administering to an obese patient an effective amount of a compound of claim 1.

13. A method for lowering triglyceride levels and cholesterol levels or raising high density lipoprotein levels which comprises administering to a patient needing lower triglyceride and cholesterol levels or higher high density lipoprotein levels an effective amount of a compound of claim 1.

14. A method for decreasing gut motility which comprises administering to a patient in need of decreased gut motility, an effective amount of a compound of claim 1.

15. A method for reducing neurogenic inflammation of airways which comprises administering to a patient in need of reduced neurogenic inflammation, an effective amount of a compound of claim 1.

16. A method for reducing depression which comprises administering to a depressed patient an effective amount of a compound of claim 1.

17. A method for treating gastrointestinal disorders which comprises administering to a patient with gastrointestinal disorders an effective amount of a compound of claim 1.

18. A composition for the treatment of diabetes or obesity or for lowering triglyceride or cholesterol levels or increasing high density lipoprotein levels or for decreasing gut motility or for reducing neurogenic inflammation or for treating depression or for treating gastrointestinal disorders which comprises an inert carrier and an effective amount of a compound of claim 1.

* * * * *